United States Patent
Chojkier et al.

(10) Patent No.: US 10,434,134 B2
(45) Date of Patent: Oct. 8, 2019

(54) PEPTIDE TREATMENT FOR INFLAMMATION AND FIBROSIS

(71) Applicant: The Regents of the University of California, Oakland, CA (US)

(72) Inventors: Mario Chojkier, Del Mar, CA (US); Martina Buck, Del Mar, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/570,910

(22) PCT Filed: Apr. 11, 2016

(86) PCT No.: PCT/US2016/026966
§ 371 (c)(1),
(2) Date: Oct. 31, 2017

(87) PCT Pub. No.: WO2016/182660
PCT Pub. Date: Nov. 17, 2016

(65) Prior Publication Data
US 2018/0125919 A1    May 10, 2018

Related U.S. Application Data

(60) Provisional application No. 62/160,173, filed on May 12, 2015.

(51) Int. Cl.
| | |
|---|---|
| A61K 38/07 | (2006.01) |
| A61K 9/00 | (2006.01) |
| C07K 5/11 | (2006.01) |
| A61K 47/60 | (2017.01) |
| A61P 29/00 | (2006.01) |
| A61K 47/10 | (2017.01) |
| A61K 38/00 | (2006.01) |

(52) U.S. Cl.
CPC ............ *A61K 38/07* (2013.01); *A61K 9/0078* (2013.01); *A61K 47/10* (2013.01); *A61K 47/60* (2017.08); *A61P 29/00* (2018.01); *C07K 5/1019* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 7,655,472 B2 * | 2/2010 | Chojkier | A61K 38/1709 436/86 |
| 8,129,349 B2 * | 3/2012 | Chojkier | A61K 38/07 514/21.9 |
| 2010/0035825 A1 * | 2/2010 | Chojkier | A61K 38/07 514/18.9 |

FOREIGN PATENT DOCUMENTS

WO    WO-2006118805 A2 *  11/2006  ......... C07K 5/06078

OTHER PUBLICATIONS

Lifetein, "D Amino Acid Peptides", https://www.lifetein.com/Peptide-Synthesis-D-Amino-Acid.html, captured Feb. 23, 2014, pp. 1-3 (Year: 2014).*
Mahajan et al., "Structural Modification of Proteins and Peptides", Indian Journal of Pharmaceutical Education and Research, 2014, pp. 34-47 (Year: 2014).*
PCT International Search Report and Written Opinion for PCT Application No. PCT/US2016/026966 dated Sep. 8, 2016 (10 pages).
Buck et al., "C/EBPβ-Thr217 Phosphorylation Signaling Contributes to the Development of Lung Injury and Fibrosis in Mice," PLoS One, 2011, 6(10):e25497 (18 pages).
European Supplementary Search Report for EP Application No. 16793126 dated Nov. 13, 2018 (12 pages).
Buck et al., "C/EBPB Phosphorylation by RSK Creates a Functional XEXD Caspase Inhibitory Box Critical for Cell Survival," Molecualr Cell, 2001, 8:807-816.

* cited by examiner

*Primary Examiner* — Lianko G Garyu
(74) *Attorney, Agent, or Firm* — Eversheds Sutherland (US) LLP

(57) ABSTRACT

The invention is directed to peptides which inhibit phosphorylation of an amino phosphoacceptor domain of C/EBPβ and their use for treating inflammation and fibrosis.

18 Claims, 30 Drawing Sheets
Specification includes a Sequence Listing.

SEQUENCE LISTING

<160> NUMBER OF SEQ ID NOS: 7

<210> SEQ ID NO 1
<211> LENGTH: 20
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 1
tagggtgtgt ttaggcgaaa                                                  20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tctgttgcct tcctaataag                                                  20

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Lys Ser Lys Ala Lys Lys Ala Val Asp Lys His Ser Asp
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Lys Ala Lys Lys Ala Val Asp Lys His Ser
1               5                   10

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Lys Lys Ala Val Asp Lys His
1               5

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 6
```

```
Lys Ala Val Asp
1

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term CHO

<400> SEQUENCE: 7

Lys Ala Val Lys
1
```

PEPTIDE TREATMENT FOR INFLAMMATION AND FIBROSIS

CROSS REFERENCE TO RELATED APPLICATIONS

This application claims the priority benefit of PCT/US2016/026966 filed on Apr. 11, 2016 which claims priority to a U.S. Provisional Patent Application No. 62/160,173, filed May 12, 2015. The entire contents of which are hereby incorporated by reference.

STATEMENT AS TO FEDERALLY SPONSORED RESEARCH

This invention was made with government support under grants 300655 (DK087031) and DK100189 awarded by the National Institute of Health. The government has certain rights in the invention.

SEQUENCE LISTING

The instant application contains a Sequence Listing which has been submitted electronically in ASCII format and is hereby incorporated by reference in its entirety. Said ASCII copy, created on Apr. 11, 2016, is named 247106.000034_SL.txt and is 1,917 bytes in size.

FIELD OF THE INVENTION

The invention is related to therapeutic peptides which inhibit phosphorylation of C/EBPβ and their use for treating inflammation and fibrosis.

BACKGROUND OF THE INVENTION

Activation of liver myofibroblasts (of different origins) is responsible for the development of liver fibrosis in chronic liver diseases, and remarkably, the clearance of myofibroblasts by apoptosis would allow recovery from liver injury and reversal of liver fibrosis. There is agreement among liver experts that inhibiting or reversing myofibroblastic activation of different cellular origins is critical for the treatment of liver fibrosis. Finally, blocking the progression of liver fibrosis would decrease development of primary liver cancer since the majority of hepatocellular carcinomas arise in cirrhotic livers.

According to the NIH and the WHO (32; 33), the impact of liver diseases can be summarized annually as follows: i) liver cirrhosis: its mortality is approximately 800,000 worldwide (32), and 27,000 in the US; ii) chronic liver diseases: there are 421,000 hospitalizations for chronic liver diseases in the US. In addition, a medication that would prevent progression of liver fibrosis and decrease liver inflammation would impact the management of patients with non-alcoholic steatohepatitis (affects ~10 million in the US and it is an 'epidemic' worldwide); hepatitis C (~3 million in the US and 170 million worldwide have chronic infection), hepatitis B (~1 million in the US and 350 million worldwide have chronic infection), as well as those less common chronic liver diseases afflicting adults (primary biliary cirrhosis; sclerosing cholangitis; autoimmune hepatitis; genetic hemochromatosis) and children (including biliary atresia; α-1 antitrypsin deficiency and other rare genetic disorders) for which at present there are no available treatments.

There is no approved medication that directly inhibits or reverses liver fibrosis at present. Current treatments focus on managing the complications that result from liver inflammation and fibrosis. Drug candidates that are in clinical development in this area include: a) GR-MD-02 (Galectin Therapeutics Inc.—Indication—NASH (fatty liver disease) patients with advanced fibrosis—Phase 2). This drug is delivered in liposomes and targets macrophages for apoptosis and not the liver myofibroblasts responsible for the fibrogenesis pathway. Significant off-target adverse effects would be expected since the killing of macrophages could alter the immunological balance; b) Simtuzumab, an antifibrotic monoclonal antibody against lysyl oxidase-like 2 (LOXL2) enzyme (Gilead Sciences-Indications: liver fibrosis; primary sclerosing cholangitis; nonalcoholic steatohepatitis—Phase 2). This drug may prevent progression of active fibrogenesis but will not reverse existing crosslinked collagen fibers. In addition, it may induce immunogenic reactions. The efficacy of a large protein (antibody) is also a concern since it has to interact with LOXL2 in the potentially inaccessible extracellular matrix of a cirrhotic liver; c) Obeticholic acid (OCA) is a bile acid analog and agonist of the farnesoid X receptor (FXR) (Intercept Pharmaceuticals—OCA is being developed for a variety of chronic liver diseases including primary biliary cirrhosis (PBC), nonalcoholic steatohepatitis (NASH), and primary sclerosing cholangitis (PSC)—Phase 3). A major concern is that the blockade of the FXR is associated with the spontaneous development of liver tumors in the absence of the bile acid receptor farnesoid X receptor (26); and d) Emricasan (Conatus Pharmaceuticals—nonalcoholic fatty liver disease (NAFLD) subset of patients with inflammatory and/or fibrotic nonalcoholic steatohepatitis (NASH)—Phase 2). This drug is an active caspase protease inhibitor. A major concern is that prolonged inhibition of hepatocyte caspases may facilitate development of hepatocellular carcinoma and other organ tumors by eliminating a critical anti-tumor checkpoint (22).

A medication that would decrease or prevent the progression of lung fibrosis would impact the healthcare of patients with Idiopathic Pulmonary Fibrosis (IPF). IPF affects five (5) million people worldwide and 200,000 patients in the US (11). No therapy is known to improve health-related quality of life or survival in patients with IPF and these patients live only 3 to 5 years after diagnosis.

Drug candidates that are in clinical development in this area include: a) Esbriet (pirfenidone) is newly approved by the FDA for the treatment of IPF. However, the product description states that "Esbriet should be used with caution in patients with mild to moderate (Child Pugh Class A and B) hepatic impairment" and also those with mild, moderate or severe renal impairment. The drug may also result in elevated liver enzymes; photosensitivity reaction or rash; gastrointestinal disorders and also drug reactions with concomitant administration with strong inhibitors of CYP1A2 (e.g., fluvoxamine); b) OFEV (nintedanib) is also approved by the FDA for the treatment of IPF. However, the Safety Information Sheet regarding OFEV describes that the therapeutic can cause birth defects or death to an unborn baby, liver problems, bleeding and gastrointestinal disorders, and in more serious cases, stroke and heart attack; c) Oral prednisone (or some other form of corticosteroid) may decrease lung inflammation and the symptoms may improve significantly. The steroids may be used in combination with other drugs. However, the process of benefit to the patients (in terms of results seen) can be slow (1-3 months) and corticosteroids pose the risk of significant side effects; d) Fluimucil (N-acetylcysteine) has been mainly used for symptomatic relief of IPF; however, the supportive palliative care can be costly; e) Cytoxan (cyclophosphamide) may be used for those patients in whom steroid therapy has failed to be effective or is not possible and the drug may also be used as a combination therapeutic with a corticosteroid. The medication is immunosuppressive, and the response to therapy may be slow (6 months or more) and can present significant side effects including bone marrow suppression, blood disorders, and bladder inflammation; to name a few; and f) A combination of prednisone, azathioprine, and N-acetylcysteine (NAC) has been used for the treatment of IPF patients. However, NAC has been seen to be associated with increased risks of death and hospitalization of IPF patients.

Inflammation contributes to the pathogenesis of most acute and chronic liver diseases[1]. Excessive liver injury and inflammation associated with liver diseases induced by viral, toxic, immunologic, and metabolic diseases[2] results in liver dysfunction and in chronic conditions in the potential deposition of scar tissue and the development of cirrhosis, which is in turn a major contributor to the morbidity and mortality of patients affected by chronic liver diseases[2,3]. It was reported that amplification of toxic liver injury is mediated by macrophages since TLR-4 ko mice were resistant to hepatotoxins and that reconstitution of bone marrow irradiated TLR-4 ko mice with TLR-4$^{+/+}$macrophages conferred susceptibility of these animals to hepatotoxins[4]. The role of macrophages in liver inflammation in toxic liver injury has been confirmed using macrophage ablation[5], and further characterized in an experimental alcoholic liver injury model using an IL-1 receptor antagonist[6], and in LPS/D-galactosamine induced liver injury using Adenosine-$_{2A}$ ($A_{2A}$) receptor-ko mice[7]. Fas-mediated IL-18 secretion from macrophages causes acute liver injury in mice[8], and macrophage phagocytosis removes hepatocyte debris during hepatocyte injury[9]. However, the signal transduction mechanisms in liver macrophages that are indispensable to amplify liver injury have been only partially characterized[1].

The inflammasome is a protein complex that is essential for triggering activation of inflammatory reactions in macrophages as well as the consequent macrophage activation[1,10,11]. The CCAAT/Enhancer Binding Protein-β (C/EBPβ)[12,13,14] has been shown to be a critical signaling molecule for macrophages as expression of a dominant inhibitor of C/EBPβ DNA-binding sites[15] or a targeted deletion of C/EBPβ results in impaired macrophage differentiation[16].

In addition, C/EBPβ expression is dramatically increased during differentiation of these cells, and is induced by macrophage modulators (LPS, IL-1, G-CSF, TGFβ, vitamin D, retinoic acid)[13,17]. In this context, researchers have shown that phosphorylation of C/EBPβ by Ribosomal S-Kinase-2 (RSK-2), which is activated directly by Extracellular-Regulated Kinase (ERK)-½ phosphorylation, plays an essential role in the ERK/Mitogen Activated Protein Kinase (MAPK) signaling pathway regulating cell survival[18,19,20,21] Relevant to macrophage activation and survival, it was also reported that expression of the dominant positive, phosphorylation-mutant C/EBPβ-Glu217, which mimics phosphorylated C/EBPβ-Thr217 in biological assays[22], was sufficient to rescue the impaired macrophage function and activity induced by Anthrax lethal toxin[23].

SUMMARY OF THE INVENTION

As specified in the Background section above, there is a need for an effective treatment particularly for inflammation and fibrosis of human liver, lung, kidney, and any other tissues and/or organs. The present invention addresses these and other needs by providing novel therapeutic peptides and associated compositions and methods.

In one aspect, the invention provides an isolated peptide comprising the amino acid sequence Lys-Ala-Val-Asp, wherein at least one amino acid is D-amino acid and wherein said peptide is capable of inhibiting phosphorylation of human CCAAT/Enhancer Binding Protein-β (C/EBPβ) at Threonine 266 (Thr 266) or of mouse C/EBPβ at Thr 217.

In one embodiment, the Ala and/or Val within the amino acid sequence Lys-Ala-Val-Asp is D-amino acid (DAla, DVal). In one embodiment, the peptide is capable of selectively inhibiting phosphorylation of human CCAAT/Enhancer Binding Protein-β (C/EBPβ) at Threonine 266 (Thr 266). In one embodiment, the peptide is capable of inhibiting activation of myofibroblasts and/or macrophage inflammasome. In one embodiment, the peptide is between four amino acids and eight amino acids long. In one embodiment, the peptide comprises the amino acid sequence selected from the group consisting of Lys-DAla-DVal-Asp, Lys-DAla-Val-Asp and Lys-Ala-DVal-Asp. In one embodiment, the peptide consists of the amino acid sequence selected from the group consisting of Lys-DAla-DVal-Asp, Lys-DAla-Val-Asp and Lys-Ala-DVal-Asp. In one specific embodiment, the peptide comprises the amino acid sequence Lys-DAla-DVal-Asp. In one specific embodiment, the peptide consists of the amino acid sequence Lys-DAla-DVal-Asp. In one embodiment, the peptide consists of amino acid sequence selected from the group consisting of Lys-Ser-Lys-Ala-Lys-Lys-Ala-Val-Asp-Lys-His-Ser-Asp (SEQ ID NO: 3), Lys-Ala-Lys-Lys-Ala-Val-Asp-Lys-His-Ser (SEQ ID NO: 4), and Ala-Lys-Lys-Ala-Val-Asp-Lys-His (SEQ ID NO: 5) (e.g., peptides wherein the Ala and/or Val within the amino acid motif Lys-Ala-Val-Asp is D-amino acid). In one embodiment, the peptides of the invention further comprise polyethylene glycol (PEG). In one embodiment, the peptides of the invention further comprise a linker of acid (Ac) or mercaptopropionic acid (Mpr) or trimethyl lock (TML) lactonization (see, e.g., Greenwald, Journal of Controlled Release. 74, 2001, 159-171). In one embodiment, the carboxy terminal group of the peptides of the invention is OH, OCH$_3$, or NH$_2$ group. In one embodiment, the peptides of the invention are cyclic peptides.

In one embodiment, the peptide is selected from the group consisting of:
Lys-DAla-DVal-Asp,
Ac-Lys-DAla-DVal-Asp,
Mpr-Lys-DAla-DVal-Asp,
PEG-Lys-DAla-DVal-Asp,
PEG-Ac-Lys-DAla-DVal-Asp,
PEG-Mpr-Lys-DAla-DVal-Asp,
Lys-DAla-Val-Asp,
Ac-Lys-DAla-Val-Asp,
Mpr-Lys-DAla-Val-Asp,
PEG-Lys-DAla-Val-Asp,
PEG-Ac-Lys-DAla-Val-Asp,
PEG-Mpr-Lys-DAla-Val-Asp,
Lys-Ala-DVal-Asp,
Ac-Lys-Ala-DVal-Asp,
Mpr-Lys-Ala-DVal-Asp,
PEG-Lys-Ala-DVal-Asp,
PEG-Mpr-Lys-Ala-DVal-Asp, and
PEG-Mpr-Lys-Ala-DVal-Asp,
wherein the carboxy terminal group of the peptide is OH, OCH$_3$, or NH$_2$ group.

In one embodiment, the peptide is selected from the group consisting of Lys-DAla-DVal-Asp, Ac-Lys-DAla-DVal-Asp, Mpr-Lys-DAla-DVal-Asp, PEG-Lys-DAla-DVal-Asp, PEG- Ac-Lys-DAla-DVal-Asp, and PEG-Mpr-Lys-DAla-DVal-Asp, wherein the carboxy terminal group of the peptide is OH, OCH₃, or NH₂ group.

In one embodiment, the peptide is selected from the group consisting of Lys-DAla-DVal-Asp-NH2, Ac-Lys-DAla-DVal-Asp-NH2, Mpr-Lys-DAla-DVal-Asp-NH2, PEG-Lys-DAla-DVal-Asp-NH2, PEG-Ac-Lys-DAla-DVal-Asp-NH2, and PEG-Mpr-Lys-DAla-DVal-Asp-NH2.

In one embodiment, the peptide has the structure as shown in formula (I):

group consisting of idiopathic pulmonary fibrosis, radiation-induced pneumonitis, chronic obstructive pulmonary disease, and emphysema. In one embodiment, the disease is associated with kidney injury, kidney inflammation and/or kidney fibrosis. In one embodiment, the disease is glomerulonephritis or interstitial-tubular fibrosis. In one embodiment, the disease is selected from the group consisting of skin fibrosis secondary to burns, keloids, hypertrophic post-surgical wounds, scleroderma, esophageal or gastro-intestinal fibrosis secondary to corrosive materials, esophageal or

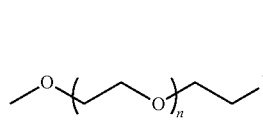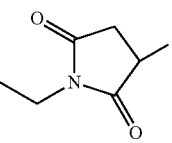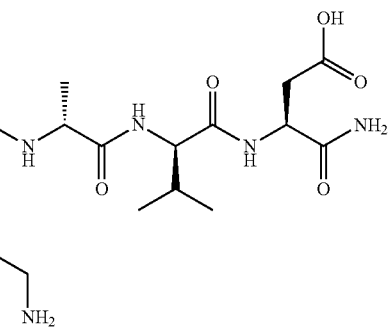

In conjunction with the peptides of the invention, the invention provides pharmaceutical compositions comprising one or more peptide(s) of the invention. In one embodiment, the peptide(s) is present in the composition in an amount effective to inhibit activation of myofibroblasts and/or macrophage inflammasome.

In another aspect, the invention provides a method for inhibiting tissue fibrosis in a subject in need thereof, said method comprising administering to the subject an effective amount of one or more peptides of the invention or a pharmaceutical composition comprising such one or more peptides. In one embodiment, the tissue is in the liver, lung or kidney. In one embodiment, the tissue fibrosis is associated with liver injury or liver inflammation. In one embodiment, the tissue fibrosis is associated with lung injury or lung inflammation. In one embodiment, the tissue fibrosis is associated with kidney injury or kidney inflammation.

In a further aspect, the invention provides a method for inhibiting macrophage and/or T cell inflammation in a subject in need thereof, said method comprising administering to the subject an effective amount of one or more peptides of the invention or a pharmaceutical composition comprising such one or more peptides.

In yet another aspect, the invention provides a method for treating a tissue fibrotic disease in a subject in need thereof comprising administering to the subject an effective amount of one or more peptides of the invention or a pharmaceutical composition comprising such one or more peptides. In one embodiment, the disease is associated with liver injury, liver inflammation and/or liver fibrosis. In one embodiment, the disease is liver cirrhosis or liver fibrosis of any etiology. In one embodiment, the disease is selected from the group consisting of non-alcoholic fatty liver disease (NAFLD), non-alcoholic steatohepatitis (NASH), alcoholic fatty liver disease, alcoholic steatohepatitis, hepatic steatosis, autoimmune hepatitis, chronic hepatitis C, chronic hepatitis B, primary biliary cirrhosis, secondary biliary cirrhosis, sclerosing cholangitis, alpha-1-antitrypsin deficiency, Wilson's disease, and biliary atresia. In one embodiment, the disease is associated with lung injury, lung inflammation and/or lung fibrosis. In one embodiment, the disease is selected from the gastro-intestinal fibrosis secondary to inflammatory diseases, fibrosis secondary to ischemic diseases, peritoneal fibrosis, pancreatic fibrosis, post-radiation fibrosis, cardiac fibrosis secondary to infarcts, brain fibrosis secondary to ischemia or infarcts, post-traumatic brain fibrosis, post-traumatic muscle fibrosis, and synovial/joint fibrosis.

In another aspect, the invention provides a method for treating an inflammatory disease in a subject in need thereof comprising administering to the subject an effective amount of one or more peptides of the invention or a pharmaceutical composition comprising such one or more peptides. In one embodiment, the disease is selected from the group consisting of alcoholic liver disease, non-alcoholic steato-hepatitis (NASH), autoimmune hepatitis, chronic hepatitis C, chronic hepatitis B, primary biliary cirrhosis, secondary biliary cirrhosis, sclerosing cholangitis, alpha-1-antitrypsin deficiency, Wilson's disease, biliary atresia, idiopathic pulmonary fibrosis, radiation-induced pneumonitis, chronic obstructive pulmonary disease, lung emphysema, lung chronic infections and/or inflammation, glomerulonephritis, interstitial-tubular fibrosis, skin inflammation secondary to burns, scleroderma, psoriasis, inflammatory bowel diseases, esophageal injury and/or inflammation, esophageal or gastro-intestinal inflammation post-radiation, inflammatory cardiomyopathy, brain inflammation post-trauma, Alzheimer's disease, encephalitis, meningitis, myositis, and arthritis.

In any of the above methods of the invention, the peptides or pharmaceutical compositions can be administered, e.g., systemically, by inhalation, topically, sublingually, orally, intranasally, or via a direct instillation to a tissue or organ.

In any of the above methods of the invention the subject can be, e.g., human or veterinary animal or an experimental animal model.

These and other aspects of the present invention will be apparent to those of ordinary skill in the art in the following description, claims and drawings.

BRIEF DESCRIPTION OF THE DRAWINGS

FIG. 2A. Liver fibrosis was determined by quantification of the Sirius stain (percentage fibrosis/area) as described (7; 25): control (0.02+/−0.01); lead peptide (0.8+/−0.7); alternate peptide 1 (2.1+/−1.0); alternate peptide 2 (3.5+/−1.2) and CCl4 (6.7+/−1.6%). P<0.0001 for lead peptide 1 and P<0.001 for alternate peptides 1 and 2. FIG. 2B. Liver fibrosis was detected histologically by the trichrome stain for liver fibrosis as it is the clinical standard. The control animals (receiving only vehicle control) had negligible fibrosis (stage 0-1/VI); animals receiving CCl4 for 16 weeks developed severe fibrosis (stage 5/VI or 6/VI; which would be clinically significant in patients); while animals receiving CCl4 for 16 weeks and also the lead PEG-30 kDa-peptide 1 starting at week-8 had minor fibrosis (stage 1-2/VI; which would not be clinically significant in patients).

FIG. 7A. LMF were co-cultured with induced Th1 or Th17 or Th2, control uninduced and Th1 or Th17 treated with the peptide. At least 100 cells per sample were counted for PCNA (N: 3) P<0.01 for Th1 and Th17 cells (NS for the other co-culture systems). FIG. 7B. Schematic representation of the Th1/Th17-LMF; Th2-LMF; and Th1/Th17 treated with peptide-LMF co-cultures.

FIG. 13a. Serum ALT (IU/ml) levels were determined 12 hours after a single IP dose of Jo-2 Ab (FasL). Mice expressing the phosphorylation mimic C/EBPβ-

Glu217 transgene were more susceptible than control C/EBPβ-wt mice to liver injury induced with Jo-2 Ab, judging by the serum ALT levels (P<0.0001). Mice expressing the non-phosphorylatable, C/EBPβ-Ala217 transgene were highly resistant to Fas-L induction of liver injury (P<0.01); n=20 mice per group. FIG. 13b. Jo-2 Ab induced minimal injury to cultured primary hepatocytes isolated from the phosphorylation mimic C/EBPβ-Glu217 transgenic mice (closed circles) when compared to hepatocytes from C/EBPβ-wt mice (open circles), judging by the apoptosis annexin-V assay (P<0.001). Control cultured primary hepatocytes from C/EBPβ-wt untreated with Jo-2 had less than 5% baseline apoptosis. FIG. 13c. Jo-2 Ab stimulated a greater infiltration of F4/80+ macrophage inflammatory cells in the livers of C/EBPβ-Glu217 mice than in the livers of C/EBPβ-wt mice (P<0.01). FIG. 13d. Jo-2 Ab induced a greater area of hepatocyte apoptotic damage in the livers of C/EBPβ-Glu217 mice than in the livers of C/EBPβ-wt mice (P<0.005). Values are mean (SD) of at least 6 animals per group and representative of three experiments.

FIG. 14a. After treatment with TGF-α, freshly isolated cultured liver macrophages from C/EBPβ-wt mice expressed activated RSK-phospho-Ser380 and phosphorylation of endogenous C/EBPβ on Thr217 (P<0.001). Representative examples of triplicate samples from three experiments. FIG. 14b. TGF-α induced also expression of NOS-2 in cultured liver macrophages (P<0.01). TO-PRO3 was used to stain cellular DNA. Representative examples of triplicate samples from three experiments. Fluorescence and bright-field imaging were quantified using the Keyence microscope BZ9000 analysis software programs.

FIG. 15a. Acute administration of CCl$_4$ stimulated a higher degree of macrophage infiltration in the livers of the phosphorylation mimic C/EBPβ-Glu217 mice compared to C/EBPβ-wt mice (P<0.0001), as identified by the expression of F4/80 by microscopy. The C/EBPβ-Ala217 transgene suppressed CCl$_4$-induced macrophage liver infiltration by about 90% when compared to C/EBPβ-wt mice (P<0.0001). CCl$_4$-induced macrophage liver infiltration was similar in TGFα transgenic mice and C/EBPβ-wt mice (NS). FIG. 15b. The degree of hepatocyte apoptosis induced by CCl$_4$ was increased in C/EBPβ-Glu217 mice (P<0.005) and in TGFα mice (P<0.05) but it was ameliorated in C/EBPβ-Ala217 mice (P<0.01) when compared to C/EBPβ-wt mice. FIG. 15c. CCl$_4$ stimulated higher serum ALT in C/EBPβ-Glu217 mice compared to C/EBPβ-wt mice (P<0.01). The C/EBPβ-Ala217 transgene suppressed CCl$_4$-induced serum ALT by about 50% when compared to C/EBPβ-wt mice (P<0.001). CCl$_4$-induced serum ALT was similar in TGFα transgenic mice and C/EBPβ-wt mice (NS). FIG. 15d. The dominant negative peptide that blocks C/EBPβ-Thr217 phosphorylation also inhibited the CCl$_4$-induction of liver macrophage infiltration by ~60% (P<0.01). FIG. 15e. The peptide inhibited the CCl$_4$-induction of hepatocyte apoptosis by ~45% (P<0.001). Values are mean (SD) of at least 6 animals per group and representative of two experiments.

FIG. 16a. C/EBPβ-wt mice that received Clodronate liposomes to deplete macrophages 24 hr before the administration of CCl$_4$, had a marked reduction in liver macrophages 30-hr after CCl$_4$ treatment (~90%; P<0.005). FIG. 16b. Depletion of macrophages with Clodronate liposomes in C/EBPβ-wt mice resulted in decreased liver injury at 30-hr after CCl$_4$ treatment as assessed by counting apoptotic hepatocytes in liver biopsies (P<0.01). FIG. 16c. Clodronate liposomes pretreatment of C/EBPβ-wt mice also decreased serum ALT levels by ~75% at 30-hr after CCl$_4$ treatment (P<0.005). FIGS. 16d, 16e & 16f. Clodronate liposomes induced an inhibition of TLR5, MyD88 and TLR4 expression in liver macrophages isolated from C/EBPβ-wt mice at 30-hr after CCl$_4$ treatment compared to liver macrophages isolated from CCl$_4$ treated C/EBPβ-wt mice that did not receive Clodronate liposomes (P<0.001). Values are mean (SD) of at least 6 animals per group and representative of two experiments.

FIG. 17a. Thirty-hours after CCl$_4$ treatment, the CD-11/CD-68 primary liver macrophages isolated from C/EBPβ-wt mice expressed phosphorylated C/EBPβ-Thr217 and inflammasome signal 1 complex gene products, TLR4, NFκB, IRF8 and MyD88. Expression of phosphorylated C/EBPβ-Thr217, TLR4, NFκB, IRF8 and MyD88 was blocked in C/EBPβ-Ala217 transgenic mice. Liver macrophages isolated from C/EBPβ-Glu217 transgenic mice expressed the inflammasome signal 1 complex in the absence of CCl$_4$ treatment, while liver macrophages isolated from TGFα mice expressed phosphorylated C/EBPβ-Thr217, TLR4, NFκB, IRF8 and MyD88 in the absence of CCl$_4$ treatment. (P<0.05 for C/EBPβ-wt mice treated with CCl$_4$; C/EBPβ-Glu217 mice; and TGFα mice). Fluorescence and bright-field imaging were quantified using the Keyence microscope BZ9000 analysis software programs. Representative examples of three independent experiments described as in FIGS. 15a-15e. FIG. 17b. C/EBPβ was immunoprecipitated and its associated proteins from freshly isolated primary liver macrophages 30 hr. after treatment of mice with vehicle or CCl$_4$ were analyzed. Phosphorylated C/EBPβ-Thr217 (or C/EBPβ-Glu217), but not unphosphorylated C/EBPβ-Thr217 (or C/EBPβ-Ala217), was associated with TLR4, NFκB, IRF8 and MyD88. Treatment with CCl$_4$ (and macrophage activation) increased the association between phosphorylated C/EBPβ-Thr217 and inflammasome signal 1 proteins. β-Actin was use as internal control for sample loading. Representative examples of three independent experiments described as in FIGS. 15a-15e.

FIG. 18a. Thirty-hours after CCl$_4$ treatment, the CD-11/CD-68 primary liver macrophages purified from C/EBPβ-wt mice expressed phosphorylated C/EBPβ-Thr217 and inflammasome signal 2 complex gene products, NALP3, TLR5, IL-1R1 and the adaptor protein ASC. Expression of phosphorylated C/EBPβ-Thr217, NALP3, TLR5, IL-1R1 and the adaptor protein ASC was blocked in C/EBPβ-Ala217 transgenic mice. Liver macrophages isolated from C/EBPβ-Glu217 transgenic mice expressed the inflammasome signal 2 complex in the absence of CCl$_4$ treatment, while liver macrophages isolated from TGFα mice expressed phosphorylated C/EBPβ-Thr217, NALP3, TLR5, IL-1R1 and the adaptor protein ASC in the absence of CCl$_4$ treatment. (P<0.01 for C/EBPβ-wt mice treated with CCl$_4$; C/EBPβ-Glu217 mice; and TGFα mice). Fluorescence and bright-field imaging were quantified using the Keyence microscope BZ9000 analysis software programs. Representative examples of three independent experiments described as in FIGS. 15a-15e. FIG. 18b. C/EBPβ was immunoprecipitated and its associated proteins from freshly isolated primary liver macrophages 30 hr after treatment of mice with vehicle or CCl₄ were analyzed. Phosphorylated C/EBPβ-Thr217 (or C/EBPβ-Glu217), but not unphosphorylated C/EBPβ-Thr217 (or C/EBPβ-Ala217), was associated with NALP3, TLR5, IL-1R1 and the adaptor protein ASC. Treatment with CCl₄ (and macrophage activation) increased the association between phosphorylated C/EBPβ-Thr217 and inflammasome signal 2 proteins. β-Actin was use as internal control for sample loading. Representative examples of three independent experiments described as in FIGS. 15a-15e.

FIG. 19a. Freshly isolated liver macrophages from the phosphorylation mimic C/EBPβ-Glu217 mice expressed an activated transcriptosome related to the Inflammasome when compared to C/EBPβ-wt mice. This included the increased expression of inflammasome genes (ASC, IRF-1, IRF-4, IRF-5, TCAM-2, TLR-6, TRAF-6, MyD-88, Nod-1 and Rel) as well as the increased expression of direct and indirect cytokine byproducts (IL-1β, IL-6, IL-15, IL-18 and TNFα). FIG. 19b. Freshly isolated C/EBPβ-Ala217 liver macrophages from mice treated with CCl₄ express an inhibited inflammasome transcriptosome when compared to freshly isolated liver macrophages from C/EBPβ-wt mice treated with CCl₄. This included the decreased expression of inflammasome genes (IRF-4, NALP-α, NALP-3, TCAM-2, TLR-1, TLR-3, TLR-5, TLR-6, TLR-7, TLR-8, TLR-9, Nod-1 and Rel) as well as the decreased gene expression of direct and indirect cytokine inflammasome byproducts (IL-1β, IL-6, IL-10, IL-15, IL-18, IL-23a and CXCL-3). FIG. 19c. Treatment with CCl₄ was associated with the induction of IL-18, active caspase-1 and IL-1β inflammasome protein expression in the livers of C/EBPβ-wt, C/EBPβ-Glu217, and TGFα mice. Values are mean (SD) of triplicates and representative of three experiments FIGS. 20a-20j. C/EBPβ-Thr266 associated with the inflammasome complex in liver macrophages from patients with Toxic Oil Syndrome. Liver biopsies from all 16 patients were analyzed with TOS that were still available at the Universidad Complutense Medical Center, Madrid, Spain. These patients had a moderately severe acute liver injury.

FIG. 23a. Representative histological samples of C/EBPβ-wt, TGFα, C/EBPβ-Glu217 (E), and C/EBPβ-Ala217(A) after 30 hrs. treatment with vehicle or CCl4. Formalin fixed liver samples were stained with reticulin histochemistry or F4/80 immunohistochemistry. The liver injury (reticulin stain) and the liver macrophage infiltration (F4/80) are induced by CCl4 but the induction is much more prominent in liver tissue from C/EBPβ-Glu217 mice. C/EBPβ-Ala217 mice were refractory to CCL4 stimulation of both liver injury and liver macrophage infiltration. FIG. 23b. Representative histological samples of C/EBPβ-wt mice after 30 hrs. treatment with vehicle or CCL4. Formalin fixed liver samples were stained with reticulin or F4/80 immunohistochemistry. The dominant negative peptide that blocks C/EBPβ-Thr217 phosphorylation (100 μg IP at 8 hr.), inhibited the CCl4-induction of liver injury (reticulin stain) by ~90% (P<0.001) and liver macrophage infiltration (F4/80) by ~60% (P<0.01). Representative example of experiment described in FIGS. 15a-15e above.

DETAILED DESCRIPTION OF THE INVENTION

Definitions

Figure 1:
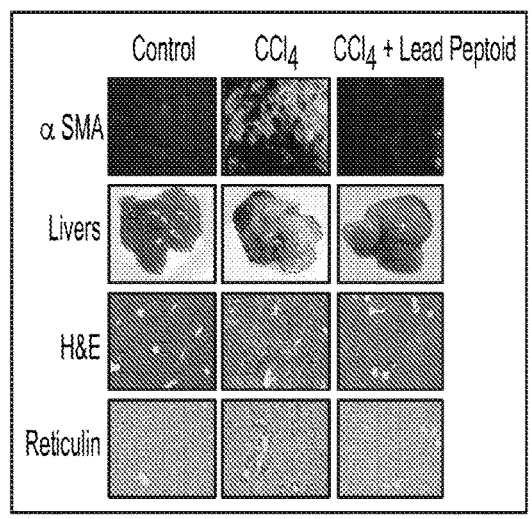
FIG. 1. The therapeutic lead peptide inhibits the activation of liver myofibroblasts and liver injury that induces fibrosis following exposure to the human hepatotoxin CCl4. A single dose of CCl4 was administered to C/EBPβ-wt mice (4). Eight hours later, animals received an IP injection of the therapeutic lead peptide (5 µg of peptide linked to PEG). Animals were sacrificed at 30 hr after the CCl4 administration. The animals receiving only CCl4 had intense activation of myofibroblasts (as determined by α-SMA) (upper row) and severe liver injury (as assessed by standard clinical examination just before sacrifice); the lead peptide blocked the discoloration and granular appearance of severe liver injury. The livers of treated mice were similar to control (second row). The histopathology induced by CCl4 was activation of myofibroblasts (α-SMA), severe liver injury (H&E stain) with collapse of the architecture (Reticulin stain). The therapeutic PEG-30 kDa-peptide decreased both the activation of myofibroblasts and the injury to the liver.

Unless defined otherwise, all technical and scientific terms used herein have the same meaning as commonly understood by one of ordinary skill in the art to which the invention pertains. Other specifically defined terms are to be construed in a manner consistent with the definition provided herein. Although any methods and materials similar or equivalent to those described herein can be used in the practice for testing of the present invention, the preferred materials and methods are described herein. In describing and claiming the present invention, the following terminology will be used.

As used in this specification and the appended claims, the singular forms "a", "an" and "the" include plural referents unless the content clearly dictates otherwise. Thus, for example, reference to "a construct" includes a combination of two or more nucleic acid constructs, and the like.

As used herein, the term "subject" refers to humans, mammals and/or veterinary animals (e.g., cats, dogs, cows, horses, sheep, pigs, etc.), and experimental animal models. In certain embodiments, the subject refers to a human patient, including both genders in adult and child populations.

In the context of the present invention insofar as it relates to any of the disease conditions recited herein, the terms "treat", "treatment", and the like mean to relieve or alleviate at least one symptom associated with such condition, or to slow or reverse the progression of such condition. Within the meaning of the present invention, the term "treat" also denotes to arrest, delay the onset (i.e., the period prior to clinical manifestation of a disease) and/or reduce the risk of developing or worsening a disease. The terms "treat", "treatment", and the like regarding a state, disorder or condition may also include (1) preventing or delaying the appearance of at least one clinical or sub-clinical symptom of the state, disorder or condition developing in a subject that may be afflicted with or predisposed to the state, disorder or condition but does not yet experience or display clinical or subclinical symptoms of the state, disorder or condition; or (2) inhibiting the state, disorder or condition, i.e., arresting, reducing or delaying the development of the disease or a relapse thereof (in case of maintenance treatment) or at least one clinical or sub-clinical symptom thereof; or (3) relieving the disease, i.e., causing regression of the state, disorder or condition or at least one of its clinical or sub-clinical symptoms.

The practice of the present invention employs, unless otherwise indicated, conventional techniques of statistical analysis, molecular biology (including recombinant techniques), microbiology, cell biology, and biochemistry, which are within the skill of the art. Such tools and techniques are described in detail in e.g., Sambrook et al. (2001) Molecular Cloning: A Laboratory Manual. 3 rd ed. Cold Spring Harbor Laboratory Press: Cold Spring Harbor, N.Y.; Ausubel et al. eds. (2005) Current Protocols in Molecular Biology. John Wiley and Sons, Inc.: Hoboken, N.J.; Bonifacino et al. eds. (2005) Current Protocols in Cell Biology. John Wiley and Sons, Inc.: Hoboken, N.J.; Coligan et al. eds. (2005) Current Protocols in Immunology, John Wiley and Sons, Inc.: Hoboken, N.J.; Coico et al. eds. (2005) Current Protocols in Microbiology, John Wiley and Sons, Inc.: Hoboken, N.J.; Coligan et al. eds. (2005) Current Protocols in Protein Science, John Wiley and Sons, Inc.: Hoboken, N.J.; and Enna et al. eds. (2005) Current Protocols in Pharmacology, John Wiley and Sons, Inc.: Hoboken, N.J. Additional techniques are explained, e.g., in U.S. Pat. No. 7,912,698 and U.S. Patent Appl. Pub. Nos. 2011/0202322 and 2011/0307437.

Peptides of the Invention, Compositions and Administration

The invention provides therapeutic peptides that are designed to block one phosphorylation on one molecular protein target in liver, lung, kidney, and/or other scar tissue to prevent and/or inhibit activation and production of myofibroblasts and/or macrophages so as to inhibit liver, lung, and/or other scar tissue inflammation and/or fibrosis. Since the peptides of the invention are nonessential to other mechanistic processes, they are highly specific and effective, while minimizing any potential off-target toxicity.

In certain embodiments, the invention provides therapeutic peptides that have high efficacy against the molecular target preventing activation of myofibroblasts and inhibiting liver, lung, and kidney fibrosis. In other embodiments, the invention further provides that by regulating the activation of the inflammasome in inflammatory macrophages and activate myofibroblasts, phosphorylated C/EBPβ-Phospho-Thr266 (human homologue of mouse C/EBPβ-Thr217) plays a major role in liver, lung, and kidney inflammation and injury. C/EBPβ-Phospho-Thr217 signaling that is evolutionarily conserved (identical in human C/EBPβ-Phospho-Thr266) modulates macrophage inflammasome activity and liver injury induced by different acting hepatotoxins. In certain embodiments, the therapeutic peptides also block activation of myofibroblasts through apoptotic mechanism, preventing progression and allowing regression of fibrosis of the scar tissue.

This invention provides therapeutic peptides which are designed to block phosphorylation on one protein, a single event critical to liver, lung, kidney, and/or other scar tissue production and nonessential to other mechanistic processes. Therefore, the candidate drugs are highly specific and effective, while minimizing any potential off-target toxicity. In certain embodiments, the invention provides that by regulating the activation of the inflammasome in liver lung, and/or kidney macrophages, phosphorylated C/EBPβ-Thr217 plays a major role in liver, lung, and/or kidney inflammation and injury. C/EBPβ-Phospho-Thr217 signaling that is evolutionarily conserved (identical in human C/EBPβ-Phospho-Thr266) modulates macrophage inflammasome activity and liver, lung, and/or kidney injury induced by different acting hepato-kidney, and/or lung toxins.

In certain embodiments, the peptides of the invention have been shown to stimulate apoptosis and block fibrogenesis, preventing progression and inducing regression of liver, lung, kidney, and/or other tissue inflammations and/or fibrosis. In certain embodiments, the peptides of the invention also show high efficacy against the molecular target, e.g., phosphorylation of C/EBPβ-Thr217 in activated liver, lung, and/or kidney myofibroblasts and/or macrophages, preventing activation of myofibroblasts and/or macrophages and inhibiting liver, lung and/or kidney inflammations and fibrogenesis.

In one aspect, the invention provides an isolated peptide comprising the amino acid sequence Lys-Ala-Val-Asp, wherein at least one amino acid is D-amino acid and wherein said peptide is capable of inhibiting phosphorylation of human CCAAT/Enhancer Binding Protein-β (C/EBPβ) at Threonine 266 (Thr 266) or mouse C/EBPβ at Thr 217. For examples of human and mouse C/EBPβ sequences see, e.g., human: GenBank Gene ID 1051; mouse: GenBank Gene ID 12608.

In one embodiment, the Ala and/or Val within the amino acid sequence Lys-Ala-Val-Asp is D-amino acid. In one embodiment, the peptide is capable of selectively inhibiting phosphorylation of human CCAAT/Enhancer Binding Protein-β (C/EBPβ) at Threonine 266 (Thr 266). In one embodiment, the peptide is capable of inhibiting activation of myofibroblasts and/or macrophage inflammasome. In one embodiment, the peptide is between four amino acids and eight amino acids long. In one embodiment, the peptide comprises the amino acid sequence selected from the group consisting of Lys-DAla-DVal-Asp, Lys-DAla-Val-Asp and Lys-Ala-DVal-Asp. In one embodiment, the peptide consists of the amino acid sequence selected from the group consisting of Lys-DAla-DVal-Asp, Lys-DAla-Val-Asp and Lys-Ala-DVal-Asp. In one embodiment, the peptide comprises the amino acid sequence Lys-DAla-DVal-Asp. In one embodiment, the peptide consists of the amino acid sequence Lys-DAla-DVal-Asp. In one embodiment, the peptide consists of amino acid sequence selected from the group consisting of Lys-Ser-Lys-Ala-Lys-Lys-Ala-Val-Asp-Lys-His-Ser-Asp (SEQ ID NO: 3), Lys-Ala-Lys-Lys-Ala-Val-Asp-Lys-His-Ser (SEQ ID NO: 4), and Ala-Lys-Lys-Ala-Val-Asp-Lys-His (SEQ ID NO: 5) (e.g., peptides wherein the Ala and/or Val within the amino acid motif Lys-Ala-Val-Asp is D-amino acid). In one embodiment, the peptide further comprises polyethylene glycol (PEG). In one embodiment, the peptide further comprises a linker of acid (Ac) or mercaptopropionic acid (Mpr) or trimethyl lock (TML) lactonization (see, e.g., Greenwald, Journal of Controlled Release. 74, 2001, 159-171). In one embodiment, the carboxy terminal group of the peptide is OH, OCH$_3$, or NH$_2$ group. In one embodiment, the peptide is a cyclic peptide.

In one embodiment, the peptide is selected from the group consisting of:
Lys-DAla-DVal-Asp,
Ac-Lys-DAla-DVal-Asp,
Mpr-Lys-DAla-DVal-Asp,
PEG-Lys-DAla-DVal-Asp,
PEG-Ac-Lys-DAla-DVal-Asp,
PEG-Mpr-Lys-DAla-DVal-Asp,
Lys-DAla-Val-Asp,
Ac-Lys-DAla-Val-Asp,
Mpr-Lys-DAla-Val-Asp,
PEG-Lys-DAla-Val-Asp,
PEG-Ac-Lys-DAla-Val-Asp,
PEG-Mpr-Lys-DAla-Val-Asp,
Lys-Ala-DVal-Asp,
Ac-Lys-Ala-DVal-Asp,
Mpr-Lys-Ala-DVal-Asp,
PEG-Lys-Ala-DVal-Asp,
PEG-Mpr-Lys-Ala-DVal-Asp, and
PEG-Mpr-Lys-Ala-DVal-Asp,
wherein the carboxy terminal group of the peptide is OH, OCH$_3$, or NH$_2$ group.

In one embodiment, the peptide is selected from the group consisting of Lys-DAla-DVal-Asp, Ac-Lys-DAla-DVal-Asp, Mpr-Lys-DAla-DVal-Asp, PEG-Lys-DAla-DVal-Asp, PEG-Ac-Lys-DAla-DVal-Asp, and PEG-Mpr-Lys-DAla-DVal-Asp, wherein the carboxy terminal group of the peptide is OH, OCH$_3$, or NH$_2$ group.

In one embodiment, the peptide is selected from the group consisting of Lys-DAla-DVal-Asp-NH2, Ac-Lys-DAla-DVal-Asp-NH2, Mpr-Lys-DAla-DVal-Asp-NH2, PEG-Lys-DAla-DVal-Asp-NH2, PEG-Ac-Lys-DAla-DVal-Asp-NH2, and PEG-Mpr-Lys-DAla-DVal-Asp-NH2.

In one embodiment, the peptide has the structure as shown in formula (I):

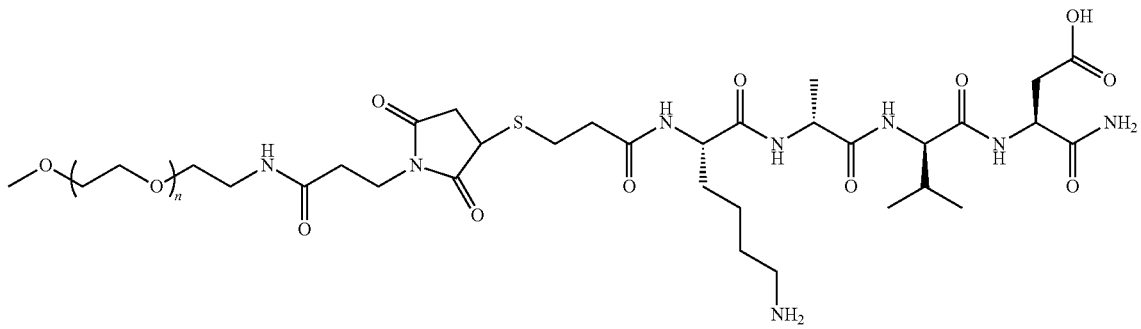

In addition to the above-disclosed peptides, the invention also encompasses C/EBPβ-Ala-217 amino acids 1 to 296 (mouse), C/EBPβ-Ala-217 fragment amino acids 216 to 253 (mouse), and C/EBPβ-Ala-217 amino acids 1 to 285 (mouse) (e.g., obtained based on GenBank Gene ID 12608 with Ala in position 217). Corresponding human sequences and fragments are also encompassed and can be obtained based on a human C/EBPβ sequence with Ala in position 266 (e.g., based on GenBank Gene ID 1051 with Ala in position 266).

The peptides of the invention can be modified, e.g., by the use of hetero-bifunctional linkers. Non-limiting examples of end groups for heterobifunctional PEGs are maleimide, vinyl sulfones, pyridyl disulfide, amine, carboxylic acids, and NHS esters (see, e.g., Veronese, Francesco M. "peptide and protein PEGylation: a review of problems and solutions." Biomaterials 22.5 (2001): 405-417). The peptides of the invention may employ third generation Pegylation agents that are, e.g., branched, Y-shaped or comb-shaped (see, e.g., Ryan, Sinéad M; Mantovani, Giuseppe; Wang, Xuexuan; Haddleton, David M; Brayden, David J (2008). "Advances in PEGylation of important biotech molecules: Delivery aspects". Expert Opinion on Drug Delivery 5 (4): 371-83). The peptides of the invention can be multimerized and/or cyclized (e.g., PolyPeptide Group).

Useful delivery technologies for the peptides of the invention include, e.g., LAR-depot microsphere polymer matrix (Midatech Pharma) and Protected Graft Copolymer (PGC™) technology (PharmaIN).

The peptides of the invention can be modified in various ways to improve their pharmacokinetic and other properties. Peptides can be modified at the amino (N−) terminus, and/or carboxy (C−) terminus and/or by replacement of one or more of the naturally occurring genetically encoded amino acids with an unconventional amino acid, modification of the side chain of one or more amino acid residues, peptide phosphorylation, and the like.

Amino terminus modifications include methylation (e.g., —NHCH$_3$ or —N(CH$_3$)$_2$), acetylation (e.g., with acetic acid or a halogenated derivative thereof such as α-chloroacetic acid, α-bromoacetic acid, or α-iodoacetic acid), adding a benzyloxycarbonyl (Cbz) group, or blocking the amino terminus with any blocking group containing a carboxylate functionality defined by RCOO— or sulfonyl functionality defined by R—SO$_2$—, where R is selected from alkyl, aryl, heteroaryl, alkyl aryl, and the like, and similar groups. One can also incorporate a desamino acid at the N-terminus (so that there is no N-terminal amino group) to decrease susceptibility to proteases or to restrict the conformation of the peptide compound.

Carboxy terminus modifications include replacing the free acid with a carboxamide group or forming a cyclic lactam at the carboxy terminus to introduce structural constraints. One can also cyclize the peptides of the invention, or incorporate a desamino or descarboxy residue at the termini of the peptide, so that there is no terminal amino or carboxyl group, to decrease susceptibility to proteases or to restrict the conformation of the peptide. C-terminal functional groups of the compounds of the present invention include amide, amide lower alkyl, amide di(lower alkyl), lower alkoxy, hydroxy, and carboxy, and the lower ester derivatives thereof, and the pharmaceutically acceptable salts thereof.

One can replace the naturally occurring side chains of the 20 genetically encoded amino acids (or the stereoisomeric D-amino acids) with other side chains, for instance with groups such as alkyl, lower alkyl, cyclic 4-, 5-, 6-, to 7-membered alkyl, amide, amide lower alkyl, amide di(lower alkyl), lower alkoxy, hydroxy, carboxy and the lower ester derivatives thereof, and with 4-, 5-, 6-, to 7-membered heterocyclic. For example, proline analogues in which the ring size of the proline residue is changed from 5 members to 4, 6, or 7 members can be employed. Cyclic groups can be saturated or unsaturated, and if unsaturated, can be aromatic or non-aromatic. Heterocyclic groups preferably contain one or more nitrogen, oxygen, and/or sulfur heteroatoms. Examples of such groups include the furazanyl, furyl, imidazolidinyl, imidazolyl, imidazolinyl, isothiazolyl, isoxazolyl, morpholinyl (e.g. morpholino), oxazolyl, piperazinyl (e.g., 1-piperazinyl), piperidyl (e.g., 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g., 1-pyrrolidinyl), pyrrolinyl, pyrrolyl, thiadiazolyl, thiazolyl, thienyl, thiomorpholinyl (e.g., thiomorpholino), and triazolyl. These heterocyclic groups can be substituted or unsubstituted. Where a group is substituted, the substituent can be alkyl, alkoxy, halogen, oxygen, or substituted or unsubstituted phenyl.

Common examples of conventional amino acid replacements include stereoisomers (e.g., D-amino acids) and unnatural amino acids such as, for example, L-ornithine, L-homocysteine, L-homoserine, L-citrulline, 3-sulfino-L-alanine, N-(L-arginino)succinate, 3,4-dihydroxy-L-phenylalanine, 3-iodo-L-tyrosine, 3,5-diiodo-L-tyrosine, triiodothyronine, L-thyroxine, L-selenocysteine, N-(L-arginino) taurine, 4-aminobutylate, (R,S)-3-amino-2-methylpropanoate, a,a-disubstituted amino acids, N-alkyl amino acids, lactic acid, β-alanine, 3-pyridylalanine, 4-hydroxyproline, O-phosphoserine, N-methylglycine, N-acetylserine, N-formylmethionine, 3-methylhistidine, 5-hydroxylysine, nor-leucine, and other similar amino acids and imino acids. A general method for site-specific incorporation of unnatural amino acids into proteins and peptides is described in Noren et al., Science, 244:182-188 (April 1989).

One can also readily modify peptides by phosphorylation, and other methods (e.g., as described in Hruby, et al. (1990) Biochem J. 268:249-262).

The peptide compounds of the invention also serve as structural models for non-peptidic compounds with similar biological activity. Those of skill in the art recognize that a variety of techniques are available for constructing compounds with the same or similar desired biological activity as the lead peptide compound, but with more favorable activity than the lead with respect to solubility, stability, and susceptibility to hydrolysis and proteolysis (see, e.g., Morgan and Gainor (1989) Ann. Rep. Med. Chem. 24:243-252). These techniques include replacing the peptide backbone with a backbone composed of phosphonates, amidates, carbamates, sulfonamides, secondary amines, and N-methylamino acids.

The present invention also provides conjugates of the disclosed peptide monomers. Thus, according to a preferred embodiment, the monomeric peptides of the present invention are dimerized or oligomerized, thereby enhancing their biological activity.

In one embodiment, the peptide monomers of the invention may be oligomerized using the biotin/streptavidin system. Biotinylated analogs of peptide monomers may be synthesized by standard techniques. For example, the peptide monomers may be C-terminally biotinylated. These biotinylated monomers are then oligomerized by incubation with streptavidin [e.g., at a 4:1 molar ratio at room temperature in phosphate buffered saline (PBS) or HEPES-buffered RPMI medium (Invitrogen) for 1 hour]. In a variation of this embodiment, biotinylated peptide monomers may be oligomerized by incubation with any one of a number of commercially available anti-biotin antibodies [e.g., goat anti-biotin IgG from Kirkegaard & Perry Laboratories, Inc. (Washington, D.C.)].

Linkers. In other embodiments, the peptide monomers of the invention can be dimerized by covalent attachment to at least one linker moiety. The linker ($L_K$) moiety can be a $C_{1-12}$ linking moiety optionally terminated with one or two —NH— linkages and optionally substituted at one or more available carbon atoms with a lower alkyl substituent (e.g., —NH—R—NH— wherein R is a lower ($C_{1-6}$) alkylene substituted with a functional group such as a carboxyl group or an amino group, such as, for example, a lysine residue or a lysine amide).

In an additional embodiment, polyethylene glycol (PEG) may serve as the linker $L_K$ that dimerizes two peptide monomers: for example, a single PEG moiety may be simultaneously attached to the N-termini of both peptide chains of a peptide dimer.

In yet another additional embodiment, the linker ($L_K$) moiety is preferably, but not necessarily, a molecule containing two carboxylic acids and optionally substituted at one or more available atoms with an additional functional group such as an amine capable of being bound to one or more PEG molecules. Such a molecule can be depicted as:

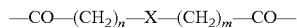

where n is an integer from 0 to 10, m is an integer from 1 to 10, X is selected from O, S, $N(CH_2)_pNR_1$, $NCO(CH_2)_pNR_1$, and $CHNR_1$, $R_1$ is selected from H, Boc, Cbz, etc., and p is an integer from 1 to 10.

Linkers can be incorporated into the peptide during peptide synthesis. For example, where a linker $L_K$ moiety contains two functional groups capable of serving as initiation sites for peptide synthesis and a third functional group (e.g., a carboxyl group or an amino group) that enables binding to another molecular moiety, the linker may be conjugated to a solid support. Thereafter, two peptide monomers may be synthesized directly onto the two reactive nitrogen groups of the linker $L_K$ moiety in a variation of the solid phase synthesis technique.

In alternate embodiments where a peptide dimer is dimerized by a linker $L_K$ moiety, said linker may be conjugated to the two peptide monomers of a peptide dimer after peptide synthesis. Such conjugation may be achieved by methods well established in the art. In one embodiment, the linker contains at least two functional groups suitable for attachment to the target functional groups of the synthesized peptide monomers. For example, a linker with two free amine groups may be reacted with the C-terminal carboxyl groups of each of two peptide monomers. In another example, linkers containing two carboxyl groups, either preactivated or in the presence of a suitable coupling reagent, may be reacted with the N-terminal or side chain amine groups, or C-terminal lysine amides, of each of two peptide monomers.

Spacers. A peptide monomer or dimer may further comprise one or more spacer moieties. Such spacer moieties may be attached to a peptide monomer or to a peptide dimer (e.g., such spacer moieties may be attached to the linker $L_K$ moiety that connects the monomers of a peptide dimer). For example, such spacer moieties may be attached to a peptide via the carbonyl carbon of a lysine linker, or via the nitrogen atom of an iminodiacetic acid linker. Such a spacer may connect a peptide to an attached water soluble polymer moiety or a protecting group.

In one embodiment, the spacer moiety is a $C_{1-12}$ linking moiety optionally terminated with —NH— linkages or carboxyl (—COOH) groups, and optionally substituted at one or more available carbon atoms with a lower alkyl substituent. In one embodiment, the spacer is R—COOH wherein R is a lower ($C_{1-6}$) alkylene optionally substituted with a functional group such as a carboxyl group or an amino group that enables binding to another molecular moiety. For example, the spacer may be a glycine (G) residue, or an amino hexanoic acid.

In other embodiments, the spacer is —NH—R—NH— wherein R is a lower ($C_{1-6}$) alkylene substituted with a functional group such as a carboxyl group or an amino group that enables binding to another molecular moiety. For example, the spacer may be a lysine (K) residue or a lysine amide (K—$NH_2$, a lysine residue wherein the carboxyl group has been converted to an amide moiety —$CONH_2$).

A spacer can be incorporated into the peptide during peptide synthesis. For example, where a spacer contains a free amino group and a second functional group (e.g., a carboxyl group or an amino group) that enables binding to another molecular moiety, the spacer may be conjugated to the solid support. Thereafter, the peptide may be synthesized directly onto the spacer's free amino group by standard solid phase techniques.

For example, a spacer containing two functional groups is first coupled to the solid support via a first functional group. Next a linker $L_K$ moiety having two functional groups capable of serving as initiation sites for peptide synthesis and a third functional group (e.g., a carboxyl group or an amino group) that enables binding to another molecular moiety is conjugated to the spacer via the spacer's second functional group and the linker's third functional group. Thereafter, two peptide monomers may be synthesized directly onto the two reactive nitrogen groups of the linker $L_K$ moiety in a variation of the solid phase synthesis technique. For example, a solid support coupled spacer with a free amine group may be reacted with a lysine linker via the linker's free carboxyl group.

In alternate embodiments where the peptide compounds contain a spacer moiety, said spacer may be conjugated to the peptide after peptide synthesis. Such conjugation may be achieved by methods well established in the art. In one embodiment, the linker contains at least one functional group suitable for attachment to the target functional group of the synthesized peptide. For example, a spacer with a free amine group may be reacted with a peptide's C-terminal carboxyl group. In another example, a linker with a free carboxyl group may be reacted with the free amine group of a peptide's N-terminus or of a lysine residue. In yet another example, a spacer containing a free sulfhydryl group may be conjugated to a cysteine residue of a peptide by oxidation to form a disulfide bond.

Water soluble polymer moieties. The peptide monomers, dimers, or multimers of the invention may further comprise one or more water soluble polymer moieties. Preferably, these polymers are covalently attached to the peptide compounds of the invention. Included with the below description, the U.S. patent application Ser. No. 10/844,933 and International Patent Application No. PCT/US04/14887, filed May 12, 2004, are incorporated by reference herein in their entirety.

In recent years, water-soluble polymers, such as polyethylene glycol (PEG), have been used for the covalent modification of peptides of therapeutic and diagnostic importance. Attachment of such polymers is thought to enhance biological activity, prolong blood circulation time, reduce immunogenicity, increase aqueous solubility, and enhance resistance to protease digestion (see, e.g., J. M. Harris, Ed., "Biomedical and Biotechnical Applications of Polyethylene Glycol Chemistry," Plenum, New York, 1992; Knauf, et al. (1988) J. Biol. Chem. 263; 15064; Tsutsumi, et al. (1995) J. Controlled Release 33:447; Kita, et al. (1990) Drug Des. Delivery 6:157; Abuchowski, et al. (1977) J. Biol. Chem.

252:582; Beauchamp, et al. (1983) Anal. Biochem. 131:25; Chen, et al. (1981) Biochim. Biophy. Acta 660:293).

The water soluble polymers useful for the peptide compounds of the invention may be, for example, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), poly(n-vinyl pyrrolidone)polyethylene glycol, propropylene glycol homopolymers, polypropylene oxide/ethylene oxide copolymers, and polyoxyethylated polyols.

The water soluble polymer may be of any molecular weight, and may be branched or unbranched. A preferred PEG for use in the present invention comprises linear, unbranched PEG having a low molecular weight. It is understood that in a given preparation of PEG, the molecular weights will typically vary among individual molecules. Some molecules will weight more, and some less, than the stated molecular weight. Such variation is generally reflect by use of the word "about" to describe molecular weights of the PEG molecules.

Peptides, peptide dimers and other peptide-based molecules of the invention can be attached to water-soluble polymers (e.g., PEG) using any of a variety of chemistries to link the water-soluble polymer(s) to the receptor-binding portion of the molecule (e.g., peptide+spacer). A typical embodiment employs a single attachment junction for covalent attachment of the water soluble polymer(s) to the receptor-binding portion, however in alternative embodiments multiple attachment junctions may be used, including further variations wherein different species of water-soluble polymer are attached to the receptor-binding portion at distinct attachment junctions, which may include covalent attachment junction(s) to the spacer and/or to one or both peptide chains. In some embodiments, the dimer or higher order multimer will comprise distinct species of peptide chain (i.e., a heterodimer or other heteromultimer). By way of example and not limitation, a dimer may comprise a first peptide chain having a PEG attachment junction and the second peptide chain may either lack a PEG attachment junction or utilize a different linkage chemistry than the first peptide chain and in some variations the spacer may contain or lack a PEG attachment junction and said spacer, if PEGylated, may utilize a linkage chemistry different than that of the first and/or second peptide chains. An alternative embodiment employs a PEG attached to the spacer portion of the receptor-binding portion and a different water-soluble polymer (e.g., a carbohydrate) conjugated to a side chain of one of the amino acids of the peptide portion of the molecule.

A wide variety of polyethylene glycol (PEG) species may be used for PEGylation of the receptor-binding portion (peptides+spacer). Substantially any suitable reactive PEG reagent can be used. In preferred embodiments, the reactive PEG reagent will result in formation of a carbamate or amide bond upon conjugation to the receptor-binding portion. Suitable reactive PEG species include, but are not limited to, those which are available for sale in the Drug Delivery Systems catalog (2003) of NOF Corporation (Yebisu Garden Place Tower, 20-3 Ebisu 4-chome, Shibuya-ku, Tokyo 150-6019) and the Molecular Engineering catalog (2003) of Nektar Therapeutics (490 Discovery Drive, Huntsville, Ala. 35806). For example and not limitation, the following PEG reagents are often preferred in various embodiments: mPEG2-NHS, mPEG2-ALD, multi-Arm PEG, mPEG (MAL)2, mPEG2(MAL), mPEG-NH2, mPEG-SPA, mPEG-SBA, mPEG-thioesters, mPEG-Double Esters, mPEG-BTC, mPEG-ButyrALD, mPEG-ACET, heterofunctional PEGs (NH2-PEG-COOH, Boc-PEG-NHS, Fmoc-PEG-NHS, NHS-PEG-VS, NHS-PEG-MAL), PEG acrylates (ACRL-PEG-NHS), PEG-phospholipids (e.g., mPEG-DSPE), multiarmed PEGs of the SUNBRITE series including the GL series of glycerine-based PEGs activated by a chemistry chosen by those skilled in the art, any of the SUNBRITE activated PEGs (including but not limited to carboxyl-PEGs, p-NP-PEGs, Tresyl-PEGs, aldehyde PEGs, acetal-PEGs, amino-PEGs, thiol-PEGs, maleimido-PEGs, hydroxyl-PEG-amine, amino-PEG-COOH, hydroxyl-PEG-aldehyde, carboxylic anhydride type-PEG, functionalized PEG-phospholipid, and other similar and/or suitable reactive PEGs as selected by those skilled in the art for their particular application and usage.

The number of polymer molecules attached may vary; for example, one, two, three, or more water soluble polymers may be attached to a peptide of the invention. The multiple attached polymers may be the same or different chemical moieties (e.g., PEGs of different molecular weight). In some cases, the degree of polymer attachment (the number of polymer moieties attached to a peptide and/or the total number of peptides to which a polymer is attached) may be influenced by the proportion of polymer molecules versus peptide molecules in an attachment reaction, as well as by the total concentration of each in the reaction mixture. In general, the optimum polymer versus peptide ratio (in terms of reaction efficiency to provide for no excess unreacted peptides and/or polymer moieties) will be determined by factors such as the desired degree of polymer attachment (e.g., mono, di-, tri-, etc.), the molecular weight of the polymer selected, whether the polymer is branched or unbranched, and the reaction conditions for a particular attachment method.

There are a number of PEG attachment methods available to those skilled in the art (see, e.g., Goodson, et al. (1990) Bio/Technology 8:343; EP 0 401 384; Malik, et al., (1992) Exp. Hematol. 20:1028-1035; PCT Pub. No. WO 90/12874; U.S. Pat. Nos. 5,757,078; and 6,077,939). For example, activated PEG may be covalently bound to amino acid residues via a reactive group, such as a free amino group in N-terminal amino acid residues and lysine (K) residues or a free carboxyl group in C-terminal amino acid residues. Sulfhydryl groups (e.g., as found on cysteine residues) may also be used as a reactive group for attaching PEG. In addition, enzyme-assisted methods for introducing activated groups (e.g., hydrazide, aldehyde, and aromatic-amino groups) specifically at the C-terminus of a polypeptide have been described (Schwarz, et al. (1990) Methods Enzymol. 184:160; Rose, et al. (1991) Bioconjugate Chem. 2:154; Gaertner, et al. (1994) J. Biol. Chem. 269:7224).

For example, PEG molecules may be attached to peptide amino groups using methoxylated PEG ("mPEG") having different reactive moieties. Such polymers include mPEG-succinimidyl succinate, mPEG-succinimidyl carbonate, mPEG-imidate, mPEG-4-nitrophenyl carbonate, and mPEG-cyanuric chloride. Similarly, PEG molecules may be attached to peptide carboxyl groups using methoxylated PEG with a free amine group (mPEG-NH$_2$).

Where attachment of the PEG is non-specific and a peptide containing a specific PEG attachment is desired, the desired PEGylated compound may be purified from the mixture of PEGylated compounds. For example, if an N-terminally PEGylated peptide is desired, the N-terminally PEGylated form may be purified from a population of randomly PEGylated peptides (i.e., separating this moiety from other monoPEGylated moieties).

Site-specific PEGylation at the N-terminus, side chain, and C-terminus can be performed through (i) solid-phase synthesis (see, e.g., Felix, et al. (1995) Int. J. Peptide Protein Res. 46:253) or (ii) attaching a peptide to extremities of liposomal surface-grafted PEG chains in a site-specific manner through a reactive aldehyde group at the N-terminus generated by sodium periodate oxidation of N-terminal threonine (see, e.g., Zalipsky, et al. (1995) Bioconj. Chem. 6:705; this method is limited to polypeptides with N-terminal serine or threonine residues), or (iii) via a hydrazone, reduced hydrazone, oxime, or reduced oxime bond is described in U.S. Pat. No. 6,077,939.

In one method, selective N-terminal PEGylation may be accomplished by reductive alkylation which exploits differential reactivity of different types of primary amino groups (lysine versus the N-terminal) available for derivatization in a particular protein. Under the appropriate reaction conditions, a carbonyl group containing PEG is selective attached to the N-terminus of a peptide. For example, one may selectively N-terminally PEGylate the protein by performing the reaction at a pH which exploits the $pK_a$ differences between the ε-amino groups of a lysine residue and the α-amino group of the N-terminal residue of the peptide. By such selective attachment, PEGylation takes place predominantly at the N-terminus of the protein, with no significant modification of other reactive groups (e.g., lysine side chain amino groups). Using reductive alkylation, the PEG should have a single reactive aldehyde for coupling to the protein (e.g., PEG proprionaldehyde may be used).

Site-specific mutagenesis is a further approach which may be used to prepare peptides for site-specific polymer attachment. By this method, the amino acid sequence of a peptide is designed to incorporate an appropriate reactive group at the desired position within the peptide. For example, WO 90/12874 describes the site-directed PEGylation of proteins modified by the insertion of cysteine residues or the substitution of other residues for cysteine residues.

Where PEG is attached to a spacer or linker moiety, similar attachment methods may be used. In this case, the linker or spacer contains a reactive group and an activated PEG molecule containing the appropriate complementary reactive group is used to effect covalent attachment. In preferred embodiments the linker or spacer reactive group contains a terminal amino group (i.e., positioned at the terminus of the linker or spacer) which is reacted with a suitably activated PEG molecule to make a stable covalent bond such as an amide or a carbamate. Suitable activated PEG species include, but are not limited to, mPEG-para-nitrophenylcarbonate (mPEG-NPC), mPEG-succinimidyl carbonate (mPEG-SC), and mPEG-succinimidyl propionate (mPEG-SPA). In other preferred embodiments, the linker or spacer reactive group contains a carboxyl group capable of being activated to form a covalent bond with an amine-containing PEG molecule under suitable reaction conditions. Suitable PEG molecules include mPEG-$NH_2$ and suitable reaction conditions include carbodiimide-mediated amide formation or the like.

The peptides of the invention may be prepared by classical methods known in the art. These standard methods include exclusive solid phase synthesis, automated solid phase synthesis, partial solid phase synthesis methods, fragment condensation, classical solution synthesis, and recombinant DNA technology (See, e.g., Merrifield J. Am. Chem. Soc. 1963 85:2149 and Merrifield et al., 1982, Biochemistry, 21:502).

A preferred method for peptide synthesis is solid phase synthesis. Solid phase peptide synthesis procedures are well-known in the art (see, e.g., Stewart, Solid Phase Peptide Syntheses, Freeman and Co.: San Francisco, 1969; 2002/2003 General Catalog from Novabiochem Corp, San Diego, USA; Goodman, Synthesis of Peptides and Peptidomimetics, Houben-Weyl, Stuttgart 2002). In solid phase synthesis, synthesis is typically commenced from the C-terminal end of the peptide using an α-amino protected resin. A suitable starting material can be prepared, for instance, by attaching the required α-amino acid to a chloromethylated resin, a hydroxymethyl resin, a polystyrene resin, a benzhydrylamine resin, or the like. One such chloromethylated resin is sold under the trade name BIO-BEADS SX-1 by Bio Rad Laboratories (Richmond, Calif.). The preparation of the hydroxymethyl resin has been described (Bodonszky, et al. (1966) Chem. Ind. London 38:1597). The benzhydrylamine (BHA) resin has been described (Pietta and Marshall, 1970, Chem. Commun., 650), and the hydrochloride form is commercially available from Beckman Instruments, Inc. (Palo Alto, Calif.). For example, an α-amino protected amino acid may be coupled to a chloromethylated resin with the aid of a cesium bicarbonate catalyst, according to the method described by Gisin (1973, Helv. Chim. Acta 56:1467).

After initial coupling, the α-amino protecting group is removed, for example, using trifluoroacetic acid (TFA) or hydrochloric acid (HCl) solutions in organic solvents at room temperature. Thereafter, α-amino protected amino acids are successively coupled to a growing support-bound peptide chain. The α-amino protecting groups are those known to be useful in the art of stepwise synthesis of peptides, including: acyl-type protecting groups (e.g., formyl, trifluoroacetyl, acetyl), aromatic urethane-type protecting groups [e.g., benzyloxycarboyl (Cbz) and substituted Cbz], aliphatic urethane protecting groups [e.g., t-butyloxycarbonyl (Boc), isopropyloxycarbonyl, cyclohexyloxycarbonyl], and alkyl type protecting groups (e.g., benzyl, triphenylmethyl), fluorenylmethyl oxycarbonyl (Fmoc), allyloxycarbonyl (Alloc), and 1-(4,4-dimethyl-2,6-dioxocyclohex-1-ylidene)ethyl (Dde).

The side chain protecting groups (typically ethers, esters, trityl, PMC (2,2,5,7,8-pentamethyl-chroman-6-sulphonyl), and the like) remain intact during coupling and is not split off during the deprotection of the amino-terminus protecting group or during coupling. The side chain protecting group must be removable upon the completion of the synthesis of the final peptide and under reaction conditions that will not alter the target peptide. The side chain protecting groups for Tyr include tetrahydropyranyl, tert-butyl, trityl, benzyl, Cbz, Z—Br—Cbz, and 2,5-dichlorobenzyl. The side chain protecting groups for Asp include benzyl, 2,6-dichlorobenzyl, methyl, ethyl, and cyclohexyl. The side chain protecting groups for Thr and Ser include acetyl, benzoyl, trityl, tetrahydropyranyl, benzyl, 2,6-dichlorobenzyl, and Cbz. The side chain protecting groups for Arg include nitro, Tosyl (Tos), Cbz, adamantyloxycarbonyl mesitoylsulfonyl (Mts), 2,2,4,6,7-pentamethyldihydrobenzofurane-5-sulfonyl (Pbf), 4-methoxy-2,3,6-trimethyl-benzenesulfonyl (Mtr), or Boc. The side chain protecting groups for Lys include Cbz, 2-chlorobenzyloxycarbonyl (2-Cl-Cbz), 2-bromobenzyloxycarbonyl (2-Br-Cbz), Tos, or Boc.

After removal of the α-amino protecting group, the remaining protected amino acids are coupled stepwise in the desired order. Each protected amino acid is generally reacted in about a 3-fold excess using an appropriate carboxyl group activator such as 2-(1H-benzotriazol-1-yl)-1,1,3,3 tetramethyluronium hexafluorophosphate (HBTU) or dicyclohexylcarbodimide (DCC) in solution, for example, in methylene chloride ($CH_2Cl_2$), N-methyl pyrrolidone, dimethyl formamide (DMF), or mixtures thereof.

After the desired amino acid sequence has been completed, the desired peptide is decoupled from the resin support by treatment with a reagent, such as trifluoroacetic acid (TFA) or hydrogen fluoride (HF), which not only cleaves the peptide from the resin, but also cleaves all remaining side chain protecting groups. When a chloromethylated resin is used, hydrogen fluoride treatment results in the formation of the free peptide acids. When the benzhydrylamine resin is used, hydrogen fluoride treatment results directly in the free peptide amide. Alternatively, when the chloromethylated resin is employed, the side chain protected peptide can be decoupled by treatment of the peptide resin with ammonia to give the desired side chain protected amide or with an alkylamine to give a side chain protected alkylamide or dialkylamide. Side chain protection is then removed in the usual fashion by treatment with hydrogen fluoride to give the free amides, alkylamides, or dialkylamides. In preparing the esters of the invention, the resins used to prepare the peptide acids are employed, and the side chain protected peptide is cleaved with base and the appropriate alcohol (e.g., methanol). Side chain protecting groups are then removed in the usual fashion by treatment with hydrogen fluoride to obtain the desired ester. The resultant peptide can be further purified using HPLC.

These procedures can also be used to synthesize peptides in which amino acids other than the 20 naturally occurring, genetically encoded amino acids are substituted at one, two, or more positions of any of the compounds of the invention. Synthetic amino acids that can be substituted into the peptides of the present invention include, but are not limited to, N-methyl, L-hydroxypropyl, L-3, 4-dihydroxyphenylalanyl, δ amino acids such as L-☐ δ-hydroxylysyl and D-☐ δ-methylalanyl, L-δ-methylalanyl, β amino acids, and isoquinolyl. D-amino acids and non-naturally occurring synthetic amino acids can also be incorporated into the peptides of the present invention.

In addition to chemical synthesis, the peptides of the present invention may be synthesized by employing recombinant DNA technology by expressing one or more polynucleotide comprising a peptide coding region. Thus, provided herein are isolated polynucleotides that encode the peptides of the present invention as well as recombinant vectors and host cells (both eukaryotic and prokaryotic) that have been genetically modified to express or overexpress the peptides of the present invention.

In one embodiment, the invention provides isolated polynucleotides comprising nucleotide sequences encoding the peptides of the invention.

Expression may be achieved in any conventional expression system known in the art by isolating a DNA fragment encoding the peptide of interest and cloning into an expression vector.

Useful compounds of the present invention are not limited to peptides incorporating natural and/or non-natural amino acids. The invention also encompasses various peptidomimetics such as, e.g., peptoids (a class of peptidomimetics whose side chains are appended to the nitrogen atom of the peptide backbone, rather than to the α-carbons). A number of non-peptide molecules having similar functional properties to the peptides of the invention can be developed to incorporate disparate chemical functional groups within a single molecule. These molecules are often referred to as scaffolding molecules, or scaffolds, since they can accommodate a wide range of chemical functionality and can be designed to present the chemical functional groups in a wide array of relative geometric orientations in space. Molecular scaffold systems include, but are not limited to, carbohydrates (see, e.g., Tamaruya et al., Angew Chem. Int. Ed. Engl., 2004, 43(21):2834-7), peptide nucleic acids (PNA's), (see, e.g., Peptide Nucleic Acids: Protocols and Applications, 2nd ed., Peter E. Nielsen, ed., Horizon Bioscience, 2004) and molecules not derived from biological precursors (see, e.g., Savinov and Austin, Org. Lett., 2002, 4(9):1419-22). The incorporation of this diverse a set of chemistries may require chemical protection of reactive functionality during synthesis. These techniques are well known in the art and can be found in references such as T. W. Green, P. G. M. Wuts, Protective Groups in Organic Synthesis, Wiley-Interscience, New York, 1999.

Peptides and their derivatives disclosed herein may be formulated as compositions together with a pharmaceutically acceptable carrier (such as an adjuvant or vehicle) and/or excipient, and/or diluents. Compositions of this invention may include pharmaceutically acceptable salts of the components therein. Pharmaceutically acceptable salts include the acid addition salts (formed with the free amino groups of the peptide) that are formed with inorganic acids such as, for example, hydrochloric or phosphoric acids, or such organic acids as acetic, tartaric, mandelic and the like. Salts formed with the free carboxyl groups can be derived from inorganic bases such as, for example, sodium, potassium, ammonium, calcium or ferric hydroxides, and such organic bases as isopropylamine, trimethylamine, 2-ethylamino ethanol, histidine, procaine and the like.

Pharmaceutically acceptable carriers are familiar to those skilled in the art and can include sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin. For compositions formulated as liquid solutions, acceptable carriers and diluents include saline and sterile water, and may optionally include antioxidants, buffers, bacteriostats, and other common additives. The compositions can also be formulated as pills, capsules, granules, or tablets which may contain, in addition to a peptide of this invention, diluents, dispersing and surface active agents, binders, and lubricants. Proper formulation is dependent upon the route of administration chosen.

The optimal therapeutically effective amount of a compound or composition of this invention may be determined experimentally, taking into consideration the exact mode of administration, the form in which the drug is administered, the indication toward which the administration is directed, the subject involved (e.g., body weight, health, age, sex, etc.), and the preference and experience of the physician or veterinarian in charge.

The efficacy of the peptides and compositions of this invention can be determined using the in vitro and in vivo assays described in the Examples section, below.

Following methodologies which are well-established in the art, effective doses and toxicity of the peptides and compositions of the present invention, which performed well in in vitro tests, can be determined in studies using small animal models (e.g., mice, rats or dogs) in which they have been found to be therapeutically effective and in which these drugs can be administered by the same route proposed for the human trials.

For any pharmaceutical composition used in the methods of the invention, dose-response curves derived from animal systems can be used to determine testing doses for administration to humans. In safety determinations for each composition, the dose and frequency of administration should meet or exceed those anticipated for use in any clinical trial.

As disclosed herein, the dose of the compound in the compositions of the present invention is determined to ensure that the dose administered continuously or intermittently will not exceed an amount determined after consideration of the results in test animals and the individual conditions of a patient. A specific dose naturally varies (and is ultimately decided according to the judgment of the practitioner and each patient's circumstances) depending on the dosage procedure, the conditions of a patient or a subject animal such as age, body weight, sex, sensitivity, feed, dosage period, drugs used in combination, seriousness of the disease, etc.

Toxicity and therapeutic efficacy of the compositions of the invention can be determined by standard pharmaceutical procedures in experimental animals, e.g., by determining the $LD_{50}$ (the dose lethal to 50% of the population) and the $ED_{50}$ (the dose therapeutically effective in 50% of the population). The dose ratio between therapeutic and toxic effects is the therapeutic index and it can be expressed as the ratio $ED_{50}/LD_{50}$.

All known peptide delivery methods can be used to deliver the peptides of the present invention to the target tissues. The specific type of delivery useful for a given peptide is determined by its specific size, flexibility, conformation, biochemical properties of constituent amino acids, and amino acid arrangement. Peptide composition also determines, in part, the degree of protein binding, enzymatic stability, cellular sequestration, uptake into non-target tissue, clearance rate, and affinity for protein carriers. Other aspects independent of peptide composition must also be considered, such as cerebral blood flow, diet, age, sex, species (for experimental studies), dosing route, and effects of existing pathological conditions.

The peptides and/or the pharmaceutical composition comprising the peptides of the invention can be administered to a subject (e.g., human or animal) in need via various administration routes, including, but not limited to, systemic administration, inhalation, topical, sublingual, oral, intranasal, and/or direct instillation (e.g, intratracheal instillation for lung treatment). Moreover, the peptides of the invention can be formulated for any suitable administration, with or without any pharmaceutically acceptable carrier, excipients, solvents, and/or solutions, and in certain proper dosage.

Examples of delivery methods useful for obtaining effective tissue delivery of the peptides of the invention (and effective passage through the blood-brain-barrier [BBB] in case of brain tissues), include, without limitation (reviewed, e.g., in Witt and Davis, AAPS Journal, 2006; 8(1): E76-E88.):
(i) invasive procedures (e.g., direct injection [e.g., using an external pump or i.v. line], transient osmotic opening, shunts, and biodegradable implants);
(ii) pharmacologically-based approaches to increase the tissue delivery by chemical modification of the peptide molecule itself, or by the attachment or encapsulation of the peptide in a substance that increases permeability, stability, bioavailability, and/or receptor affinity; in addition, modification of a peptide structure and/or addition of constituents (e.g., lipophilicity enhancers, polymers, antibodies) may enhance local peptide concentration in the target tissue;
(iii) physiologic-based strategies which exploit various carrier mechanisms; these strategies can be combined, dependent of the nature of a given peptide, creating "hybrid" peptides, resulting in synergistic delivery and end-effect.

Specific examples of peptide modifications and methods useful for improving delivery of the peptides of the invention include, without limitation, lipidization (e.g., methylation, dimethylation, or halogenation of constituent amino acids or acylation or alkylation of the N-terminal amino acid), structural modification to enhance stability (e.g., use of D-amino acids, N-acylation, or cyclization, e.g., via a disulfide-bridge or via a hydrazide bridge), glycosylation (e.g., adding simple sugars such as, e.g., glucose or xylose), increasing affinity for nutrient transporters (e.g., adding hexose or large neutral amino acid carriers which facilitate delivery of substrates to the brain), forming a prodrug by conjugating a peptide to a molecule with a known transporter activity or to a lipophilicity enhancer, which is cleaved at or near the site of action (e.g., using esterification [with, e.g., aromatic benzoyl esters or branched chain tertiary butyl esters] or amidation of amino, hydroxyl, or carboxylic acid-containing peptides; also, redox system-mediated delivery to the brain may be facilitated using conjugation to a methyldihydropyridine carrier and subsequent oxidation by NADH-linked dehydrogenases in the brain, which results in a quaternary ammonium salt, which does not cross back through the BBB endothelium), vector-based delivery (e.g., by coupling a peptide to a substance that increases the affinity to and transport across biological membranes via receptor-mediated or absorptive-mediated endocytosis followed by peptide release via enzymatic cleavage [e.g., conjugation of a peptide to murine monoclonal antibody (OX26) to the transferrin or conjugation to cationized albumin to increase brain uptake]), cationization to increase membrane entry via absorptive-mediated endocytosis, and polymer conjugation/encapsulation (e.g., conjugation to poly(ethylene glycol) [PEG] or poly(styrene maleic acid) or encapsulation via micro- or nano-particles [e.g., polymeric nanoparticles ranging in size between 10 and 1000 nm, which have a polysorbate overcoating such as, e.g., polysorbate-80], liposomes [e.g., surface-modified long-circulating liposomes grafted with a flexible hydrophilic polymer such as, e.g., PEG and/or liposomes composed of a phospholipid bilayer such as, e.g., pluronic copolymer P85, that act as a carrier for both hydrophilic and hydrophobic peptides], micelles [e.g., stable polymeric micelles prepared from amphiphilic PEG-phospholipid conjugates], or cell ghosts). Reviewed in Torchilin and Lukyanov, D D T, 2003, 8(6): 259-266; Egleton and Davis, NeuroRx, 2005, 2: 44-53; Witt and Davis, AAPS Journal, 2006; 8(1): E76-E88.

Regardless of the delivery method used, an important aspect of the present invention is to keep the size of the resulting delivered peptide sufficiently small (e.g., by using cleavable conjugates).

Oral Delivery. Contemplated for use herein are oral solid dosage forms, which are described generally in Remington's Pharmaceutical Sciences, 18th Ed. 1990 (Mack Publishing Co. Easton Pa. 18042) at Chapter 89, which is herein incorporated by reference. Solid dosage forms include tablets, capsules, pills, troches or lozenges, cachets, pellets, powders, or granules. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatized with various polymers (e.g., U.S. Pat. No. 5,013,556). A description of possible solid dosage forms for the therapeutic is given by Marshall, K. In: *Modern Pharmaceutics* Edited by G. S. Banker and C. T. Rhodes Chapter 10, 1979, herein incorporated by reference. In general, the formulation will include a peptide of the invention (or chemically modified forms thereof) and inert ingredients which allow for protection against the stomach environment, and release of the biologically active material in the intestine.

Also contemplated for use herein are liquid dosage forms for oral administration, including pharmaceutically acceptable emulsions, solutions, suspensions, and syrups, which may contain other components including inert diluents; adjuvants such as wetting agents, emulsifying and suspending agents; and sweetening, flavoring, and perfuming agents.

As discussed above, the peptides may be chemically modified so that oral delivery of the derivative is efficacious. Generally, the chemical modification contemplated is the attachment of at least one moiety to the component molecule itself, where said moiety permits (a) increase in peptide stability (e.g., by inhibition of proteolysis) and (b) efficient uptake into the blood stream from the stomach or intestine. As discussed above, common delivery-improving peptide modifications include PEGylation or the addition of moieties such as propylene glycol, copolymers of ethylene glycol and propylene glycol, carboxymethyl cellulose, dextran, polyvinyl alcohol, polyvinyl pyrrolidone, polyproline, poly-1,3-dioxolane and poly-1,3,6-tioxocane (see, e.g., Abuchowski and Davis (1981) "Soluble Polymer-Enzyme Adducts," in Enzymes as Drugs. Hocenberg and Roberts, eds. (Wiley-Interscience: New York, N.Y.) pp. 367-383; and Newmark, et al. (1982) J. Appl. Biochem. 4:185-189).

For oral formulations, the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the peptide (or derivative) or by release of the peptide (or derivative) beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic (i.e. powder), for liquid forms a soft gelatin shell may be used. The shell material of cachets could be thick starch or other edible paper. For pills, lozenges, molded tablets or tablet triturates, moist massing techniques can be used.

The peptide (or derivative) can be included in the formulation as fine multiparticulates in the form of granules or pellets of particle size about 1 mm. The formulation of the material for capsule administration could also be as a powder, lightly compressed plugs, or even as tablets. These therapeutics could be prepared by compression.

Colorants and/or flavoring agents may also be included. For example, the peptide (or derivative) may be formulated (such as by liposome or microsphere encapsulation) and then further contained within an edible product, such as a refrigerated beverage containing colorants and flavoring agents.

One may dilute or increase the volume of the peptide (or derivative) with an inert material. These diluents could include carbohydrates, especially mannitol, lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress, and Avicel.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. The disintegrants may also be insoluble cationic exchange resins. Powdered gums may be used as disintegrants and as binders. and can include powdered gums such as agar, Karaya or tragacanth. Alginic acid and its sodium salt are also useful as disintegrants.

Binders may be used to hold the peptide (or derivative) agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the peptide (or derivative).

An antifrictional agent may be included in the formulation of the peptide (or derivative) to prevent sticking during the formulation process. Lubricants may be used as a layer between the peptide (or derivative) and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the peptide (or derivative) into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 20, 40, 60, 65 and 80, sucrose fatty acid ester, methyl cellulose and carboxymethyl cellulose. These surfactants could be present in the formulation of the protein or derivative either alone or as a mixture in different ratios.

Additives which potentially enhance uptake of the peptide (or derivative) are for instance the fatty acids oleic acid, linoleic acid and linolenic acid.

Controlled release oral formulations may be desirable. The peptide (or derivative) could be incorporated into an inert matrix which permits release by either diffusion or leaching mechanisms, e.g., gums. Slowly degenerating matrices may also be incorporated into the formulation. Some enteric coatings also have a delayed release effect. Another form of a controlled release is by a method based on the Oros therapeutic system (Alza Corp.), i.e. the drug is enclosed in a semipermeable membrane which allows water to enter and push drug out through a single small opening due to osmotic effects.

Other coatings may be used for the formulation. These include a variety of sugars which could be applied in a coating pan. The peptide (or derivative) could also be given in a film coated tablet and the materials used in this instance are divided into 2 groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxy-methyl cellulose, providone and the polyethylene glycols. The second group consists of the enteric materials that are commonly esters of phthalic acid.

A mix of materials might be used to provide the optimum film coating. Film coating may be carried out in a pan coater or in a fluidized bed or by compression coating.

Parenteral Delivery. Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Administration by Inhalation and Intranasal Administration. The present invention encompasses any delivery device that is suitable for administration by inhalation or intranasal administration of the compositions of the invention. Preferably, such means administers a metered dosage of the composition. The composition of the present invention may be packed in any appropriate form or container as long as a means is provided to deliver the composition to the oral or lung or nasal mucosa. Non-limiting examples of useful delivery devices include, e.g., instillation catheters, droppers, unit-dose containers, squeeze bottles pump sprays, airless and preservative-fee sprays, compressed air nebulizers, metered-dose inhalers, insufflators and pressurized metered dose inhalers. For administration of a liquid in drop form, compositions of the invention can be placed in a container provided with a conventional dropper/closure device, e.g. comprising a pipette or the like, preferably delivering a substantially fixed volume of composition/drop. For administration of an aqueous solution as a spray, the aqueous solution may be dispensed in spray form by a variety of methods known to those skilled in the art. For example, such compositions will be put up in an appropriate atomising device, e.g. in a pump-atomiser, or the like. The atomising device will be provided with appropriate means, such as a spray adaptor for delivery of the aqueous spray to the naris. Preferably it will be provided with means ensuring delivery of a substantially fixed volume of composition/actuation (i.e. per spray-unit). Examples of nasal sprays include nasal actuators produced by Ing. Erich Pfeiffer GmbH, Radolfzell, Germany (see U.S. Pat. Nos. 4,511,069, 4,778,810, 5,203,840, 5,860,567, 5,893,484, 6,227,415, and 6,364,166. Additional aerosol delivery forms may include, e.g., compressed air-, jet-, ultrasonic-, and piezoelectric nebulizers. Alternatively the spray may be bottled under pressure in an aerosol device. The propellant may be a gas or a liquid (e.g. a fluorinated and/or chlorinated hydrocarbon). The spray composition may be suspended or dissolved in a liquid propellant. Stabilizing and/or suspending agents and/or co-solvents may be present. A dry powder may be readily dispersed in an inhalation device as described in U.S. Pat. No. 6,514,496 and Garcia-Arieta et al., Biol. Pharm. Bull. 2001; 24: 1411-1416. If desired a powder or liquid may be filled into a soft or hard capsule or in a single dose device adapted for nasal administration. The powder may be sieved before filled into the capsules such as gelatine capsules. The delivery device may have means to break open the capsule. The powdery nasal composition can be directly used as a powder for a unit dosage form. The contents of the capsule or single dose device may be administered using e.g. an insufflator. Preferably it will be provided with means ensuring dosing of a substantially fixed amount of composition.

In another embodiment, the composition of the invention can be provided as a nasal insert having the peptide(s) of the invention. The insert may be retained in the naris, but flushed by the nasal mucus, and may be designed to release the Peptide, fragment or derivative of the invention at the same place in the naris. Suitable nasal insert types include nasal plugs, tampons and the like. Further examples of nasal inserts, their characteristics and preparation are described in EP 490806.

Delivery devices are important not only for delivering the peptides of the invention, but also for providing an appropriate environment for storage. This would include protection from microbial contamination and chemical degradation. The device and formulation should be compatible so as to avoid potential leaching or adsorption. The delivery device (or its packaging) can be optionally provided with a label and/or with instructions for use.

The peptides of the invention can be administered using any standard administration route and technique known in the art. The peptides can also be delivered using a vector (such as a viral vector) with the ability to express a peptide of this invention.

Therapeutic Applications of the Peptides of the Invention

Fibrotic diseases that could be targeted by the peptides of invention include, but not limited to, liver diseases, including but not limited to, liver cirrhosis and fibrosis of any etiology (alcoholic; non-alcoholic steato-hepatitis; autoimmune hepatitis; chronic hepatitis C; chronic hepatitis B; primary biliary cirrhosis; secondary biliary cirrhosis; sclerosing cholangitis; alpha-1-antitrypsin deficiency; Wilson's disease; biliary atresia); lung diseases, including but not limited to, idiopathic pulmonary fibrosis; radiation-induced pneumonitis; chronic obstructive pulmonary disease; emphysema; secondary to chronic infections and inflammation; kidney diseases, including but not limited to, glomerulonephritis and interstitial-tubular fibrosis; skin diseases, including but not limited to, secondary to burns; keloids; hypertrophic post-surgical wounds; scleroderma; esophageal-gastro-intestinal, including but not limited to, secondary to corrosive materials; secondary to inflammatory diseases (inflammatory bowel diseases; esophageal injury and inflammation); secondary to ischemic disease; peritoneal fibrosis; pancreatic fibrosis; post-radiation; cardiac-vascular diseases secondary to infarcts; brain diseases secondary to ischemia/infarcts; post-trauma; and musculoskeletal diseases, including but not limited to, posttraumatic muscular fibrosis and synovial/joint fibrosis.

Inflammatory diseases that could be targeted by the peptides of invention include, but not limited to, liver diseases, including but not limited to, liver inflammation diseases including but not limited to, alcoholic liver disease; non-alcoholic steato-hepatitis; autoimmune hepatitis; chronic hepatitis C; chronic hepatitis B; primary biliary cirrhosis; secondary biliary cirrhosis; sclerosing cholangitis; alpha-1-antitrypsin deficiency; Wilson's disease; biliary atresia; lung inflammation associated with Idiopathic pulmonary fibrosis; radiation-induced pneumonitis; chronic obstructive pulmonary disease; emphysema; secondary to chronic infections and inflammation; kidney inflammation associated with glomerulonephritis; interstitial-tubular fibrosis; skin inflammation secondary to burns; scleroderma; psoriasis; esophageal-gastro-Intestinal secondary to inflammatory diseases (Inflammatory bowel diseases; esophageal injury and inflammation); post-radiation; Inflammatory cardiomyopathy; brain inflammation (post-trauma; Alzheimer disease; encephalitis; meningitis); musculoskeletal inflammation due to myositis and arthritis.

Peptides of the invention can be used as part of combination treatments with various other treatments known for the specific diseases which are being targeted.

The Therapeutic Target and its Potential Clinical Relevance for Liver Fibrosis

Activation of liver myofibroblasts (of different origins) is responsible for the development of liver fibrosis in chronic liver diseases (13; 15; 19; 20), and remarkably, the clearance of myofibroblasts by apoptosis would allow recovery from liver injury and reversal of liver fibrosis (7; 20; 24). There is agreement among liver experts that inhibiting or reversing myofibroblastic activation of different cellular origins is critical for the treatment of liver fibrosis (7; 15; 19; 20; 24). Finally, blocking the progression of liver fibrosis would decrease development of primary liver cancer since the majority of hepatocellular carcinomas arise in cirrhotic livers (34).

The rationales for developing the therapeutic peptides of the invention are provided as follows: a) activation of myofibroblasts is responsible for the development of liver fibrosis in chronic liver diseases of all causes (13; 15; 19; 20); b) inhibition of myofibroblastic activity by apoptosis would allow recovery from liver injury and potentially reversal of liver fibrosis (7; 20; 24); c) phosphorylated C/EBPβ-Thr217 is indispensable for the survival of activated liver myofibroblasts by binding to the inactive pro-caspase 8 complex and preventing its self-cleavage and activation (4); d) phosphorylation of C/EBPβ-Thr217 in activated liver myofibroblasts is important for the progression of liver fibrosis. This was determined using classical human hepatotoxin-induced liver injury and fibrosis models in mice (15; 24; 38), and primary mouse and human liver myofibroblasts (4; 6; 7; 23; 27); e) phosphorylation of C/EBPβ-Thr217 in activated liver myofibroblasts is also important in other animal models that mimic other causes of human liver injury-fibrosis (acute Fas- and chronic dimethylnitrosamine-induced liver injury and fibrogenesis); f) phosphorylation of human C/EBPβ-Thr266 (the homologous human phosphoacceptor) in activated liver myofibroblasts also occurs in human liver fibrosis (7) and in activated primary human myofibroblasts in culture (7); g) Mice expressing the non-phosphorylatable C/EBPβ-Ala217 transgene are refractory to the induction of myofibroblasts' activation and proliferation by different hepatotoxins (4; 7); h) the non-phosphorylatable C/EBPβ-Ala217 is present within the death receptor complex II, with active caspase 8, and is linked to apoptosis of activated liver myofibroblasts in transgenic mice (4; 7; 9); i) blocking phosphorylation of C/EBPβ-Thr217 with the C/EBPβ-Ala217 transgene or by C/EBPβ gene knock-out decreases the fibrotic response of the liver to acute and chronic injury (4; 7); j) the decreased fibrotic response of the liver to hepatotoxins in C/EBPβ-ko mice suggests that the important target of RSK phosphorylation in activated liver myofibroblasts is C/EBPβ-Thr217 rather than other phosphoacceptors in c-Fos, CREB, CBP or other proteins (4; 44; 45; 46; 52); k) the peptide prevents the phosphorylation of C/EBPβ-Thr217 (the molecular target) in myofibroblasts activated in culture by a collagen type 1 matrix or by liver injury in mice (4); and l) the therapeutic lead and two alternate peptides stimulate apoptosis of liver myofibroblasts following their activation in culture by a collagen type 1 matrix or by liver injury in mice and block active fibrogenesis, preventing progression and inducing regression of liver fibrosis; m) the peptides stimulates apoptosis of activated liver myofibroblasts and reversal of fibrosis in a chronic animal model of cirrhosis (7); and n) the therapeutic lead compound also has very high efficacy against the molecular target, preventing activation of myofibroblasts and inhibiting liver fibrosis.

The Therapeutic Target and its Potential Clinical Relevance for Liver Inflammation Activation of liver macrophages (of different origins) is responsible for the development of liver inflammation in acute and chronic liver diseases. Excessive liver injury and inflammation associated with liver diseases induced by viral, toxic, immunologic, and metabolic diseases (13), results in liver dysfunction and in chronic conditions in the potential deposition of scar tissue and the development of cirrhosis (15). Amplification of liver injury can be mediated by macrophages (14, 40).

Expression of genes required for Inflammasome activation is indispensable for macrophage activation and Inflammasome function. C/EBPβ appears to be an important signaling molecule for macrophages because its expression is dramatically increased during differentiation of these cells, and it is induced by macrophage modulators (LPS, IL-1, G-CSF, TGFβ, vitamin D, retinoic acid) (Akira et al., 1990) {Friedman, 2007 2075/id}. Upon activation and differentiation of macrophages, C/EBPβ can regulate the expression of inflammatory cytokines and chemokines, which are linked to the Inflammasome activation {Friedman, 2007 2075/id}. In addition, expression of a dominant inhibitor of C/EBP DNA-binding sites {Iwama, 2002 2077/id} or a targeted deletion of C/EBPβ results in impaired macrophage differentiation {Sebastian, 2006 2079/id}.

Phosphorylation of the CCAAT/Enhancer Binding Protein (C/EBP)-3 by ribosomal S-kinase (RSK), which is activated directly by extracellular-regulated kinase (ERK)-1/2 phosphorylation, plays an essential role in the ERK/Mitogen Activated Protein Kinase (MAPK) signaling pathway regulating cell survival (Buck et al., Mol Cell 4:1087, 1999; Buck et al., Mol Cell 8: 807-16, 2001; Buck and Chojkier, PLOS One 2: e1372, 2007). Expression of the phosphorylation-mutant C/EBPβ-Glu217, which mimics phosphorylated C/EBPβ-Thr217 in biological assays (Trautwein et al., Nature 364: 544-547, 1993), was sufficient to rescue macrophage injury induced by Anthrax lethal toxin (Buck and Chojkier, Am J Physiol Cell Physiol 293: C1788-96, 2007).

The Therapeutic Target and its Potential Clinical Relevance for Lung Inflammation and Fibrosis Activation of LMF is responsible for the development of lung fibrosis in IPF (11; 14; 15). Phosphorylated C/EBPβ-Thr217 facilitates survival of activated LMF by binding to the inactive procaspase 8 complex and preventing its self-cleavage and activation (6). Phosphorylation of C/EBPβ-Thr217 in activated LMF is critical for the progression of lung fibrosis. This was determined by using classical Bleomycin-induced lung fibrosis models in mice, primary mouse and human LMF in tissue culture and cell-free systems (5; 6). Phosphorylation of human C/EBPβ-Thr266 in activated LMF occurs in human lung fibrosis of IPF (5). Mice expressing the non-phosphorylatable C/EBPβ-Ala217 transgene are refractory to the induction of LMF activation and proliferation by Bleomycin (5). The non-phosphorylatable C/EBPβ-Ala217 facilitates the death of activated LMF by binding to the inactive procaspase and inducing its self-cleavage and activation (5). The non-phosphorylatable C/EBPβ-Ala217 dominant negative transgene was present within the death receptor complex II, with active caspase 8, and was linked to apoptosis of activated LMF in transgenic mice (3; 5; 6). Blocking phosphorylation of C/EBPβ-Thr217 with the C/EBPβ-Ala217 transgene or by C/EBPβ gene knock-out decreases the fibrotic response of the lung (5; 25). The decreased fibrotic response of the lung to Bleomycin in C/EBPβ-ko mice (25) suggests that the important target of RSK in activated LMF is C/EBPβ-Thr217 rather than other RSK phosphoacceptors on c-Fos, CREB, CBP or other proteins. The inhibitory parent peptide prevents the phosphorylation of C/EBPβ-Thr217 in LMF activated in culture by a collagen type 1 matrix or in vivo by lung injury (5).

Synthesis and analysis of therapeutic peptides of the invention containing non-naturally occurring amino acids with and without an N-terminal PEG-30 kDa are provided in the following Amino acid sequences of these peptides are provided below:

| Sequence |
|---|
| TAGGGTGTGTTTAGGCGAAA (SEQ ID NO: 1) |
| TCTGTTGCCTTCCTAATAAG (SEQ ID NO: 2) |

| Sequence |
|---|
| Lys-DAla-DVal-Asp-NH2 |
| Ac-Lys-DAla-DVal-Asp-NH2 |
| Mpr-Lys-DAla-DVal-Asp-NH2 |
| PEG-Lys-DAla-DVal-Asp-NH2 |
| PEG-Mpr-Lys-DAla-DVal-Asp-NH2 |
| Lys-DAla-Val-Asp-NH2 |
| Ac-Lys-DAla-Val-Asp-NH2 |
| Mpr-Lys-DAla-Val-Asp-NH2 |
| PEG-Lys-DAla-Val-Asp-NH2 |
| PEG-Mpr-Lys-DAla-Val-Asp-NH2 |
| Lys-Ala-DVal-Asp-NH2 |
| Ac-Lys-Ala-DVal-Asp-NH2 |
| Mpr-Lys-Ala-DVal-Asp-NH2 |
| PEG-Lys-Ala-DVal-Asp-NH2 |
| PEG-Mpr-Lys-Ala-DVal-Asp-NH2 |
| Ac-Lys-Ala-Val-Asp-NH2 (SEQ ID NO: 6) |
| Ac-Lys-Ala-Val-Lys-CHO (SEQ ID NO: 7) |
| DLys-Ala-DVal-Asp-NH2 |
| DLys-Ala-Val-DAsp-NH2 |
| Lys-Ser-Lys-Ala-Lys-Lys-Ala-Val-Asp-Lys-His-Ser-Asp (SEQ ID NO: 3) |
| Lys-Ala-Lys-Lys-Ala-Val-Asp-Lys-His-Ser (SEQ ID NO: 4) |
| Ala-Lys-Lys-Ala-Val-Asp-Lys-His (SEQ ID NO: 5) | acid linker(Ac); Mercaptopropionic acid linker (Mpr); D-amino acid

TABLE 1

THERAPEUTIC PEPTIDES FOR THE TREATMENT OF LIVER FIBROSIS
(Efficacy and Safety)

| PEPTIDE | Mouse Activated Liver Myofibroblasts Death Cell (%) [20 ng/ml] | Human Activated Liver Myofibroblasts Death Cell (%) | Hepatocyte Toxicity [20 ng/ml] | Mouse Toxicity (in vivo) | Efficacy [culture/mice] |
|---|---|---|---|---|---|
| Parent peptide Ac-Lys-Ala-Val-Asp-NH2 (SEQ ID NO: 6) | 89.5 | 80.9 | No toxicity found when tested in primary mouse and human hepatocytes | No: 20 mg/kg | Excellent in human/mice Activated Myofibroblasts and in mouse models of liver fibrosis |
| Lead therapeutic peptide) Peg-30kDa-Lys DAla-DVal-Asp-NH2 | 90.5 | 86.2 | No toxicity found when tested in primary mouse and human hepatocytes | No: 20 mg/kg | Excellent in human/mice Activated Myofibroblasts and in mouse models of liver fibrosis |

TABLE 1-continued

THERAPEUTIC PEPTIDES FOR THE TREATMENT OF LIVER FIBROSIS
(Efficacy and Safety)

| PEPTIDE | Mouse Activated Liver Myofibroblasts Death Cell (%) [20 ng/ml] | Human Activated Liver Myofibroblasts Death Cell (%) | Hepatocyte Toxicity [20 ng/ml] | Mouse Toxicity (in vivo) | Efficacy [culture/mice] |
|---|---|---|---|---|---|
| Alternate therapeutic peptide 1 Peg-30kDa-Lys-DAla-Val-Asp-NH2 | 79.9 | 67.9 | No toxicity found when tested in primary mouse and human hepatocytes | No: 20 mg/kg | Excellent in human/mice Activated Myofibroblasts and in mouse models of liver fibrosis |
| Alternate therapeutic peptide 2 Peg-30kDa-Lys-Ala-DVal-Asp-NH2 | 57.1 | 72.3 | No toxicity found when tested in primary mouse and human hepatocytes | No: 20 mg/kg | Excellent in human Activated Myofibroblasts and in mouse models of liver fibrosis |
| *DLys-Ala-DVal-Asp-NH2 | N/A | 30.6 | N/A | N/A | N/A |
| *DLys-Ala-Val-DAsp-NH2 | N/A | 44.0 | N/A | N/A | N/A |

The parent peptide was developed based on the discovery of an important downstream specific MAPK pathway phosphorylation of C/EBPβ-Thr217. Thus, the target, being the last step in an extensive signaling network could be blocked with fewer side effects. Indeed, mice expressing the dominant negative, full-length C/EBPβ-Ala217 have a normal phenotype and are fertile.

The invention provides efficacy and safety of the therapeutic peptides. In certain embodiments, the invention provides that the three selected PEG-peptides were very effective in preventing the activation of primary human and mouse liver myofibroblasts in culture (see Table 1). Their efficacy was comparable to that of the parent peptide. Neither the parent peptide nor any of the three selected peptides induced hepatocyte injury to human or mouse cultured primary hepatocytes or to mice in vivo (at 100-fold the therapeutic dose) (Table 1).

Although no toxicity issues have been observed in mice with the parent compound, related peptides were developed using analog synthesis to improve the predictable pitfalls of potential immunogenicity, short half-life and limited bioavailability in humans (29; 39; 42). Multiple substitutions of amino acids were generated via analog synthesis after making a library based on the parent peptide (all 56 of 76 peptides that could be synthesized were tested). The selected PEG-peptides of the invention were the result of in vitro testing of all of the compounds within this library.

Assays were used in a step-wise manner to select the safest and most efficient peptides (including apoptosis assays in activated primary human liver myofibroblasts; cell-free caspase 8 activation assays; acute liver injury/fibrogenesis models; toxicology assays in highly differentiated, primary human hepatocyte cultures and in mice).

The invention is also described and demonstrated by way of the following examples. However, the use of these and other examples anywhere in the specification is illustrative only and in no way limits the scope and meaning of the invention or of any exemplified term. Likewise, the invention is not limited to any particular embodiments described here. Indeed, many modifications and variations of the invention may be apparent to those skilled in the art upon reading this specification, and such variations can be made without departing from the invention in spirit or in scope. It is, therefore, intended that the invention is to be limited only by the terms of the appended claims which cover all and full scope of such equivalent variations as fall within the true spirit and scope of the invention.

Throughout the specification various citations are referenced, and the entire content of each is hereby incorporated by reference. The following example is provided to describe the invention in more detail. It is intended to illustrate, not to limit the invention.

EXAMPLE 1

Pilot Studies of In Vivo Efficacy and Safety of the Lead Therapeutic PEG-30 kDa-peptide in Acute Liver Injury and Activation of Liver Myofibroblasts To induce acute liver injury, a single dose of the human hepatotoxin Carbon Tetrachloride (CCl4) was administered to normal mice (4). Eight hours later, animals received an IP injection of the lead therapeutic PEG-30 kDa-peptide (5 μg of the peptide linked [peptide to PEG at 1:60] to the PEG-30 kDa). Animals were sacrificed after 30 hr, at the peak of hepatocyte death as measured by ALT (a clinical end-point used routinely in clinical practice and by the FDA in the evaluation of liver toxicity in human drug studies) (16). Mice receiving only CCl4 had intense expression of α-SMA in the liver, a main indicator of activated liver myofibroblasts (4;7), compared with the minor expression in mice receiving both CCl4 and the lead therapeutic PEG-peptide. There was severe acute liver injury in animals receiving CCl4 but mild-to-moderate injury in animals receiving both CCl4 and the lead therapeutic compound (FIG. 1).

The therapeutic lead PEG peptide blocked the typical liver discoloration and granular appearance of severe liver injury induced by the hepatotoxin CCl4 and the livers of these treated mice were similar to control livers (FIG. 1). The histopathology induced by CCl4 was one of severe liver injury and collapse of the architecture as reflected by the standard clinical stains (H&E and Reticulin) (FIG. 1).

The lead PEG-30 kDa-peptide decreased the acute liver injury (FIG. 1). The serum ALT was markedly induced by the hepatotoxin CCl4 (10,554+/−867 IU/dL) but improved in spite of only a single treatment of the therapeutic lead peptide, 8 hr after the injury was established (6,754+/−905 IU/dL). The albumin mRNA (the major indicator of normal liver-specific gene expression) (14) was decreased by 16 fold and the IL-6 and TNF-α mRNAs (the main indicators of liver inflammation) were increased by 3- and 85-fold, respectively by CCl4 from control values. The therapeutic lead PEG peptide markedly improved these values (albumin mRNA: decreased only 2 fold, IL-6 mRNA was normal, and TNF-α was only 4 fold increased from control values).

The other two alternative PEG Peptide 1 and Peptide 2 performed similarly to the lead PEG peptide in minimizing acute liver injury and activation of myofibroblasts. Thus, the early safety profile of the therapeutic peptides is very high in an acute mouse model of liver injury and activation of liver myofibroblasts.

EXAMPLE 2

Figure 2A:
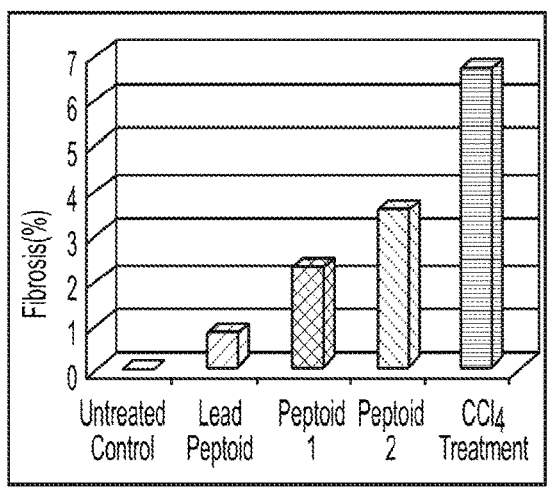
FIGS. 2A-2B. High efficacy of the therapeutic PEG-30 kDa-peptides in a chronic mouse model of liver fibrosis. All groups of mice (except control) received CCl4 administration for 16-wk (n=6/group). The CCl4 treatment group received only the hepatotoxin, while the other groups also received the indicated therapeutic PEG-30 kDa-peptide (7 µg of peptide linked to 420 µg PEG-30 kDa once a week) starting at week-8.
Figure 2B:
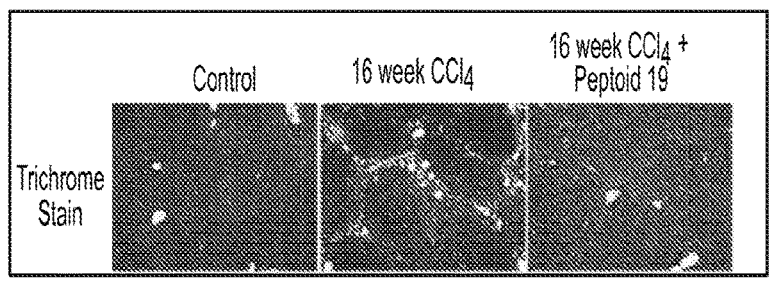

High Efficacy of the Lead Therapeutic Peptide in a Chronic Mouse Model of Liver Fibrosis The therapeutic lead PEG-peptides underwent a systematic analysis of efficacy and safety in a classical chronic liver fibrosis model (7; 15; 24; 38). CCl4 (a human hepatotoxin) was administered to mice for 16-wk as a classical model of liver fibrosis (7). The three selected therapeutic PEG-peptides were administered once a week IP (7 μg of peptide linked to PEG) starting at week 8, once severe liver fibrosis was already established. The efficacy of the three selected PEG peptides included quantitative analysis of liver fibrosis (7). CCl4 administration to mice for 16-wk induced liver cirrhosis (FIGS. 2A and 2B). It was found that the lead PEG-30 kDa peptide (given once per week from week-8, once the liver fibrosis was already severe) decreased liver fibrosis by >8-fold. The other two PEG-30 kDa peptides 1 and 2, also effectively decreased liver fibrosis (~3-fold and ~2-fold, respectively) (FIG. 2A). This mimics the treatment given for several years to a patient with established severe liver fibrosis.

Thus, this example provides that the lead therapeutic peptide having the amino acid sequence of Ac-Lys-D-Ala-D-Val-Asp-NH2 was highly effective in preventing progression and inducing regression of liver fibrosis after cirrhosis was established after administration of CCl$_4$ for 8 weeks. The Ac-Lys-D-Ala-D-Val-Asp-NH2 was administered IP (7 μg of peptide linked to PEG-30 kDa) once/week for an additional 4 or 8 weeks. The CCl$_4$ administration continued for 4 or 8 weeks. The Ac-Lys-D-Ala-D-Val-Asp-NH2 peptide inhibited liver fibrosis by 8-fold.

In contrast, after cirrhosis was established on week-8, treatment with the parent peptide having the amino acid sequence of Ac-Lys-Ala-Val-Lys-CHO (SEQ ID NO: 7) that does not contain any D-amino acid for an additional 4 or 8 weeks (5 μg IP, three times/week and for week 9, followed by 1 μg IP, three times/week for weeks 10-12 or 10-16), while continuing to induce liver injury and fibrosis with CCl$_4$. The parent peptide inhibited liver fibrosis by only 2 to 3-fold.

EXAMPLE 3

Figure 3:
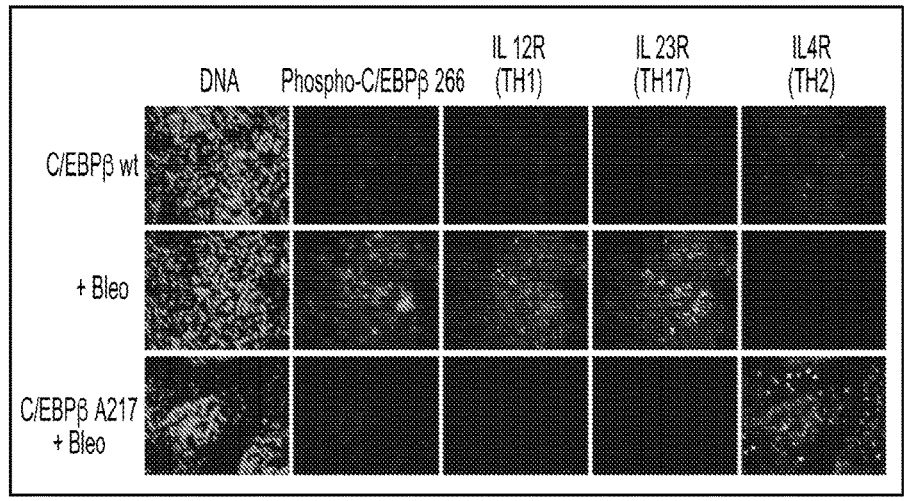
FIG. 3. Phosphorylation of C/EBPβ-Thr$^{217}$ was induced and necessary for the Th1/Th17 response to Bleomycin. Lung inflammation was induced in C/EBPβ$^{wt}$ mice treated with Bleomycin for 7 days. Purified lung T-cells (CD-4+); Phospho-C/EBPβThr217; L-12Rβ; IL-23R; and IL-4Rα were identified as described in Table 2 & FIG. 5. C/EBPβ-Ala217 mice blocks phosphorylated C/EBPβ-Thr217 in T-cells and were refractory to the induction of the Th1/Th2 phenotype with Bleomycin. In C/EBPβ-Ala217 mice, Bleomycin induced T-cell expression of IL-4Rα (a Th2 phenotype).
Figure 4:
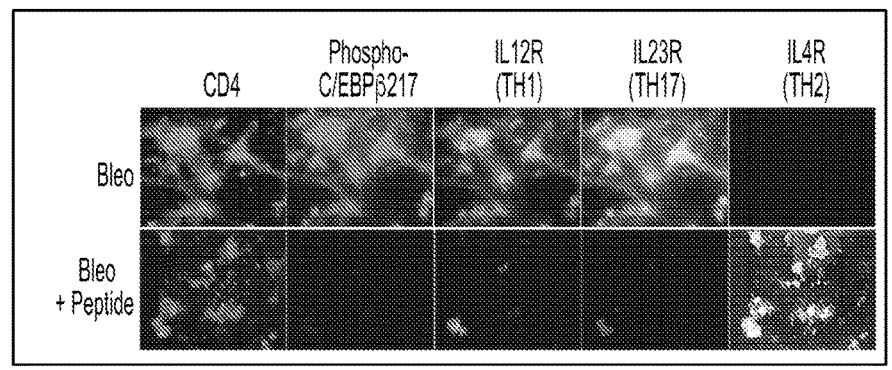
FIG. 4. Phosphorylation of C/EBPβ-Thr$^{217}$ was induced and necessary for the Th1/Th17 response to Bleomycin. Lung inflammation was induced in C/EBPβ$^{wt}$ mice treated with Bleomycin for 7 days. Purified lung T-cells (CD-4+−); Phospho-C/EBPβThr217; L-12Rβ; IL-23R; and IL-4Rα were identified as described Table 2 & FIG. 5. The C/EBPβ peptide blocks phosphorylated C/EBPβ-Thr217 in T-cells, the Th1/Th17 phenotype and induces T-cell expression of IL-4Rα (a Th2 phenotype)

Phosphorylation of C/EBPβ on Thr217 in Mouse T-cells is Induced and Associated with the Inflammatory Th1/Th17 a Treatment—Inhibitory Effects of the C/EBPβ Peptide The results supporting that phosphorylation of mouse C/EBPβ on Thr217 confers the Th1/Th17 phenotype have been obtained using freshly isolated, CD-4+ mouse lung T-cells. On day-7 after Bleomycin treatment, the purified lung T-cells from C/EBPβ-wt mice expressed the IL-12R3 (a Th1 phenotype) or the IL-23R (a Th17 phenotype) and phosphorylation of endogenous C/EBPβ on Thr217 (detected using specific antibodies that were developed against this epitope) (FIGS. 3 & 4). Treatment of C/EBPβ-Ala217 mice with Bleomycin (FIG. 3) or treatment of C/EBPβ-wt mice with Bleomycin and the C/EBPβ peptide blocks phosphorylated C/EBPβ-Thr217 and the Th1/Th17 phenotype and induces T-cell expression of IL-4Rα (a Th2 phenotype) (FIG. 4).

EXAMPLE 4

Figure 5:
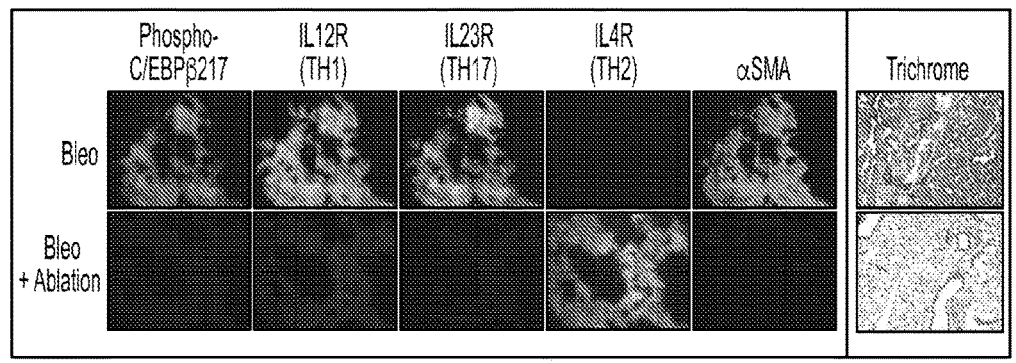
FIG. 5. Th1/Th17 cells were induced and associated with the activation of lung myofibroblasts in response to Bleomycin treatment. Evidences from M1 macrophage ablation experiments. On day-7 after Bleomycin treatment, the purified CD4+ mouse lung T-cells expressed IL-12R or IL-23R (a Th1/Th17 phenotype) and αSMA (activated myofibroblasts). When mice received Bleomycin and Clodronate (a blocker of ATP production) liposomes (intracheally and IP) there was a preferential ablation of phagocytic M1 macrophages on day-7 (undetectable TNFαR2) and of Th1 (IL-12R-red)/Th17 (IL-23R-green) cells with induction of IL-4Rα (aqua) (a Th2 phenotype) and markedly reduced αSMA (activated myofibroblasts) (magenta). Blockade of Th1/Th17 cells through M1 macrophage ablation for 21-days markedly inhibited Bleomycin-induced lung fibrosis (Trichrome), suggesting that the Th1/Th17 phenotype but not the Th2 phenotype is responsible for this effect.

Th1/Th17 Cells are Induced and Associated with the Activation of Lung Myofibroblasts in Response to Bleomycin Treatment—Evidences from M1 Macrophage Ablation Experiments On day-7 after Bleomycin treatment, the purified CD4+ mouse lung T-cells expressed IL-12R or IL-23R (a Th1/Th17 phenotype) and αSMA (activated myofibroblasts). When mice received Bleomycin and Clodronate (a blocker of ATP production) liposomes (intracheally and IP) there was a preferential ablation of phagocytic M1 macrophages on day-7 (undetectable TNFαR2) and of Th1 (IL-12R)/Th17 (IL-23R) cells with induction of L-4Rα (a Th2 phenotype) and markedly reduced αSMA (activated myofibroblasts) (FIG. 5). Blockade of Th1/Th17 cells through M1 macrophage ablation (a confounding factor) for 21-days markedly inhibited Bleomycin-induced lung fibrosis (FIG. 5, Trichrome), suggesting that the Th1/Th17 (M1) phenotype but not the Th2 phenotype is responsible for this effect.

EXAMPLE 5

Figure 6:
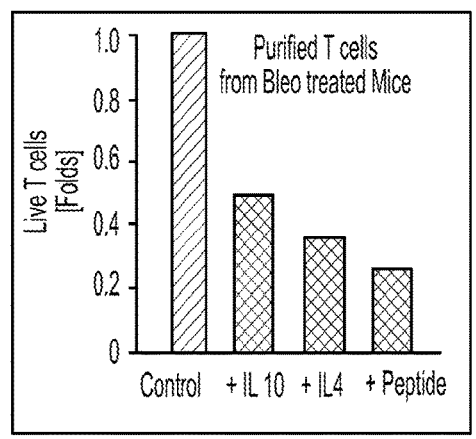
FIG. 6. Th2 stimuli and the C/EBPβ peptide induce apoptosis of isolated primary mouse lung Th1 and Th17 cells from Bleomycin-treated animals. T-cells were isolated by CD-4+ affinity and treated for 6 hr with 10 µg/ml of IL-10 or IL-4, or with 100 pM C/EBPβ peptide. Apoptosis was detected as described (12). The Th2 inducers and the C/EBPβ peptide (P<0.05) stimulated ex vivo apoptosis of Th-1 and Th-17 lung cells.

Isolation and Purification of T-cells from Bleomycin-treated Mice and their Ex Vivo Inhibition by the C/EBPβ Peptide and Th2 Inducers Approximately, 5 million CD4+ T-cells were isolated and purified from 165 mg of C/EBPβ-wt mouse lung on day-7 after Bleomycin treatment using specific antibodies against surface receptors. Greater than 95% of the T-cells were Th1 or Th17. These Th1/Th17-cells were treated ex vivo for 4 hr with 10 μg/ml of IL-4, IL-10 (Th2 inducers) or 100 pM C/EBPβ peptide (an inhibitor of C/EBPβ-Thr217 phosphorylation). The treatment by the Th2 inducers or C/EBPβ peptide stimulated >50% apoptosis, suggesting that this is a plausible mechanism by which inhibition of C/EBPβ-Thr217 phosphorylation blocks Th1/Th17 induction. This effect is congruent with the report of the protein/protein interaction between phosphorylated C/EBPβ-Thr217/procaspase-8 and the inhibition of procaspe-8 cleavage and self-activation by the XEVD caspase inhibitory box created by the Thr-217 phosphorylation in C/EBPβ (12). The stimulation of apoptosis of Th1/Th17 cells by Th2 inducers was unexpected (suggesting an up-regulation of IL-4 and IL-10 signaling pathways) and offers an exciting tool to analyze the Th1/Th17 regulation (FIG. 6).

EXAMPLE 6

Figure 7B:
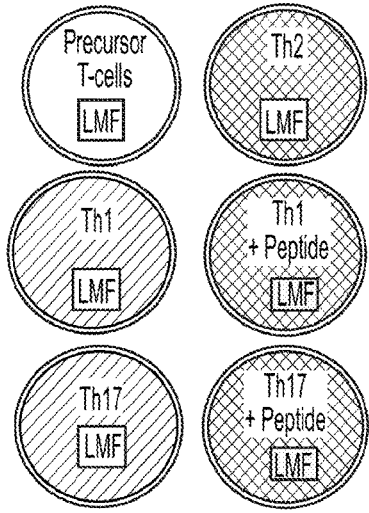
FIGS. 7A-7B. Human Th1 and Th17 cells induced proliferation of human lung myofibroblasts in co-culture.
Figure 7A:
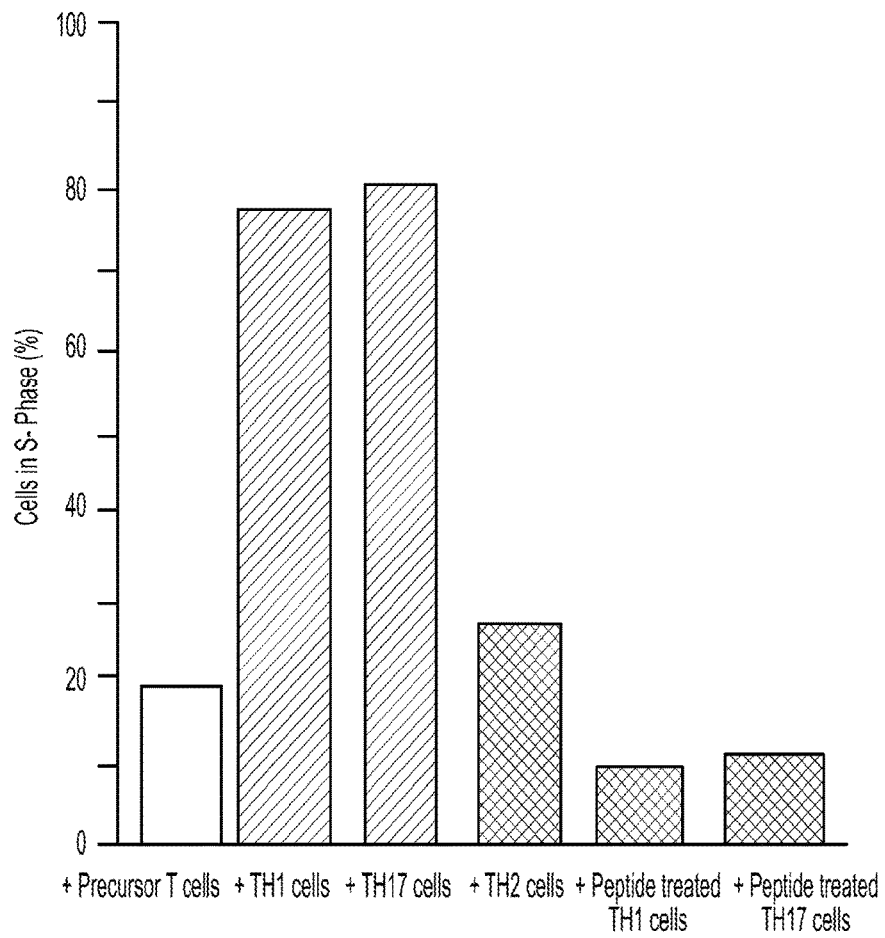

Human Th1 and Th17 but not Th2 Cells Induce Proliferation of Human Lung Myofibroblasts in a Co-culture System—Evidence that Inhibition of C/EBP-β-Thr266 Phosphorylation Blocks Lung Inflammatory Cells Primary human precursor CD-4+ T-cells cultured on glass were induced for 6 hr with IL-12 (Th1), IL-23 (Th17) or IL-4 (Th2). Also, precursor T-cells stimulated with Th1 and Th17 inducers were treated with the C/EBPβ peptide (100 pM) for 6 hr in an attempt of preventing the Th1 and Th17 phenotypes. Primary lung myofibroblasts cultured on Collagen type 1 cover slips in a defined media without serum, were inserted into the T-cell cultures [into identical cover slip spaces] after the T-cell inducers were removed with fresh media (FIG. 7B). LMF proliferation was analyzed by the presence of proliferating cell nuclear antigen (PCNA; DNA polymerase δ auxiliary protein), an S-phase marker (12). LMF cell proliferation was stimulated by Th1 and Th17 cells (FIG. 12) ~4-fold above control LMF (cultured with uninduced precursor T-cells) (FIG. 7) (P<0.01). LMF cell proliferation was not stimulated by either Th2 cells (FIG. 12) or T-cells treated with IL-12 or IL-23 plus the C/EBPβ peptide (FIG. 7). Thus, human LMF cell proliferation, an important step in their activation, is stimulated by human Th1 and Th17 cells. This novel system will allow analysis of Th-cell/LMF interactions.

EXAMPLE 7

Human Th1/Th17 Cells are the Prevalent Phenotype in IPF

Figure 8:
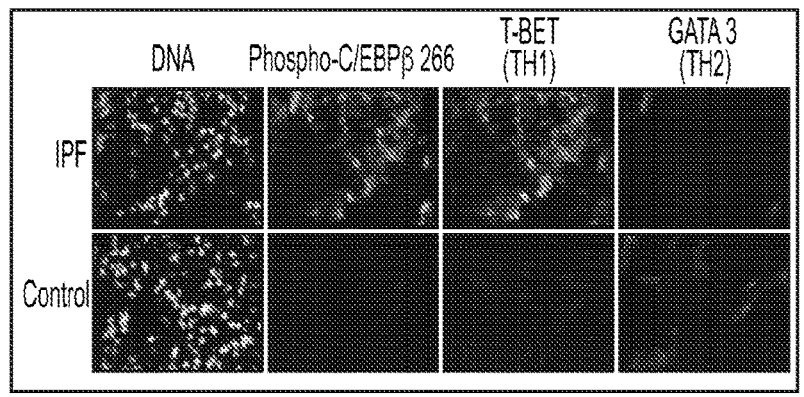
FIG. 8. Phosphorylation of C/EBPβ-Thr266 was induced and associated with the Th1 response in lungs from IPF patients. A representative patient with IPF and a representative control individual were studied. DNA; Phospho-C/EBPβThr266; T-Bet; and GATA-3 were identified by confocal laser scanning microscopy.
Figure 9:
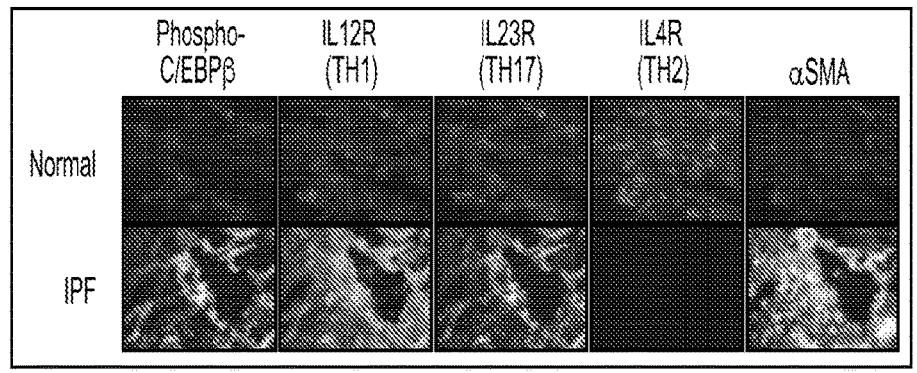
FIG. 9. Phosphorylation of C/EBPβ-Thr266 was induced and associated with the Th1/Th17 response in lungs from IPF patients. A representative patient with IPF and a representative control individual were studied. Phospho-C/EBPβThr266; L-12R; L-23R; IL-4Rα; and αSMA were identified by confocal laser scanning microscopy.
Figure 11:
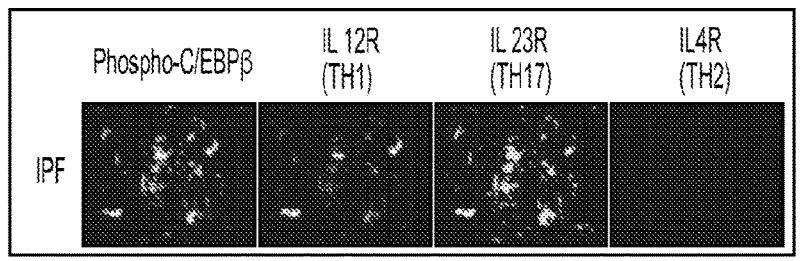
FIG. 11. Phosphorylation of C/EBPβ-Thr266 was induced and associated with the Th1/Th17 response in lungs from IPF lung tissue. Freshly isolated T-cells were purified and characterized as described below. Phospho-C/EBPβThr266; IL-12R; L-23R; and IL-4Rα; were identified by confocal laser scanning microscopy.
Figure 12:
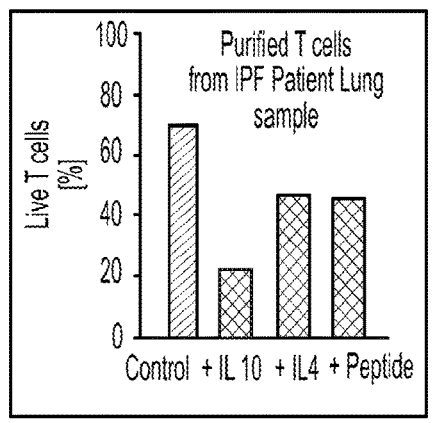
FIG. 12. Th2 stimuli and the C/EBPβ peptide induced apoptosis of isolated primary human lung Th1 and Th17 cells from an IPF patient. T-cells were isolated by CD-4+ affinity and treated for 16 hr with 10 µg/ml of IL-10 or L-4, or with 100 pM C/EBPβ peptide. Apoptosis was detected as described (12). The Th2 inducers and the C/EBPβ peptide (P<0.05) stimulated ex vivo apoptosis of Th-1 and Th-17 lung cells.

The clinical relevance of the experimental findings was confirmed by the presence of phosphorylated C/EBPβ-Thr266 in lung Th1 and Th17 cells in IPF (FIGS. 8 & 9). As depicted in FIGS. 11 and 12, >95% of lung CD-4+ T-cells in IPF explants expressed IL-12R and T-bet (a Th1 phenotype (55,84)); IL-23R (a Th17 phenotype (49,80)); and phospho-C/EBPβThr266. In these samples, 5% of the T-cells expressed IL-4R and GATA-3 (a Th2 phenotype (95). Normal lungs have ~10-fold fewer T-cells with a modest prevalence of Th2 cells (~60%). Certain experiments will systematically characterize the molecular and functional profiles of purified lung Th1/Th2/Th17 from IPF patients.

EXAMPLE 8

Figure 10:
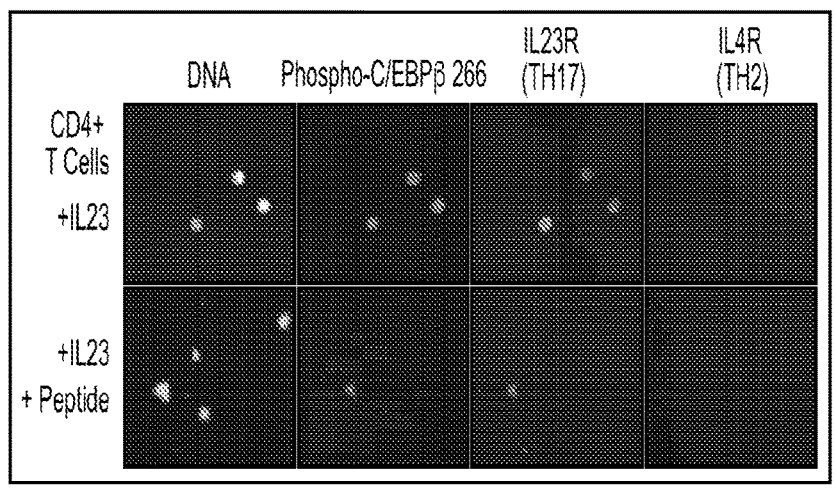
FIG. 10. Phosphorylation of C/EBPβ on Thr266 was induced and necessary for the Th1/Th17 response of human CD4+ T-cells to inflammatory inducers. Ex vivo experiments with human blood precursor T-cells. After 16 hr treatment with human recombinant L-12 (a Th1 inducer), normal human CD-4+ T-cells expressed the IL-12Rβ and T-Bet (a Th1 phenotype). When normal human blood CD-4+ T-cells were treated ex vivo with L-23 (a Th17 inducer), they expressed the IL-23R and GATA-3 (data not shown) (a Th17 phenotype).

Phosphorylation of C/EBPβ on Thr266 is Induced and Necessary for the Th1/Th17 Response of Human CD4+ T-cells to Inflammatory Inducers—Evidence that Inhibition of C/EBP-β-Thr266 Phosphorylation Blocks Lung Inflammatory Cells Results supporting that phosphorylation of human C/EBPβ on Thr266 confers the Th1/Th17 phenotype were obtained using freshly isolated, human CD-4+ human blood T-cells. After treatment with human recombinant IL-12 (a Th1 inducer), normal human blood CD-4+ T-cells expressed the IL-12R3 and T-Bet (a Th1 phenotype). When normal human CD-4+ T-cells were treated ex vivo with IL-23 (a Th17 inducer), they expressed the IL-23R (FIG. 10) and GATA-3 (data not shown) (a Th17 phenotype). Induction of Th1 and Th17 cells was linked to phosphorylation of endogenous C/EBPβ3 on Thr217. Blocking phosphorylation of endogenous C/EBPβ with the dominant negative C/EBPβ peptide prevented the activation of CD-4+ T-cells into either Th1 (and a population shift to Th2 cells) or Th17 (with induction of apoptosis and absence of Th2 cells) phenotypes (FIG. 10). IL-4 induced the Th2 phenotype while untreated CD-4+ T-cells remained uncommitted.

EXAMPLE 9

Isolation and Purification of T-cells from Fresh IPF Lung Tissue and their Ex Vivo Response to the C/EBPβ3 Peptide and Th2 Inducers Approximately, 10 million CD4+ T-cells were isolated and purified from 0.5 mg of a fresh IPF lung biopsy using specific antibodies against surface receptors. Greater than 95% of the T-cells were Th1 or Th17, judging by their IL-12R and IL-23R markers (FIG. 11). Greater than 90% of the T-cells expressed Th17 markers. These Th1/Th17-cells were treated ex vivo for 16 hr with 10 μg/ml of IL-4, IL-10 (Th2 inducers) or 100 pM C/EBPβ peptide (an inhibitor of human C/EBPβ-Thr266 phosphorylation). The treatment by the Th2 inducers or C/EBPβ peptide stimulated >35% apoptosis from baseline (FIG. 12), suggesting that this is a plausible mechanism by which inhibition of C/EBPβ-Thr217 phosphorylation contributes to blocking Th1/Th17 induction. This effect is congruent with the report of the protein/protein interaction between phosphorylated C/EBPβ-Thr217/procaspase-8 and the inhibition of procaspe-8 cleavage and self-activation by the XEVD caspase inhibitory box created by the Thr-217 phosphorylation in C/EBPβ (12).

In summary, Examples 3-9 above demonstrate that a) C/EBPβ-Thr217 phosphorylation is necessary for the activation of human and mouse myofibroblasts. The novel peptides of the invention inhibit myofibroblast activation; b) C/EBPβ-Thr217 phosphorylation is necessary for Bleomycin-induced activation of lung Th1 and Th17 cells; c) selective depletion of Th1 and Th17 cells, but not of Th2 cells, through ablation of phagocytic M1 macrophages prevents Bleomycin-induced activation of LMF and lung fibrosis; d) human Th1 and Th17 cells but not Th2 cells stimulate proliferation/activation of human LMF in co-culture; e) the clinical relevance of these findings was confirmed by the presence of phosphorylated C/EBPβ-Thr266 in lung Th1 and Th17 cells in IPF lung tissue and in T-cells freshly isolated from IPF lung tissue; f) the lung T-cells in IPF are >95% Th1/Th17; and g) the C/EBPβ peptide and Th2 inducers stimulate apoptosis of lung Th1/Th17 cells ex vivo freshly isolated from Bleomycin-treated mice or from IPF lung tissue.

EXAMPLE 10

C/EBPβ-Thr217 Phosphorylation Stimulates Macrophage Inflammasome Activation and Liver Injury This example provides studies to investigate whether signaling through phosphorylation of C/EBPβ-Thr217, a potential novel therapeutic target, is a major mechanism responsible for liver inflammation and injury through the activation of the inflammasome in liver macrophages. The effects of C/EBPβ-Phospho-Thr217 signaling that is evolutionarily conserved (identical in human C/EBPβ-Phospho-Thr266) on macrophage inflammasome activity and liver injury induced by hepatotoxins in mice and humans were studied.

Methods

Construction of C/EBPβ-Ala217 and C/EBPβ-Glu217 Mice

The Animal Protocol was approved by the VA San Diego Healthcare System's Veterinarian Medical Unit. Transgenic mice expressing either the C/EBPβ-Ala217, a dominant negative, nonphosphorylatable mutation, or C/EBPβ-Glu217, a dominant positive, phosphorylation mimic mutation of the C/EBPβ-Thr217 phosphoacceptor, were generated as described previously[27] and back-crossed to the parental wild-type inbreed FVB mice for >10 generations. The presence of the rsv gene was used to identify these transgenic mice by PCR. The primer sequences for the RSV PCR were custom designed (RSV.2271 sense TAGGGTGTGTTTAGGCGAAA (SEQ ID NO:1), and RSV.2510 anti-sense TCTGTTGCCTTCCTAATAAG (SEQ ID NO:2).

Animal Procedures

In the acute exposure to the hepatotoxins, C/EBPβ-wt, C/EBPβ-Ala217 and C/EBPβ-Glu217 mice[27] (23-27 g) each received intraperitoneal injections of $CCl_4$ (70 µl $CCl_4$ and 30 µl of mineral oil) or mineral oil (70 µl saline and 30 µl mineral oil), or Jo-2 Ab (Fas-L; 0.2 µg/g body weight) or saline vehicle (50 µl) only once. In other experiments, C/EBPβ-wt mice (25 g) each received intraperitoneal injections of $CCl_4$ (70 µl $CCl_4$ and 30 µl of mineral oil) or mineral oil (70 µl saline and 30 µl mineral oil) once but after 8 hr animals received either 50 µl saline (vehicle) or the cell permeant Ac-KAla217VD-CHO[21] (American Peptide) (100 µg IP). In these experiments, animals were sacrificed 30 hr after the last $CCl_4$ injection or 8 hr after the Fas-L injection.

Macrophage Purification

The reported standards for in vitro experiments with macrophages were followed[42]. Adult C/EBPβ-wt (yield $1.3 \times 10^5$ macrophages per liver), C/EBPβ-Ala217 (yield $2.2 \times 10^5$ macrophages per liver), C/EBPβ-Glu217 (yield $1.4 \times 10^5$ macrophages per liver) and TGFα (yield $1.6 \times 10^5$ macrophages per liver) mice of FVB background were used for the isolation of primary liver macrophages. Cells were prepared, by in situ perfusion and single-step density Nycodenz gradient (Accurate Chemical & Scientific, Westbury, N.Y.), as described previously[43]. Liver macrophages were isolated at density gradient of 13% and then affinity purified by magnetic beads linked to CD-11/CD-68 Antibodies (Miltenyl Biotechnology). No CSF-1 or supplements were used. An aliquot was plated on glass coverslips and allowed to sit 1 hr. at 37 C and then fixed with acetone: methanol. Liver macrophages were identified by their typical morphology, adherence to glass, and with antibodies against F-4/80 and CD-68. Purity of these preparations was greater than 95%. Aliquot of macrophages were cultured in RPMI 1640, 10% fetal bovine serum with L-glutamine, 25 µM HEPES and Penicillin/Streptomycin. In some experiments, liver macrophages were treated for 8 hr. with TGFα (10 µM).

Microscopy

Fluorescent labels were observed using antibodies against C/EBPβ, RSKPhosphoSer380, F4/80, NOS-2 TLR4, NFκB, IRF8, MyD88, NALP3, TLR-5, IL-1R1 and ASC (Santa Cruz Biotechnology, Santa Cruz, Calif.), or C/EBPβ-PhosphoThr217 in a Keyence fluorescent microscope fluorochromes utilized were Alexa 488, 750, 350, 647, and 594. At least 100 cells were analyzed per experimental point[18, 21, 23, 27] TO-PRO-3 (Molecular Probes, Eugene, Oreg.) was used to analyze nuclear morphology. Fluorescence and bright-field imaging were quantified using the Keyence microscope BZ9000 analysis software programs. The inter-observer agreement was >90%.

Inflammation Genes

The liver macrophage expression of 86 inflammation genes was determined by using the $RT^2$ Quantitative Real-Time PCR Array as described by the manufacturer (SABiosciences; Valencia, Calif.). Control and experimental freshly isolated liver macrophage samples were analyzed together with internal control samples for the RNA purification and amplification steps, as well as for housekeeping genes (β-actin), using the Bio-Rad iQ5 real-time PCR detection system (Bio-Rad, Hercules, Calif.)[21]. Isolation of total RNA, treatment with DNase, precipitation with chloroform, and cDNA synthesis was performed using 1 µg of total RNA as described for RT-PCR following the manufacturer's recommendations.

Immunoprecipitation and Immunoblots

Pre-cleared freshly isolated liver macrophage cell lysates were incubated for 2 hr. with purified C/EBPβ antibodies followed by the addition of A/G+ agarose (Santa Cruz Biotechnology) for 12 hr. The immunoprecipitation reactions each contained 500 µg of total protein and 2 µg antibody (or purified IgG pre-immune serum as negative control). Immunoprecipitates were washed 3 times in 500 ml cell lysis buffer and resolved by SDS-PAGE, and C/EBPβ-PhosphoThr2 7, TLR4, NFκB, IRF8, MyD88, NALP3, TLR-5, IL-1R1, ASC β-actin, active caspase 3, IL-1β, and IL-18 detected by western blot, following the chemoluminescence protocol. (Perkin-Elmer, Shelton, Conn.) using specific antibodies[18, 19, 21, 27]. Negative samples were performed omitting the first antibody.

Human Livers

Anonymous, de-identified liver samples were obtained from 16 patients with acute liver injury secondary to Toxic Oil Syndrome and moderately severe liver injury[35] and from 10 control subjects without liver disease (NDRI). The protocol was approved by the University of San Diego, San Diego Human Protection Program. Because all these samples were excess, standard of care and archival samples it was an exempted, non-consented IRB approved protocol.

Statistical Analysis

Results are expressed as mean (±SD or ±SE). Either the Student-t or the Wilcoxon Mann-Whitney tests were used to evaluate the differences of the means between groups for parametric and non-parametric populations, respectively, with a P value of <0.05 as significant.

Results

The modulation of Fas-L induced liver injury and inflammation by phosphorylated C/EBPβ-Thr217 in mice The degree of liver injury was determined after exposure to hepatotoxins (Fas and $CCl_4$) in mice by quantitative histology and immunohistochemistry[24], cell death assays[23], and by measuring serum alanine aminotransferase (ALT) levels[21], an indicator of liver injury used routinely in patient care as well as by the Food and Drug Administration in clinical drug studies[25].

Figure 13A:
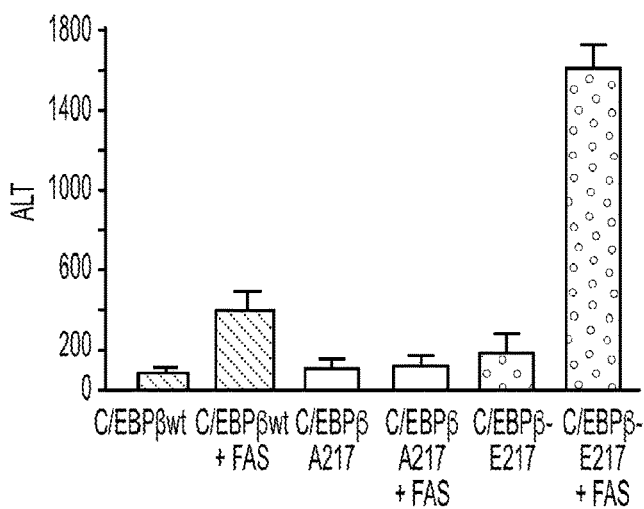
FIGS. 13a-13d. The modulation of Fas-L induced liver injury and inflammation by phosphorylated C/EBPβ-Thr217 in mice.
Figure 13B:
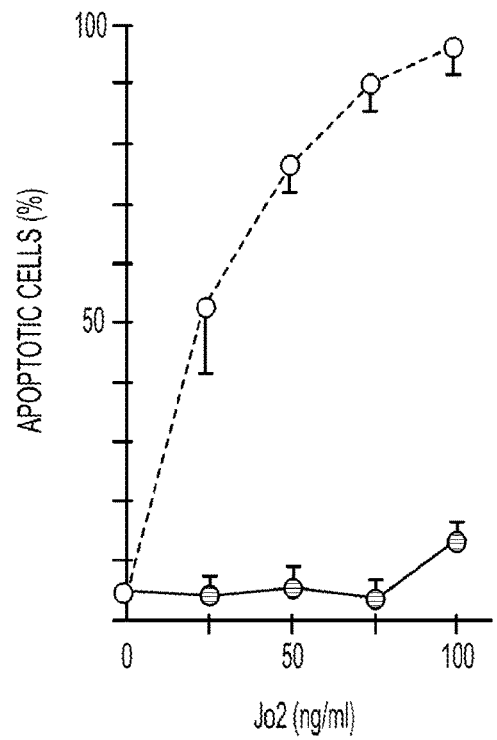
Figure 21:
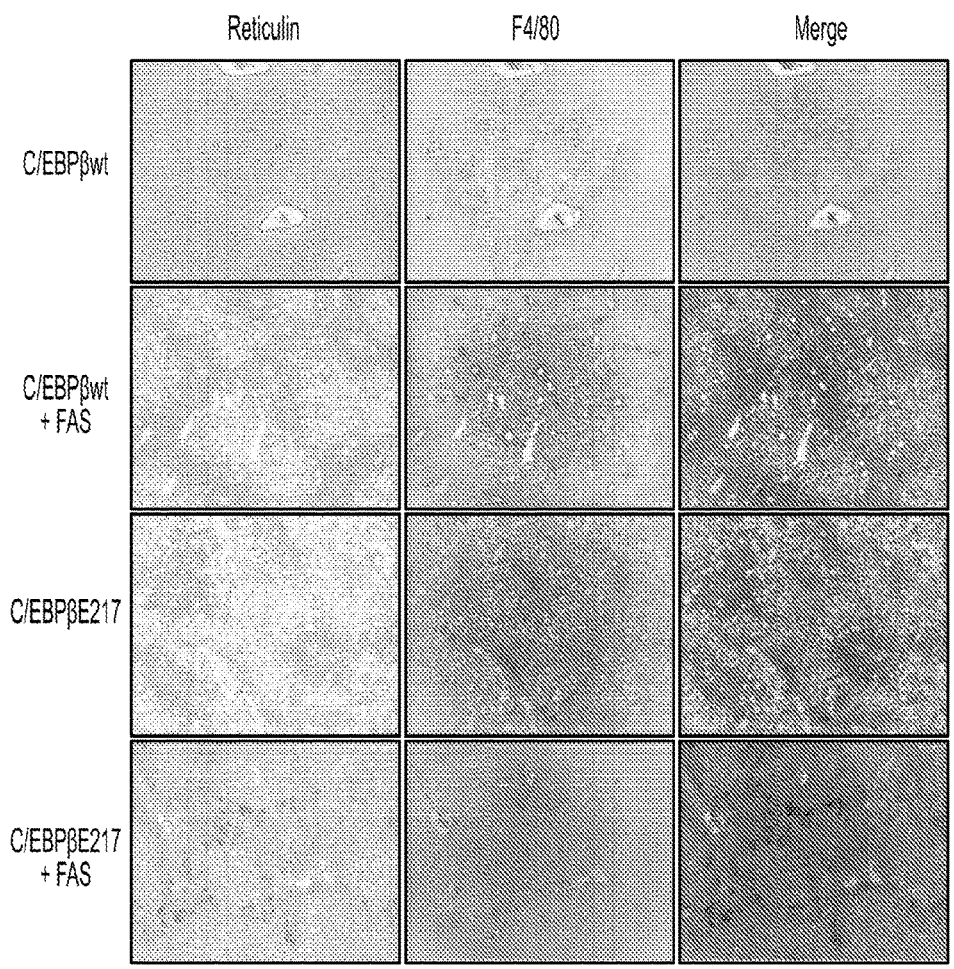
FIG. 21. The phosphorylation mimic C/EBPβ-Glu217 transgenic mice are more susceptible than control C/EBPβ-wt mice to liver injury induced by FAS-R activation. Representative histological samples of C/EBPβ-wt and C/EBPβ-Glu217 (E) mice after 30 hr. treatment with vehicle or CCl4. Formalin fixed liver samples were stained with reticulin histochemistry or F4/80 immunohistochemistry. The liver injury (reticulin stain) and the liver macrophage infiltration (F4/80) are induced by Jo-Ab(FAS) but the inductions is much more prominent in liver tissue from C/EBPβ-Glu217 mice. Representative example of experiment described in FIGS. 13a-13d above.
Figure 22:
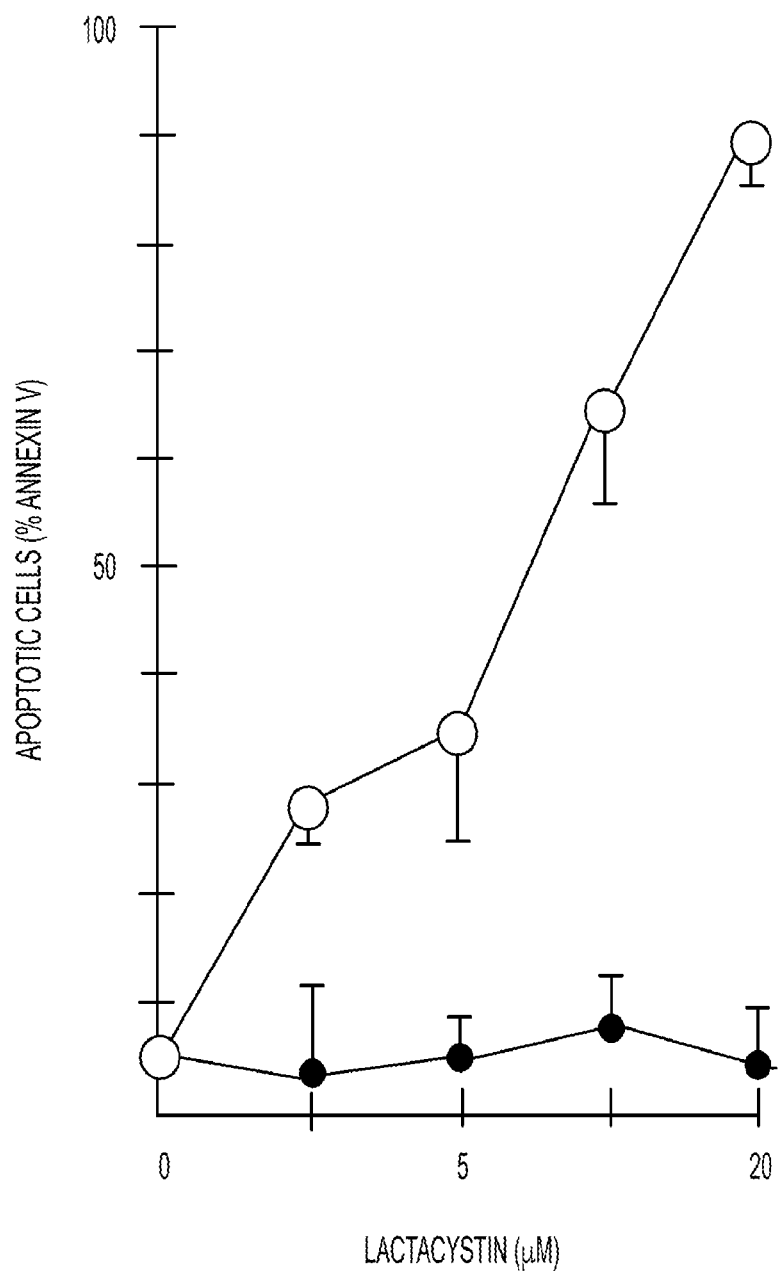
FIG. 22. Lactacystin induces minimal injury to primary hepatocytes isolated from C/EBPβ-Glu217 transgenic mice. Lactacystin induced minimal injury to cultured primary hepatocytes isolated from the phosphorylation mimic C/EBPβ-Glu217 transgenic mice (closed circles) when compared to hepatocytes from C/EBPβ-wt mice (open circles), judging by the apoptosis annexin-V assay (P<0.0001). Control cultured primary hepatocytes from C/EBPβ-wt untreated with Lactacystin had less than 5% baseline apoptosis. Values are mean (SD) of triplicate samples and representative of two experiments.

Fas-mediated IL-18 secretion by macrophages[8] and injection of a Fas agonist antibody (Jo-2 Ab)[26] induces severe liver injury in mice. First, the data showed that mice expressing the dominant positive, phosphorylation mimic C/EBPβ-Glu217 transgene were more susceptible than control C/EBPβ-wt mice to liver injury induced by Fas-R activation with Jo-2 Ab, judging by the serum ALT levels (P<0.0001) (FIG. 13a) and histology (FIG. 21). Mice expressing the dominant negative, non-phosphorylatable, C/EBPβ-Ala217 transgene were highly resistant to Fas-L induction of liver injury (P<0.01) (FIG. 13a). In contrast, Fas-L (Jo-2 Ab) induced minimal injury to cultured primary hepatocytes isolated from the phosphorylation mimic C/EBPβ-Glu217 transgenic mice when compared to hepatocytes from C/EBPβ-wt mice, judging by the apoptosis annexin-V assay (P<0.001) (FIG. 13b). Control cultured primary hepatocytes from C/EBPβ-wt untreated with Jo-2 had less than 5% baseline apoptosis. Congruent with their resistance to Fas-induced cell injury, the C/EBPβ-Glu217 cultured primary hepatocytes were also refractory to apoptosis induced by the proteasome inhibitor lactacystin[27] when compared to C/EBPβ-wt cultured primary hepatocytes (FIG. 22) Collectively, these experiments indicate that the susceptibility to severe liver injury induced by Fas-L signaling requires phosphorylation of C/EBPβ-Thr217 in liver cells other than hepatocytes that would be missing from these tissue culture studies. Although of interest, the resistance of C/EBPβ-Glu217 hepatocytes to Fas and lactacystin induced injury is not the focus of these studies.

Figure 13C:
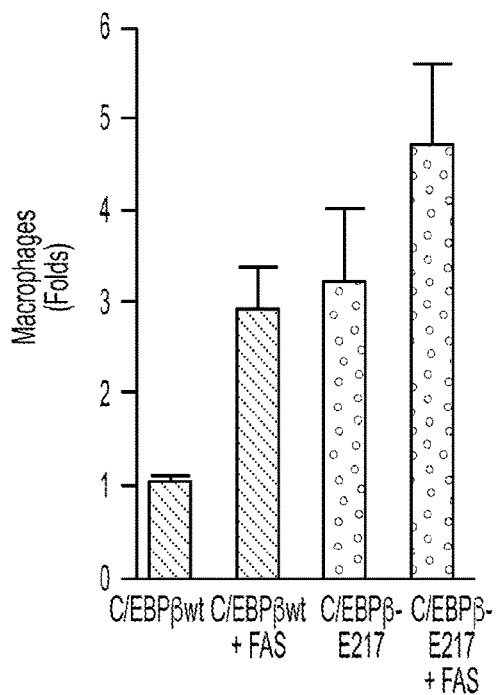
Figure 13D:
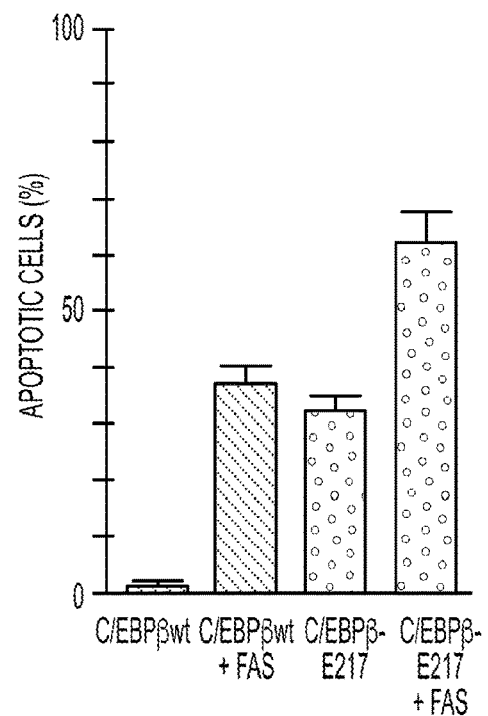

Both hepatocytes and non-parenchymal liver cells, including macrophages, express the Fas receptor (CD95)[28]. In this context, it was found that Fas-L also stimulated a greater infiltration of F4/80+ macrophage inflammatory cells in the livers of C/EBPβ-Glu217 mice than in the livers of C/EBPβ-wt mice (FIG. 13c and FIG. 21), which corresponded to a greater area of hepatocyte apoptotic damage (FIG. 13d and FIG. 21).

Activation of Cultured Primary Liver Macrophages by TGF-α is Associated with Phosphorylation of C/EBPβ-Thr217

The above experiments suggested that liver macrophages contribute to the amplification of liver injury induced by Fas-L in C/EBPβ-Glu217 mice and are the general mechanism of injury in C/EBPβ-wt mice, as reported for Fas-L and other animal models of liver injury[4, 5, 6, 7, 8]. Because expression of C/EBPβ in macrophages is of great relevance to the maturation and function of these cells[13, 14, 15, 16, 17], it was assessed whether phosphorylated C/EBPβ-Thr217 modulates the polarization of inflammatory primary liver macrophages, isolated as reported previously[23].

Figure 14A:
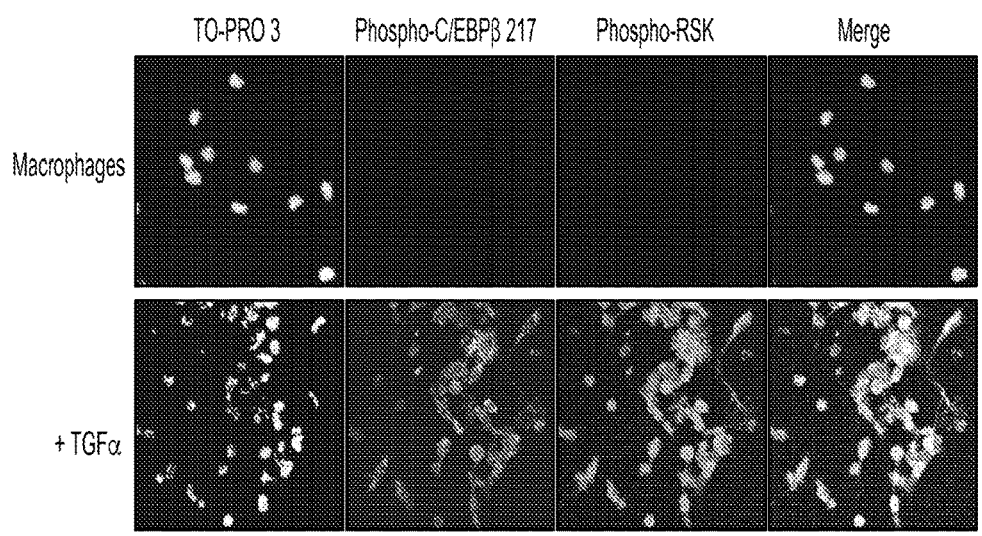
FIGS. 14a-14b. Activation of cultured primary liver macrophages by TGF-α is associated with phosphorylation of C/EBPβ-Thr217. Liver macrophages cultured in RPMI 1640, 10% fetal bovine serum with L-glutamine, 25 LM HEPES and Penicillin/Streptomycin were treated for 8 hr with TGFα (10 μM).
Figure 14B:
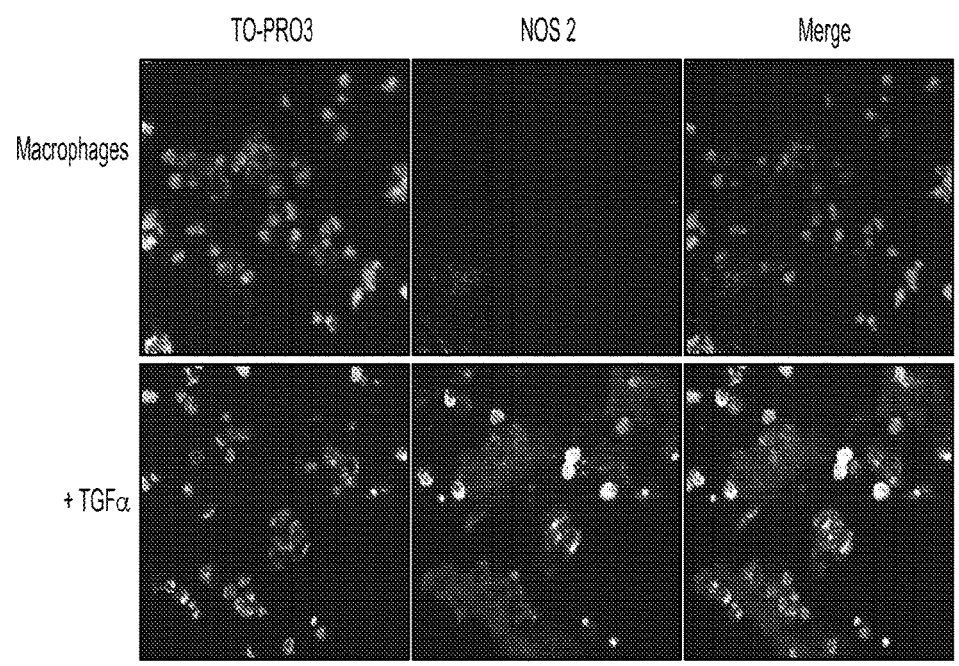

After treatment with TGF-α, an activator of the MAPK signaling[18] and a classical inflammatory macrophage inducer[17], freshly isolated cultured liver macrophages from C/EBPβ-wt mice expressed activated RSK-phospho-Ser380 and phosphorylation of endogenous C/EBPβ on Thr217[18] (FIG. 14a), as well as NOS-2, whose expression in activated macrophages is mediated by C/EBPβ[29] (FIG. 14b). Collectively, these results indicate a potential link between phosphorylation of C/EBPβ-Thr217 in liver macrophages, macrophage activation and liver injury in vivo in mice and in cultured cells.

Phosphorylation of C/EBPβ on Thr217 is induced and necessary for the liver macrophage activation after hepatotoxin treatment in mice To analyze whether phosphorylation of C/EBPβ on Thr217 is induced and necessary for the liver macrophage activation by chemical liver injury, a single dose of $CCl_4$, which is a classical and predictable hepatotoxin that induces oxidative stress in rodent and human livers[21, 30, 31], was administered to C/EBPβ-wt, TGF-α, C/EBPβ-Glu217, and C/EBPβ-Ala217 transgenic mice. Eight hours later, C/EBPβ-wt mice received either an intraperitoneal injection of the cell permeant, dominant negative C/EBPβ peptide (100 μg) or vehicle (50 μl saline). In earlier studies, it was found that this peptide dose provided adequate systemic and liver bioavailability in mice and blocked phosphorylation of C/EBPβ-Thr217[21, 27]. Animals were sacrificed at 30 hr at the peak of liver injury.

Figure 15A:
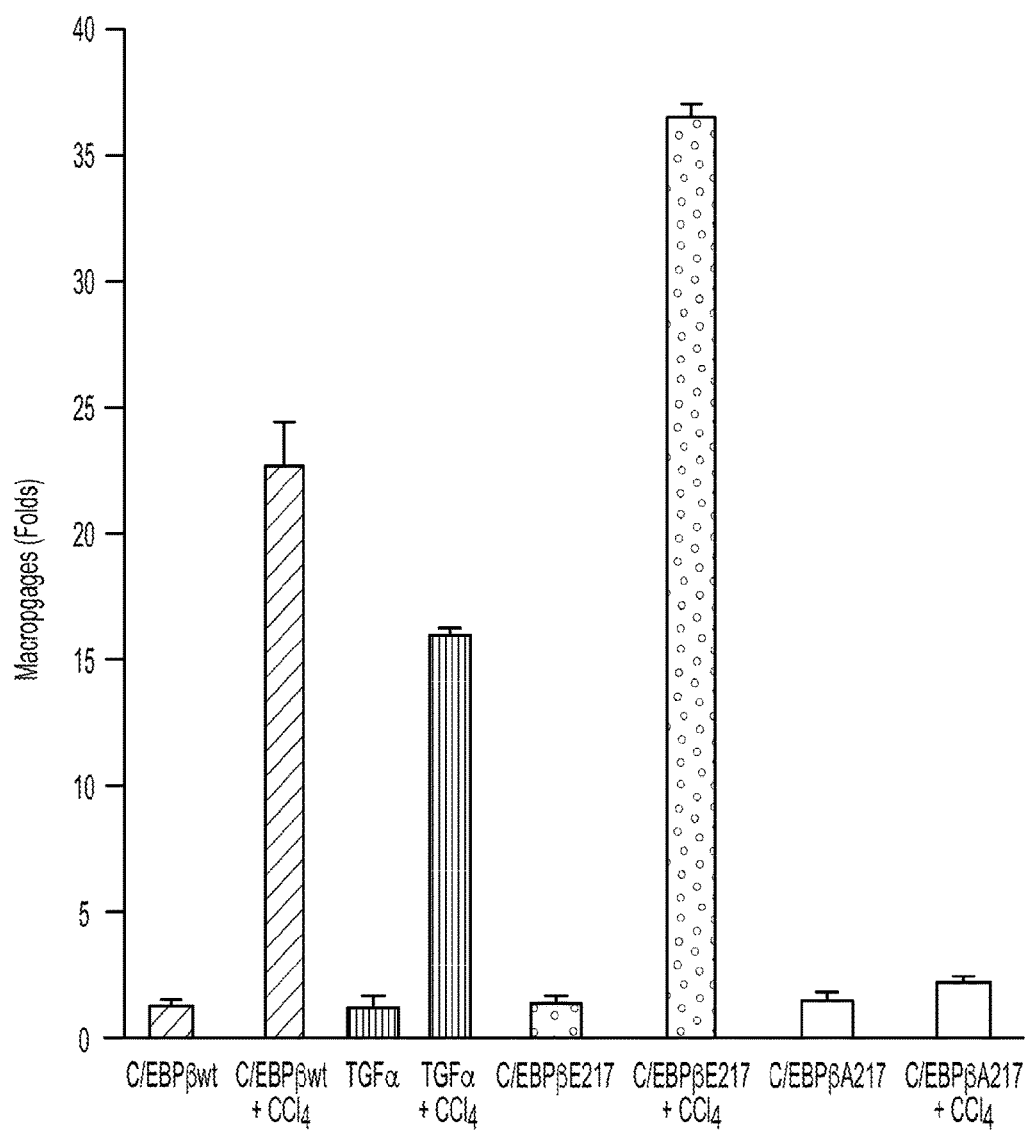
FIGS. 15a-15e. Phosphorylation of C/EBPβ on Thr217 is induced and necessary for the liver macrophage activation after hepatotoxin treatment in mice.
Figure 15B:
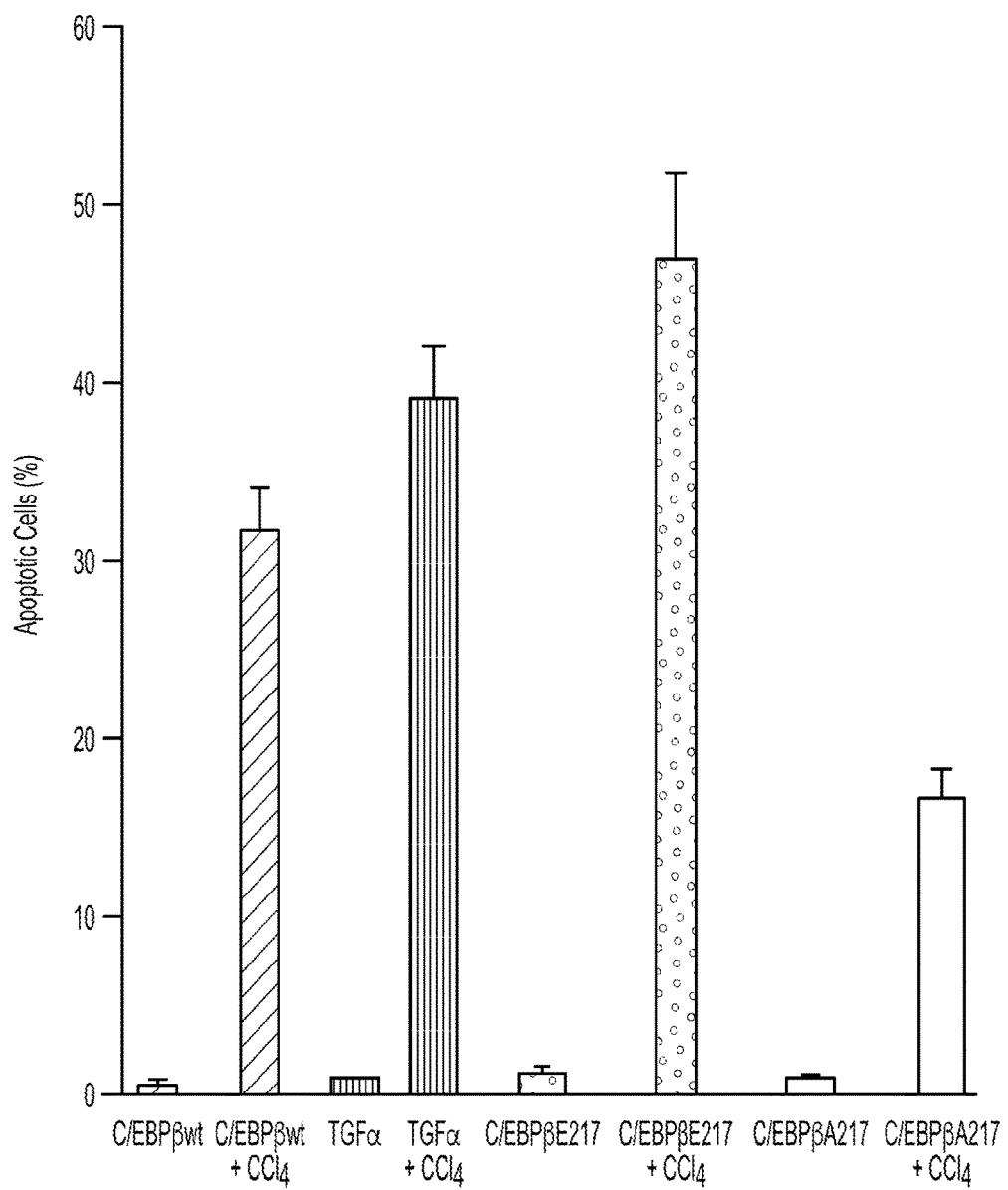
Figure 15C:
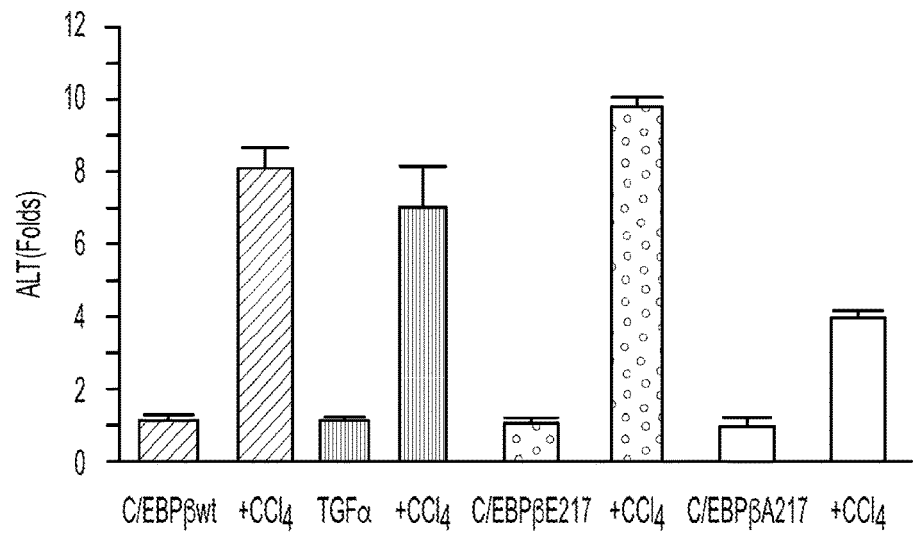
Figure 23A:
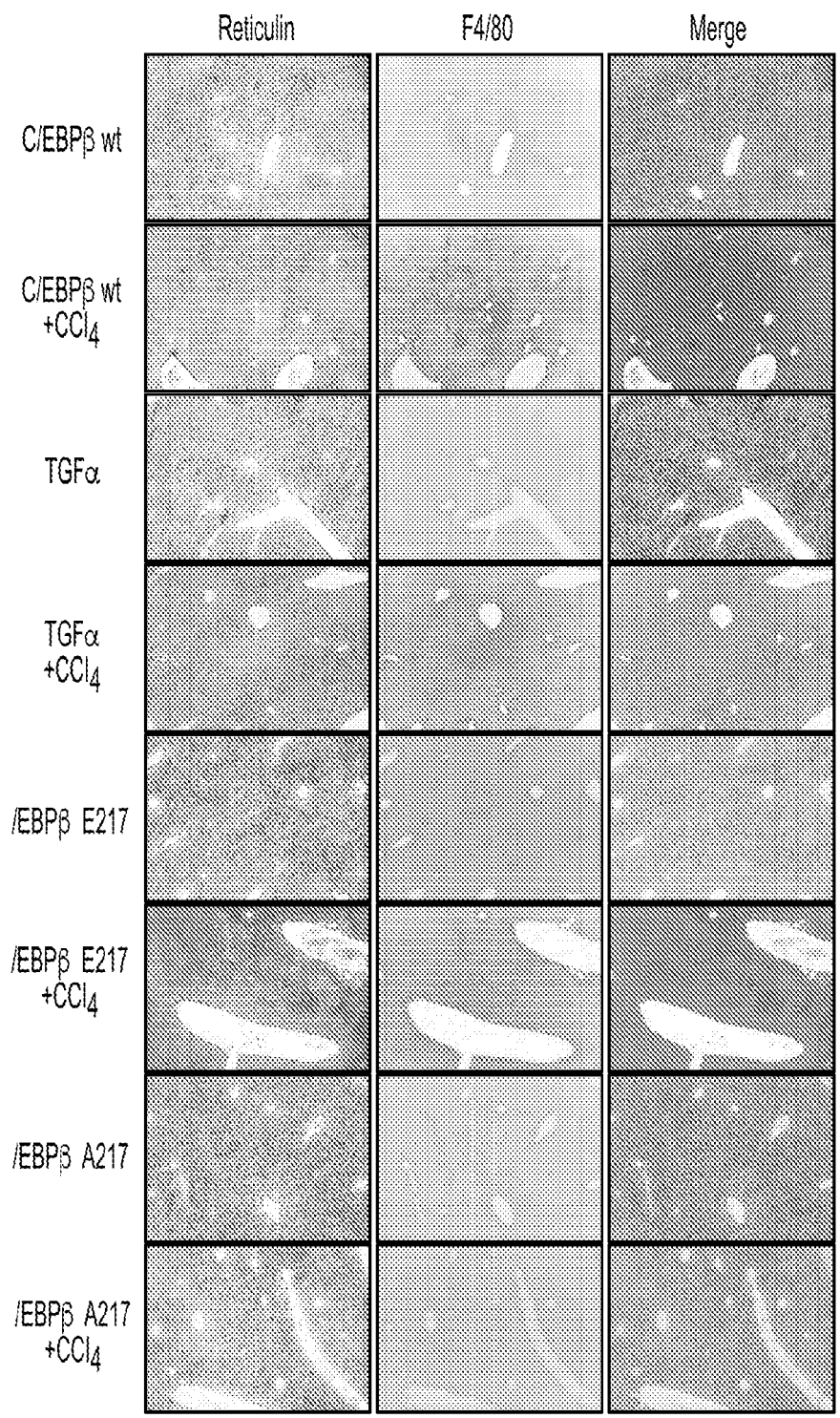
FIGS. 23a-23b. The phosphorylation mimic C/EBPβ-Glu217 transgenic mice are more susceptible than the control mice to liver injury induced by CCl4.

$CCl_4$ treatment induced a severe acute liver injury with architectural collapse in C/EBPβ-wt mice but a mild-to-moderate injury in C/EBPβ-Ala217 mice (FIG. 23a, reticulin stain). As found for Fas (FIG. 13a and FIG. 21), the liver injury induced by $CCl_4$ was also more severe in C/EBPβ-Glu217 mice (FIG. 15a-15e, and FIG. 23a). The degree of liver injury by histological analysis in these animal models correlated with both macrophage infiltration of the liver (FIG. 15a and FIG. 23a, F4/80 stain), the degree of hepatocyte apoptosis (FIG. 15b), and the serum ALT levels (FIG. 15c).

Acute administration of $CCl_4$ stimulated ~20-fold macrophage infiltration of the liver in C/EBPβ-wt mice after 30 hr. (P<0.005), as identified by the expression of F4/80 by quantitative microscopy[23] (FIG. 15a). $CCl_4$ administration induced even a higher degree of macrophage infiltration in the livers of the phosphorylation mimic C/EBPβ-Glu217 mice (~40-folds) (P<0.0001) (FIG. 15a). Moreover, blocking phosphorylation of C/EBPβ-Thr217 with the C/EBPβ-Ala217 transgene suppressed $CCl_4$-induced macrophage liver infiltration by about 90% when compared to C/EBPβ-wt mice (P<0.001) (FIG. 15a).

Figures 15D, 15E:
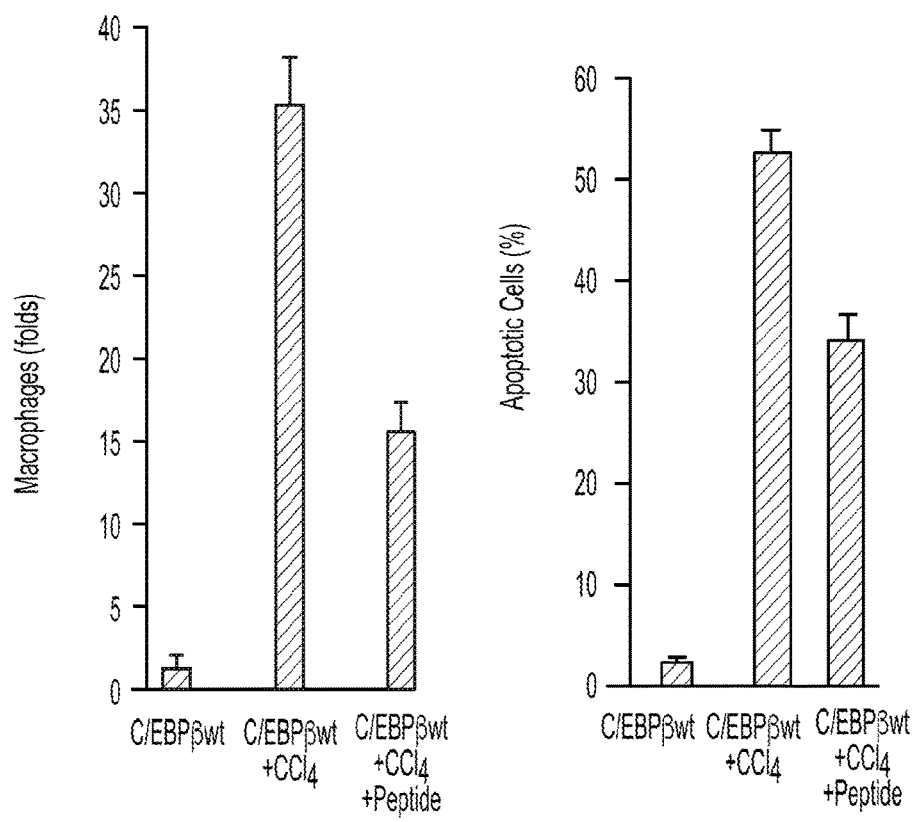
Figure 23B:
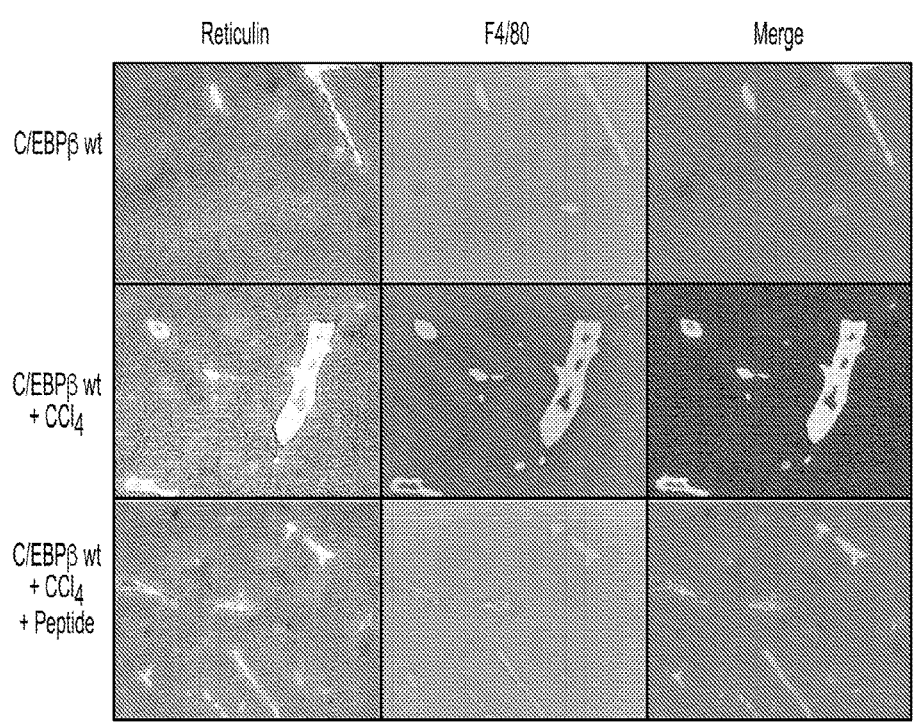

The dominant negative peptide that blocks C/EBPβ-Thr217 phosphorylation[21] also inhibited the $CCl_4$-induction of liver macrophage infiltration by ~60% (P<0.01) (FIG. 15d and FIG. 23b, F4/80 stain), as well as liver injury by ~45% (P<0.001) (FIG. 15e and FIG. 23b, reticulin stain).

Figures 16A, 16B, 16C:
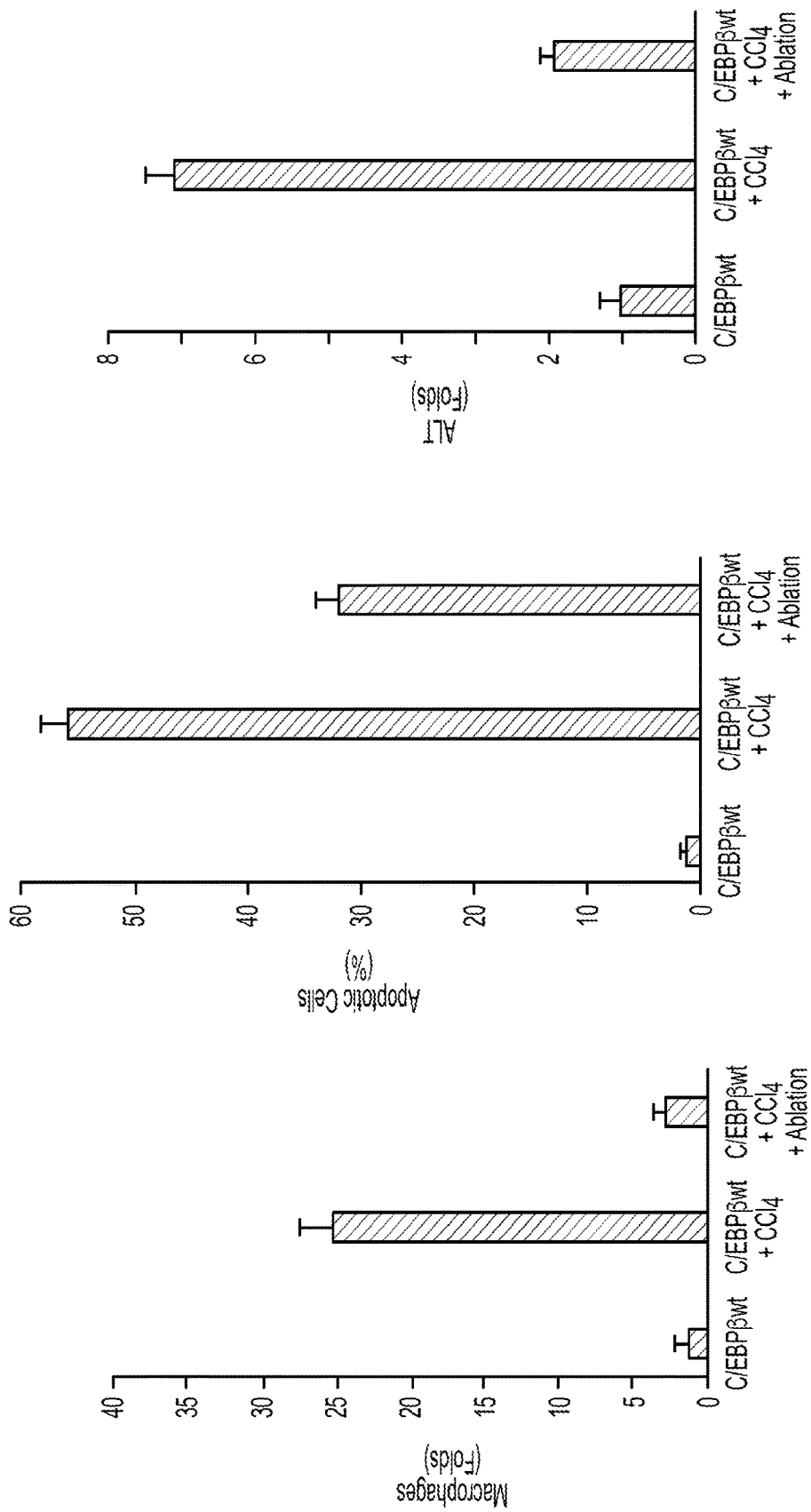
FIGS. 16a-16f. Macrophages are induced and necessary for the liver injury in response to hepatotoxin treatment in mice.
Figure 24:
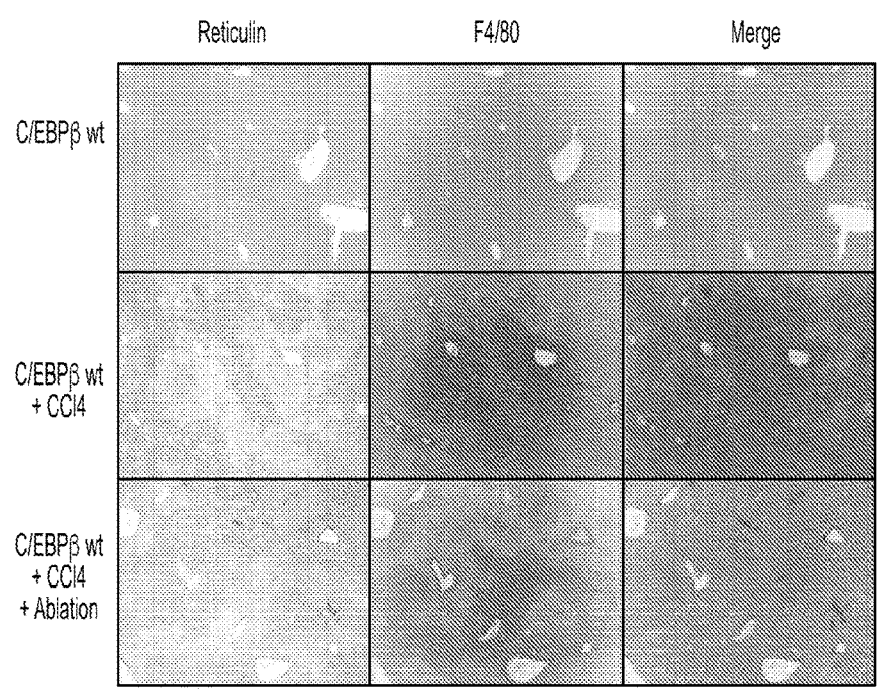
FIG. 24. Macrophage ablation prevents CCl4-induced liver injury and macrophage infiltration. Histological samples of C/EBPβ-wt mice that received Clondronate liposomes to deplete macrophages 24 hr. before the administration of vehicle or CCl4. Macrophage depleted mice had a marked reduction in liver injury (reticulin stain) and liver macrophage infiltration (F4/80) 30 hrs. after C114 treatment. Representative example of experiment described in FIGS. 16a-16f above.

Macrophages are Induced and Necessary for the Liver Injury in Response to Hepatotoxin Treatment in Mice To ascertain the role of macrophages in toxic liver injury with an alternative approach, C/EBPβ-wt mice received Clodronate liposomes to deplete macrophages 24 hr. before the administration of the hepatotoxin[5]. These animals had a marked reduction in liver macrophages infiltration (~90%; P<0.005) (FIG. 16a and FIG. 24), and in liver injury at 30-hr. after $CCl_4$ treatment as assessed by counting apoptotic hepatocytes in liver biopsies (P<0.01) (FIG. 16b and FIG. 24) and by the measurement of serum ALT (75%; P<0.005) (FIG. 16c).

Figure 16F:
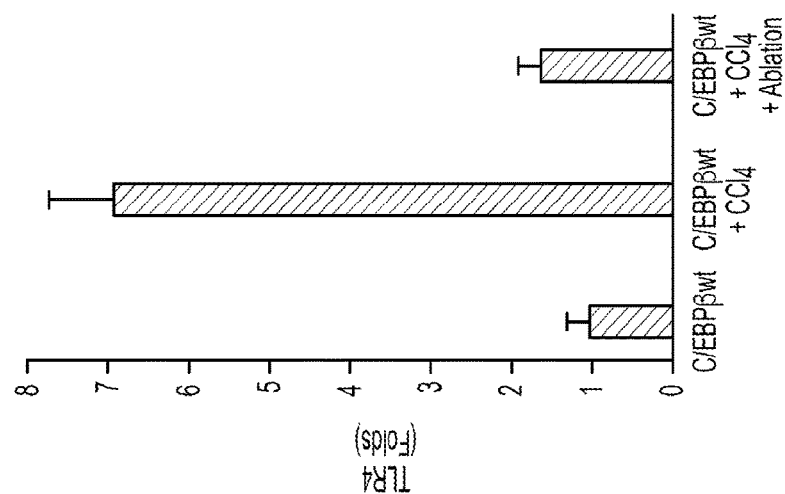
Figure 16E:
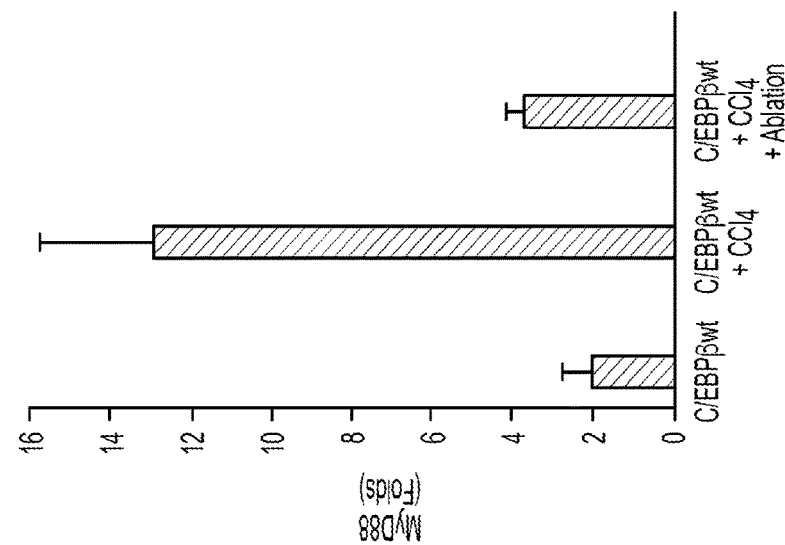
Figure 16D:
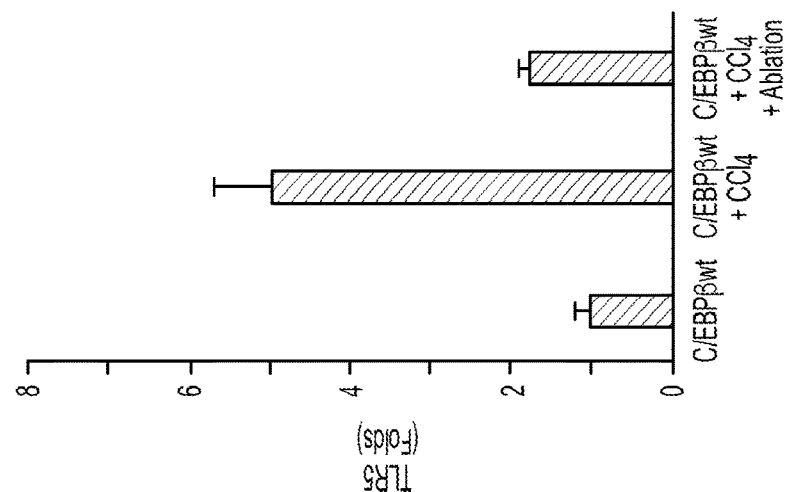

Thirty-hours after $CCl_4$ treatment, the CD-11/CD-68 mouse macrophages purified from livers of C/EBPβ-wt mice expressed high levels of TLR5, MyD88 and TLR4 (FIGS. 16d, 16e and 16f), which are critical components of the inflammasome[1]. Clodronate liposomes induced an inhibition of TLR5, MyD88 and TLR4 expression in liver macrophages isolated from $CCl_4$ treated animals compared to liver macrophages isolated from $CCl_4$ treated animals that did not receive Clodronate liposomes (P<0.001) (FIGS. 16d, 16e and 16f), suggesting that activation of the inflammasome in liver macrophages is relevant for the liver injury induced by the hepatotoxin. Altogether, the results obtained from experiments with phosphorylation dominant positive and dominant negative C/EBPβ-Thr217 transgenic mice and hepatocytes as well as with macrophage ablation suggest that phosphorylation of C/EBPβ-Thr217 (or C/EBPβ-Glu217) in macrophages is a critical step in hepatotoxin-induced liver injury.

Phosphorylated C/EBPβ-Thr217 Stimulates the Inflammasome Signal 1 Complex in Liver Macrophages in Mice A priming stimulus (signal 1), acting through NFκB pathway, often precedes assembly of the inflammasome complex in order to upregulate the expression of pro-IL-1β and NALP3. Upon either ligand sensing or enzymatic activation within the cytosol (signal 2), the cytosolic sensors oligomerize to form an activation platform for caspase 1[32].

Thirty-hours after CCl$_4$ treatment, the CD-11/CD-68 primary liver macrophages purified from C/EBPβ-wt mice expressed phosphorylated C/EBPβ-Thr217, which was co-expressed with critical components of the inflammasome signal 1 complex gene products, including TLR4, NFκB, IRF8 and MyD88 (FIG. 17a)[1].

Figure 17A:
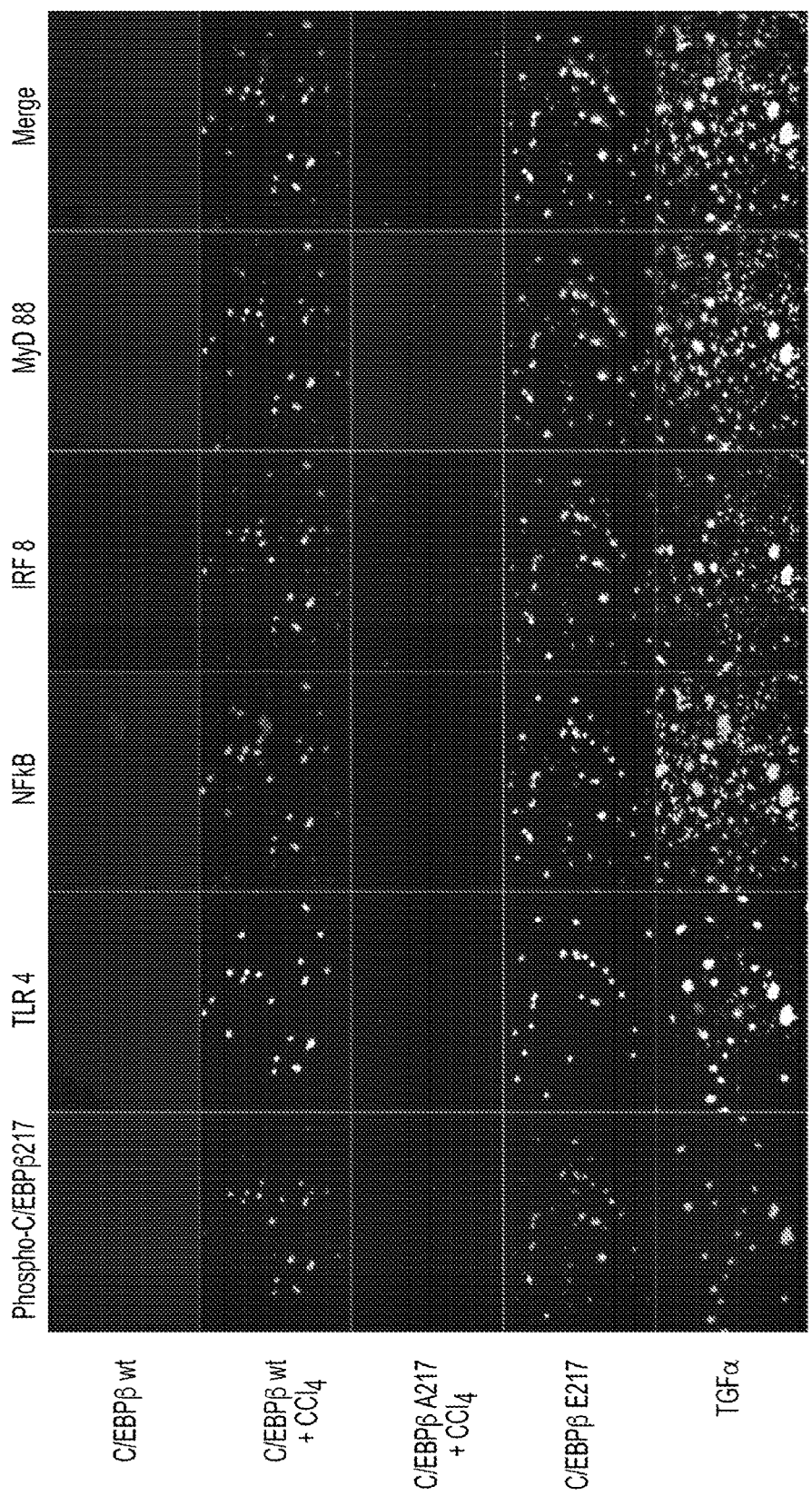
FIGS. 17a-17b. Phosphorylated C/EBPβ-Thr217 stimulates the inflammasome signal 1 complex in liver macrophages in mice.

Phosphorylation of C/EBPβ-Thr217 is required for the expression of the inflammasome signal 1 complex in liver macrophages induced by hepatotoxin treatment since it was blocked in the nonphosphorylatable C/EBPβ-Ala217 transgenic mice (FIG. 17a). In contrast, liver macrophages isolated from the dominant positive C/EBPβ-Glu217 transgenic mice expressed the inflammasome signal 1 complex even in the absence of hepatotoxin treatment (FIG. 17a). Similarly, in liver macrophages isolated from TGFα transgenic mice, which have an stimulated MAPK signaling, phosphorylated C/EBPβ-Thr217 was associated with the expression of critical protein components of the inflammasome signal 1 complex, including TLR4, NFκB, IRF8 and MyD88 (FIG. 17a).

Figure 17B:
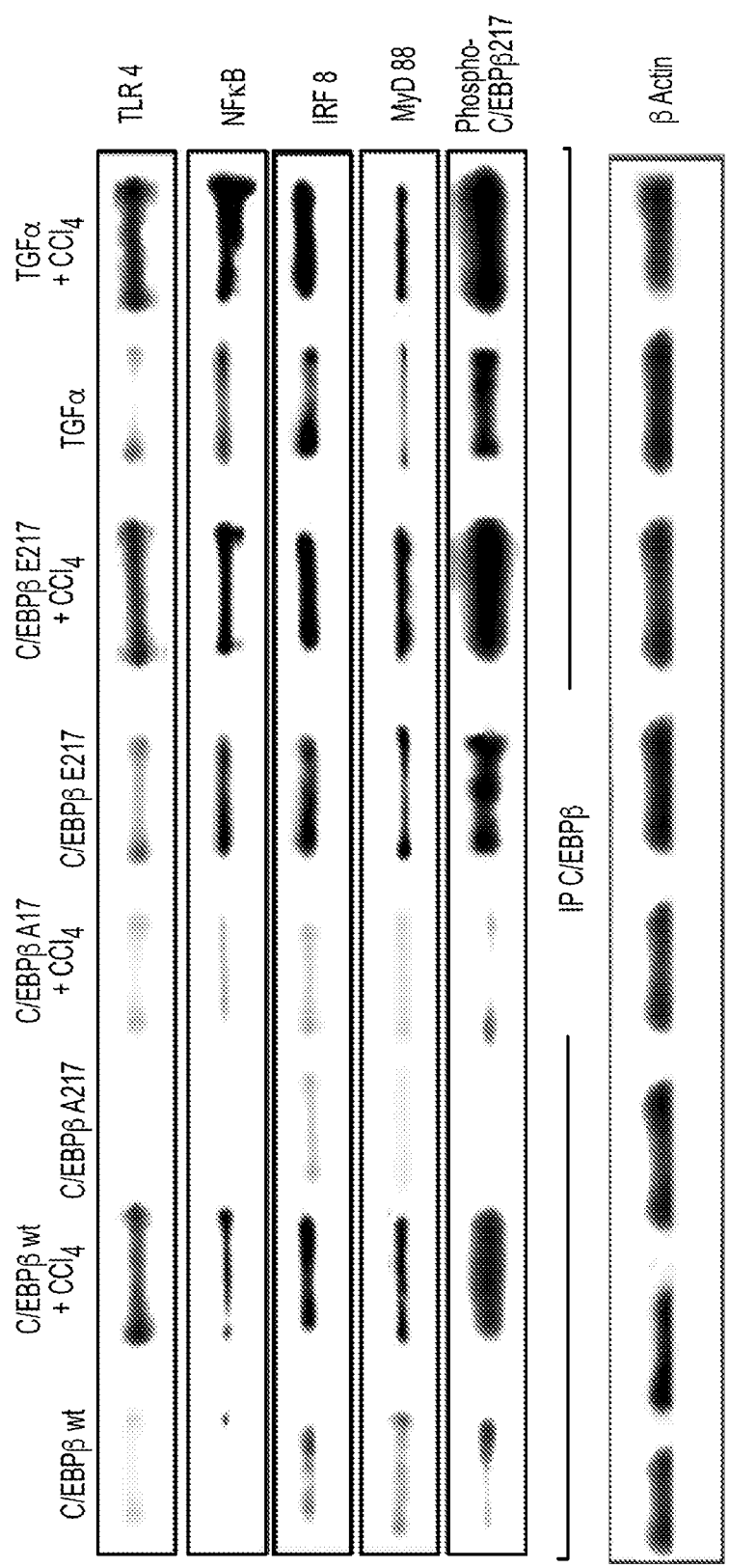

To further delineate the physical association of phosphorylated C/EBPβ-Thr217 with members of the inflammasome signal 1 complex in purified liver macrophages after hepatotoxin treatment, we immunoprecipitated C/EBPβ, which was normalized by β-actin for the immunoblots, and analyzed its associated proteins. It was found that phosphorylated C/EBPβ-Thr217 or C/EBPβ-Glu217, but not unphosphorylated C/EBPβ-Thr217 or C/EBPβ-Ala217, were physically associated with TLR4, NFκB, IRF8 and MyD88 in freshly isolated primary liver macrophages (FIG. 17b). Treatment with CCl$_4$ (and the consequent macrophage activation) increased the association between phosphorylated C/EBPβ-Thr217 or C/EBPβ-Glu217 and inflammasome signal 1 proteins (FIG. 17b).

Figure 18A:
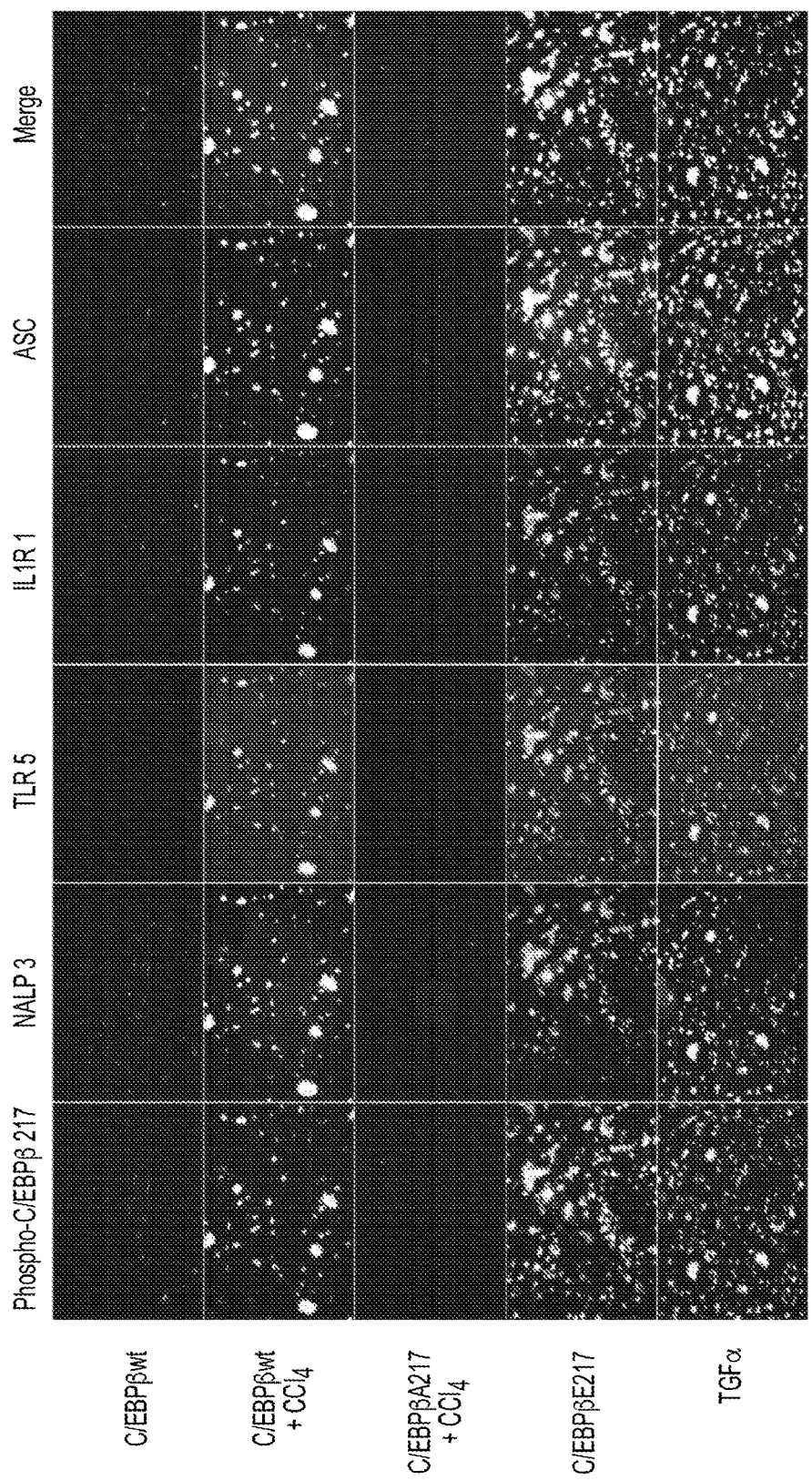
FIGS. 18a-18b. Phosphorylated C/EBPβ-Thr217 stimulates expression of the inflammasome complex signal 2 in liver macrophages in mice.
Figure 18B:
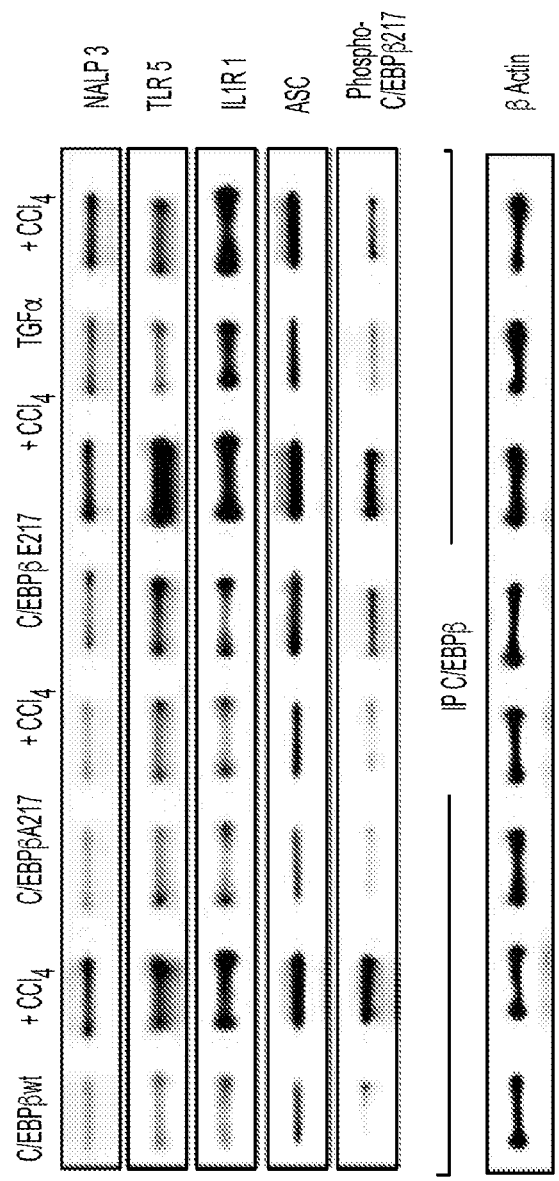

Phosphorylated C/EBPβ-Thr217 Stimulates Expression of the Inflammasome Complex Signal 2 in Liver Macrophages in Mice Given that activation of the inflammasome signal 2 pathway is essential for expression of several inflammatory cytokines[1, 11, 33], the role of phosphorylated C/EBPβ-Thr217 was analyzed on the inflammasome signal 2 pathway in liver macrophages. It was found that CCl$_4$ treatment of C/EBPβ-wt mice stimulated the expression of the inflammasome signal 2 proteins in liver macrophages (FIGS. 18a). Thirty-hours after CCl$_4$ treatment, the CD-11/CD-68 liver macrophages freshly purified from C/EBPβ-wt mice expressed phosphorylated C/EBPβ-Thr217, which was co-expressed with critical components of the inflammasome complex signal 2, including NALP3, TLR5, IL-1R1 and the adaptor protein ASC (FIG. 18a)[1]. Expression of phosphorylated C/EBPβ-Thr217 is also required for the induction of the inflammasome multiprotein complex signal 2 in liver macrophages stimulated by hepatotoxin treatment since both were blocked in the nonphosphorylatable C/EBPβ-Ala217 mice (FIG. 18b). In contrast, liver macrophages isolated from the phosphorylation mimic C/EBPβ-Glu217 mice, even in the absence of hepatotoxin treatment, expressed a partially activated (primed) inflammasome signal 2 complex (FIG. 18a). In addition, in liver macrophages isolated from TGFα transgenic mice, phosphorylated C/EBPβ-Thr217 was associated with the expression of critical components of the inflammasome signal 2 complex, including NALP3, TLR5, IL-1R1 and ASC (FIG. 18a).

To further delineate the physical association of phosphorylated C/EBPβ-Thr217 with members of the inflammasome signal 2 complex in purified primary liver macrophages after hepatotoxin treatment, C/EBPβ was immunoprecipitated and its associated proteins were analyzed. It was found that liver injury increased the physical association between inflammasome signal 2 complex proteins (NALP3, TLR-5, IL-1R1 and ASC) in liver macrophages with phosphorylated C/EBPβ-Thr217 or C/EBPβ-Glu217, but not with unphosphorylated C/EBPβ-Thr217 or C/EBPβ-Ala217 (FIG. 18b).

Figure 19A:
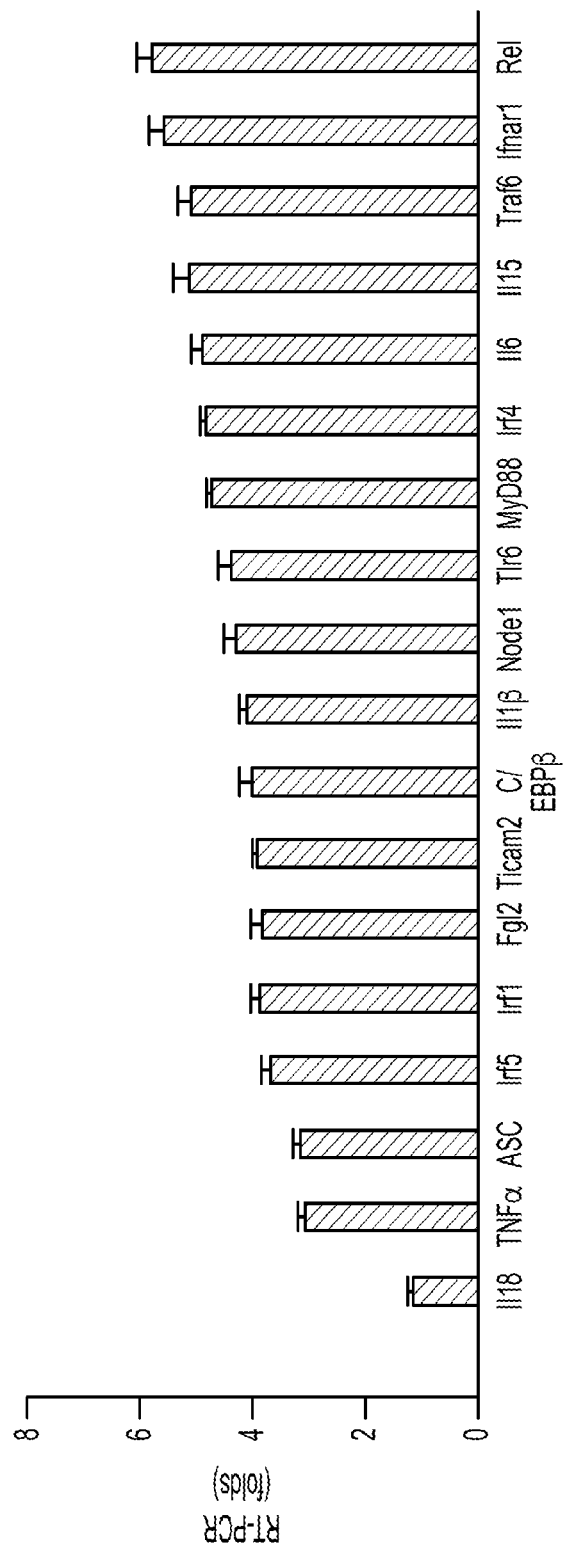
FIGS. 19a-19c. Phosphorylated C/EBPβ-Thr217 stimulates the expression of inflammasome structural and byproduct genes in liver macrophages in mice.
Figure 19B:
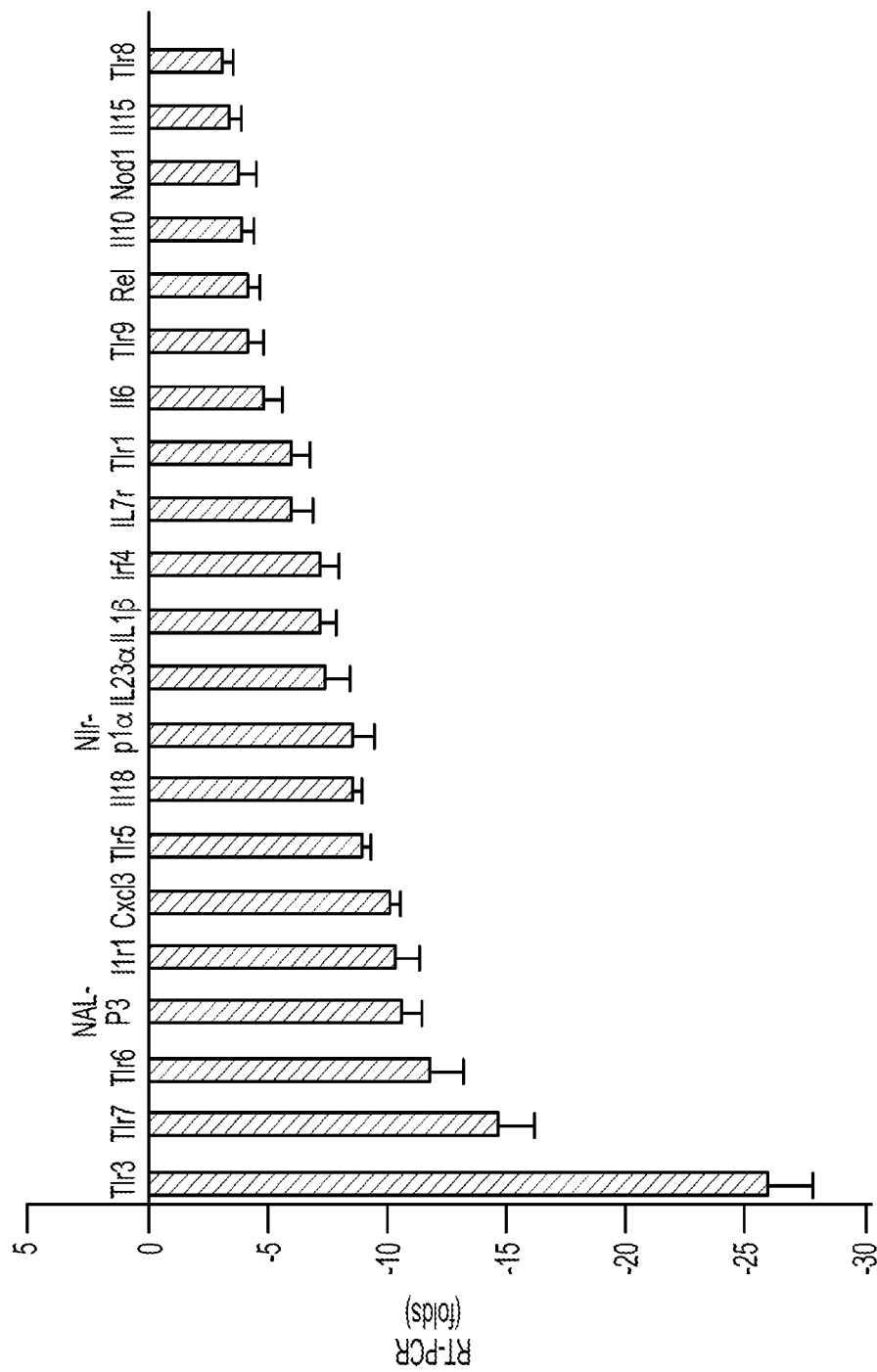
Figure 19C:
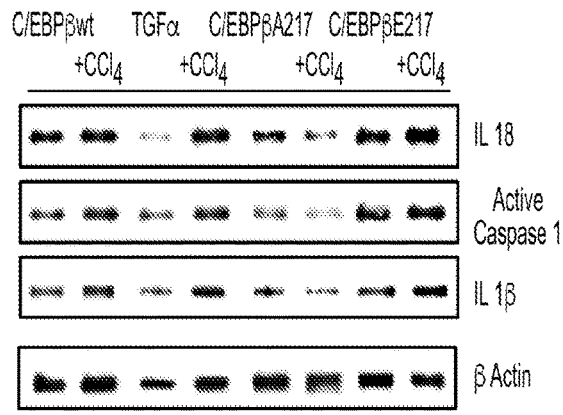

Phosphorylated C/EBPβ-Thr217 Stimulates the Expression of Inflammasome Structural and Byproduct Genes in Liver Macrophages in Mice It was found that freshly isolated liver macrophages from the phosphorylation mimic C/EBPβ-Glu217 mice express an activated transcriptosome related to the Inflammasome when compared to C/EBPβ-wt mice. This included the increased expression of inflammasome genes (ASC, IRF-1, IRF-4 IRF-5, TCAM-2, TRL-6, TRAF-6, Myo-D88, Nod-1 and Rel) as well as the increased expression of direct and indirect cytokine gene byproducts (IL-1β, IL-6, IL-15, IL-18 and TNFα)[1,11,33] (FIG. 19a). These data suggest that phosphorylated C/EBPβ-Thr217 (or C/EBPβ-Glu217) is required for the expression of the inflammasome structural proteins and byproducts. Further, freshly isolated C/EBPβ-Ala217 liver macrophages from mice treated with CCl$_4$ express an inhibited inflammasome transcriptosome when compared to freshly isolated liver macrophages from C/EBPβ-wt mice treated with CCl$_4$. This included the decreased expression of inflammasome genes (IRF-4, NALP-α, NALP-3, TCAM-2, TRL-1, TRL-3, TRL-5, TRL-6, TRL-7, TRL-8, TRL-9, Nod-1 and Rel) as well as the decreased expression of direct and indirect cytokine inflammasome gene byproducts (IL-1β, IL-6, IL-10, IL-15, IL-18, IL-23α and CXCL-3)[1,11,33] (FIG. 19b). In addition, treatment with CCl$_4$ was associated with the induction of IL-18, active caspase-1 and IL-1β inflammasome protein expression[1] in the livers of C/EBPβ-wt, C/EBPβ-Glu217, and TGFα mice (FIG. 19c).

Figure 20A:
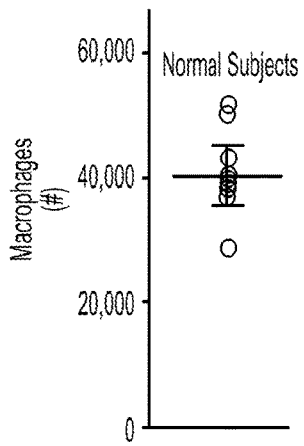
FIGS. 20a & 20c. In TOS patients there was a marked increase in both macrophage infiltration of the liver (~20-fold; 1,004,683+/−140,485 vs. 41,160+/−3,353; P<0.001) (FIG. 20a), and the degree of hepatocyte apoptosis (~30-fold; 32.0+/−4.7% vs. 1.0+/−0.2%; P<0.001) (FIG. 20c), compared to normal subjects (FIGS. 20b & 20d).
Figure 20B:
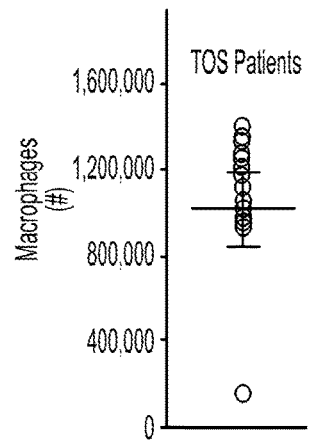
FIGS. 20f, 20h & 20j. Liver macrophages in livers from patients with TOS expressed MyD-88, phosphorylated C/EBPβ-Thr266, and TLR-5 when compared to macrophages in normal livers (FIGS. 20e, 20g & 20i) (P<0.001 for all).
Figure 20C:
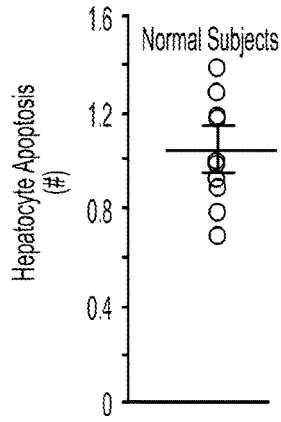
Figure 20D:
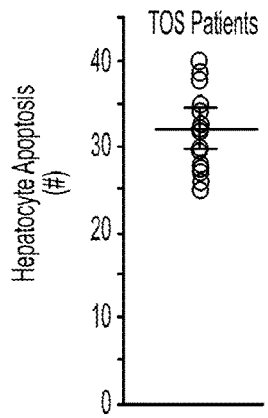

Human Liver Injury Induced by the Toxic Oil Syndrome is Also Characterized by Phosphorylated C/EBPβ-Thr217 Associated with the Inflammasome Complex in Liver Macrophages The Toxic Oil Syndrome (TOS) that occurred in central and northwestern Spain in the summer of 1981 affected approximately 20,000 people, whom were afflicted with acute liver injury. The oxidative stress liver injury was induced in a dose-response manner by the olive oil contaminant 1, 2-dioleoyl ester of 3-(N-phenyl amino)-1, 2-propanediol[34, 35]. Liver biopsies from all 16 patients with TOS that were still available at the Universidad Complutense Medical Center, Madrid, Spain, were analyzed. These patients had a moderately severe acute liver injury as characterized by the elevated ALT and aspartate aminotransferase (AST) with a cholestastic component judging by the increased alkaline phosphatase and total bilirubin, when compared to normal individuals (Table 3). The degree of liver injury by histological analysis in these TOS patients correlated with both macrophage infiltration of the liver (FIG. 20b), the degree of hepatocyte apoptosis (FIG. 20d), compared to control (FIGS. 20a & 20c) and the serum ALT levels (Table 3).

TABLE 3

Baseline demographic and clinical liver tests in subjects with Toxic Oil Syndrome (TOS). The values for serum aminotransferase (ALT; normal up to 40 IU/ml); aspartate aminotransferase (AST; normal up to 35 IU/ml); alkaline phosphatase (Alk. Phosphatase; normal up to 126 IU/ml); and total bilirubin (T. Bilirubin; normal up to 1.2 mg/dL) were increased in this cohort of patients afflicted by Toxic Oil Syndrome (N = 16). Values shown are mean (SE) or % as well as (95% Confidence Intervals (CI)).

| Parameters | Mean (SE) or Numbers (%) | 95% CI |
|---|---|---|
| Age (years) | 37.7 (3.7) | 30.0 to 45.5 |
| Gender (male) | 8 (50%) | N/A |
| ALT (IU/mL) | 277 (50) | 171 to 382 |
| AST (IU/mL( | 138 (20) | 94 to 181 |
| Alk. Phosphatase (IU/mL) | 454 (89) | 264 to 644 |
| T. bilirubin (mg/dL) | 2.5 (0.8) | 0.9 to 4.1 |

Figure 20E:
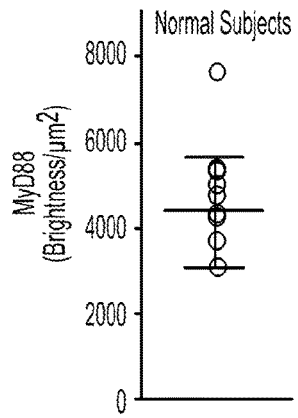
Figure 20F:
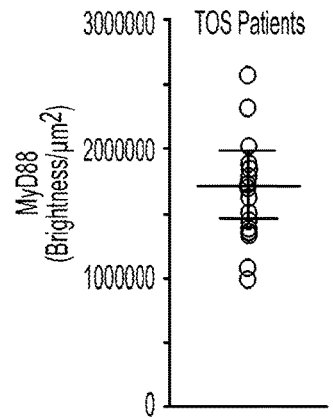
Figure 20G:
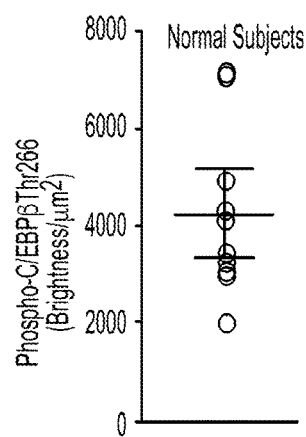
Figure 20H:
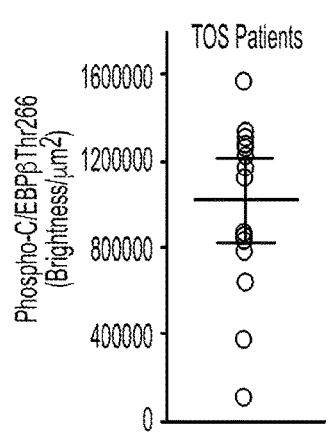
Figure 20I:
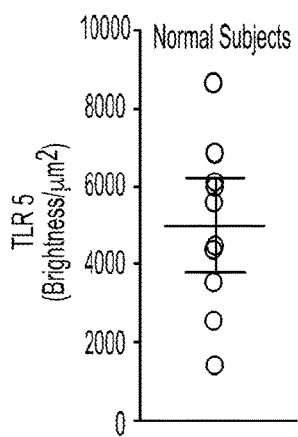
Figure 20J:
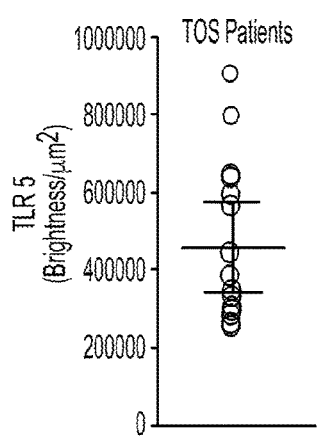

Because TOS is characterized by oxidative stress that results in an acute inflammatory liver injury, whether the livers of TOS afflicted patients had similar features to the $CCl_4$ animal models with acute inflammatory liver injury was analyzed. Liver macrophages, characterized by the expression of specific markers as described above, in livers from patients with TOS expressed phosphorylated C/EBPβ-Thr266 (the exact homologue of mouse Thr217) when compared to macrophages in normal livers (FIGS. 20g & 20h). It was found that the TOS livers have increased markers characteristic of the activated inflammasome, MyD-88 and TLR-5 (FIGS. 20f & 20j) when compared to macrophages in normal livers (FIGS. 20e & 20i).

Discussion

In these studies, the inventors found a novel role of phosphorylated C/EBPβ-Thr217 in the activation of the inflammasome in liver macrophages, resulting in amplification of the liver injury induced by $CCl_4$ or by Fas-L. C/EBPβ-Thr217 phosphorylation is required for macrophage infiltration of the liver after a liver injury induced in mice by the oxidative stress hepatotoxin $CCl_4$ or by Fas-L, and for macrophage activation in primary liver macrophage cultures (stimulated by TGFα, an inducer of C/EBPβ-Thr217 phosphorylation[18]).

Remarkably, blocking the phosphorylation of C/EBPβ-Thr217 by expressing a dominant negative non-phosphorylatible C/EBPβ-Ala217 transgene in mice or by administering an inhibitory peptide of C/EBPβ phosphorylation to C/EBPβ-wt mice prevented the liver injury induced by $CCl_4$ or by Fas-L. Inhibiting the phosphorylation of C/EBPβ-Thr217 also ameliorated macrophage liver infiltration, expression and activation of the inflammasome multiprotein complex as well as the polarization of pro-inflammatory liver macrophages. It was previously shown that spleen macrophages in vivo in C/EBPβ-Ala217 transgenic mice had increased caspase 3 expression (suggestive of activated apoptosis pathways) compared to control mice[28]. However, the inventors do not find any decrease in liver macrophage numbers in C/EBPβ-Ala217 transgenic mice compared to control mice (FIG. 15a), strongly suggesting that in the liver, unlike in the spleen, there is no increased apoptosis of C/EBPβ-Ala217 macrophages.

Specifically, phosphorylation of C/EBPβ-Thr217 in liver macrophages was required for stimulating the expression of the multiprotein complex inflammasome signal 1 (NFκB, IRF8, the adaptor protein MyD88 and TLR4) and of the inflammasome signal 2 pathway (NALP3, TLR5, IL-1R1 and the adaptor protein ASC)[1, 11, 33] Phosphorylated C/EBPβ-Thr217, but not unphosphorylated C/EBPβ-Thr217, was also found to be physically associated with the inflammasome multiprotein complex signal 1 and signal 2.

The central component of an inflammasome is a member of the NALP family, and this protein associates with the adaptor protein apoptosis-associated speck-like protein (ASC), which in turn recruits pro-inflammatory-caspase precursors (such as pro-caspase-1)[36] NALP3, which the inventors found in their model of inflammasome activation in liver macrophages, is able to form inflammasomes while mutations in the gene that encodes NALP3 (CIAS1) cause several auto-inflammatory disorders, indicating its physiological relevance[36].

An acute oxidative stress liver injury with $CCl_4$ in the phosphorylated mimic C/EBPβ-Glu217 mice induced the expression of liver macrophage inflammasome genes (ASC, IRF-1, IRF-4 IRF-5, TCAM-2, TRL-6, TRAF-6, Myo-D88, Nod-1 and Rel) as well as the increased gene expression of direct and indirect cytokine inflammasome byproducts of liver macrophages (IL-1β, IL-6, IL-10, IL-15, IL-18, IL-23α and CXCL-3), a hallmark of inflammasome activation[1, 11, 33, 37] In contrast, freshly isolated nonphosphorylatable C/EBPβ-Ala217 liver macrophages from mice treated with $CCl_4$ expressed an inhibited inflammasome transcriptosome when compared to freshly isolated liver macrophages from C/EBPβ-wt mice treated with $CCl_4$. This included the decreased expression of inflammasome genes (IRF-4, NALP-α, NALP-3, TCAM-2, TRL-1, TRL-3, TRL-5, TRL-6, TRL-7, TRL-8, TRL-9, Nod-1 and Rel) as well as the decreased gene expression of direct and indirect cytokine inflammasome byproducts (IL-1β, IL-6, IL-10, IL-15, IL-18, IL-23α and CXCL-3).

The C/EBPβ-Ala217 mutant functions as a trans-dominant negative of the C/EBPβ-Thr217 phosphorylation[21]. In contrast, the C/EBPβ-Glu217 mutant functions as a trans-dominant positive of the C/EBPβ-Thr217 phosphorylation[18]. In liver injury, phosphorylation of C/EBPβ-Thr217 in macrophages may stimulate macrophage proliferation/survival as reported for the Anthrax lethal toxin[23] and/or facilitates migration to and direct destruction or phagocytosis of the injured hepatocytes. $CCl_4$ increased the liver macrophage infiltration by ~20-fold, while the macrophage stimulating factor TGFα in transgenic mice, which lack hepatocyte injury, did not increase macrophage liver infiltration. Macrophage infiltration is also observed in the livers of animals treated acutely with Fas-L, suggesting that regardless of the mechanisms of liver injury, the stimulation of C/EBPβ-Thr217 phosphorylation in macrophages modulates the infiltration of the liver by these cells.

The Fas-L experiments are physiologically relevant since significant elevations of soluble Fas-L occur in patients with drug-induced liver injury or alcoholic liver disease[38, 39]. Acute FasL administration (acting on TNF superfamily receptors) induced greater macrophage infiltration, and liver injury in the phosphorylation mimic C/EBPβ-Glu217 transgenic mice. Mice expressing the C/EBPβ-Ala217 transgene were refractory to development of liver injury by Fas-L.

Modulation of macrophage activity by ablation also indicated the essential role of phosphorylated C/EBPβ-Thr217 in macrophages for the induction of liver injury after hepatotoxin exposure. The inventors have reported that amplification of toxic liver injury is mediated by macrophages since TLR-4 ko mice were resistant to hepatotoxins and that reconstitution of bone marrow irradiated TLR-4 ko mice with TLR-4[+/+] macrophages conferred susceptibility of these animals to hepatotoxins[4]. More recently, the role of macrophages has been confirmed in toxic liver injury using macrophage ablation[5], in an experimental alcoholic liver injury model using an IL-1 receptor antagonist[6], and in LPS/D-galactosamine induced liver injury using Adenosine-$_{2A}$ (A$_{2A}$) receptor-ko mice[7]. Adenosine is required for sustained inflammasome activation via the A2A receptor and the HIF-1α pathway[7]. In addition, both A$_{2A}$ adenosine receptors and C/EBPβ are required for IL-10 production by macrophages exposed to *Escherichia coli*[40], suggesting a potential convergence of phosphorylated C/EBPβ-Thr217 and the A$_{2A}$ signaling pathways in activated liver macrophages.

Therefore, the studies presented here characterized phosphorylated C/EBPβ-Thr217 in macrophages as a novel and major signaling pathway in hepatotoxin-induced liver injury. Phosphorylated C/EBPβ-Thr217 (human Thr266) may also play a major role in the macrophage inflammasome in liver injury induced by experimental and human alcoholic and non-alcoholic steatohepatitis (NASH)[1, 41]. The findings presented herewith are consistent with the role of C/EBPβ as a critical signaling protein for macrophages since expression of a dominant inhibitor of C/EBPβ DNA-binding sites[15] or of a targeted deletion of C/EBPβ results in impaired macrophage differentiation[16].

The features of a well characterized acute human oxidative stress liver injury, the Toxic Oil Syndrome (TOS), which was induced by a toxic contaminant, mimics and validates, at least in part, the findings with animal models of acute oxidative stress inflammatory liver injury. The findings in human acute liver injury due to TOS suggest that the findings in cellular and animal models may be applicable to some types of acute liver injury in humans. Studies to further understand these pathways in human acute liver injury may define whether or not phosphorylated C/EBPβ-Thr266 in macrophages is pathogenic in these injuries.

In summary, the findings presented in this example provide a novel signaling mechanism through C/EBPβ-Thr217 (human Thr266) for the inflammasome multiprotein complex activation in liver macrophages as a critical step for the development of liver inflammation and injury[1]. Liver inflammation and injury are major contributors to the morbidity and mortality of acute and chronic liver diseases in humans[1, 2, 3, 41]. Thus, IL-1β receptor antagonists[6], A$_{2A}$ receptor antagonists[7], and small molecule peptido mimetics, as targeted inhibitors of human C/EBPβ-Thr266 phosphorylation, in liver macrophages are potential candidates for the prevention and treatment of inflammatory liver injury.

EXAMPLE 11

High Efficacy of the Therapeutic PEG-30 kDa-peptide in the Bleomycin Mouse Model of Lung Fibrosis Via Various Administration Routes C/EBPβ-wt mice received Bleomycin administration as described above. On day-10, once the fibrotic reaction is established, mice received i) PEG-30 kDa-Lys-DAla-DVal-Asp-NH$_2$ intraperitoneally (IP) 10 μg of peptide linked to PEG, on days 10, 17 and 24); or ii) peptide PEG-30 kDa-Lys-DAla-DVal-Asp-NH$_2$ by inhalation (mean particle size 1.3 m—which reaches efficiently the alveoli-, 800 μg of peptide on days 10, 17 and 24; specific inhalation parameters are shown in Table 2). The peptide was administered for less than 1 hour a day [on days 10, 17, and 21] via nose-only inhalation of the test material aerosol at a nominal concentration of 1.0 mg/L [800 μg/dose]; or iii) peptide PEG-30 kDa-Lys-DAla-DVal-Asp-NH$_2$ by intratracheal instillation (40 μg of peptide on days 10, 17 and 24).

TABLE 2

Aerosol Parameters of the Peptide Administration by Inhalation

| Solution Concentration (mg/ml) | Pari Disperse Rate (ml/min) | Pari Flow Rate (L/min) | Aerosol Concentration (mg/L) | RMV (L/min) | Peptoid Inhaled Per day (ug) | Exposure Duration Per Day (min) | Consumption per day (ml) | Consumption per day (mg) |
|---|---|---|---|---|---|---|---|---|
| 31 | 0.25 | 5.5 | 1.00 | 0.022 | 800 | 36.3 | 12.1 | 374.7 |

Control groups received sterile water instead of Bleomycin; peptide IP; peptide by inhalation; or peptide by intratracheal instillation. Animals were sacrificed on day 27. The left lung was inflated with fixative, analyzed by trichrome stain and quantified in its entirety by the Odyssey Visualization microscopy software protocol to minimize analytical errors as described previously (Ramamoorthy et al., 2009, American Journal of Physiology, Endocrinology and Metabolism 297: e392-401). The right lung was snap frozen in liquid nitrogen and used for IMH, immunoblots and qRT-PCR. Treatment with the PEG-30 kDa-peptide IP, intratracheal instillation of the peptide (positive control), or the peptide by inhalation markedly reduced the degree of lung fibrosis; the expression of α-SMA (a marker of activated myofibroblasts), which was co-localized with C/EBPβ-Thr217 phosphorylation.

Figure 25A:
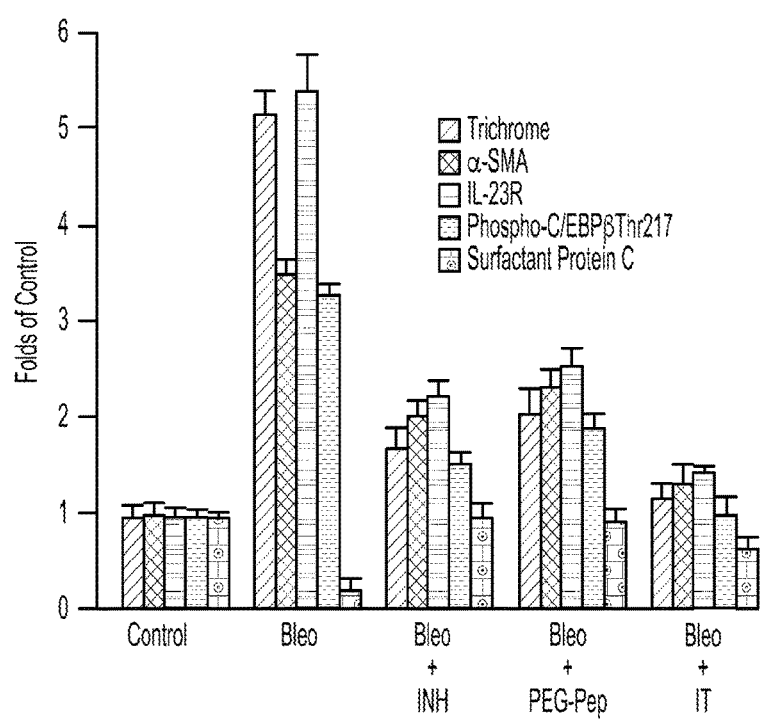
FIGS. 25a-25b. Treatment with the PEG-30 kDa-peptide IP, Intratracheal Instillation of the peptide (positive control), or the peptide by inhalation markedly reduced the degree of lung fibrosis; the expression of α-SMA (a marker of activated myofibroblasts), which was co-localized with C/EBPβ-Thr217 phosphorylation. In addition, all treatments decreased lung inflammation as determined by the expression of IL-23R (a marker of Th-17 cells). Bleomycin increased lung fibrosis by >5-fold compared to control animals. In contrast, animals receiving PEG-30 kDa-peptide or the peptide by inhalation had a decrease in lung fibrosis of ~60% in just 14-day treatment with 3 doses on days 10, 17 and 24) (P<0.001). As expected, Intratracheal instillation (therapeutic positive control) had an outstanding efficacy, with only small differences with control animals (P<0.001). The peptide also decreased Th-17 inflammation (probably, an important component of IPF inflammation), judging by the decreased expression of IL-23R. C/EBPβ-wt mice that received the PEG-30 kDa-peptide or the peptide by inhalation had less lung injury than control C/EBPβ-wt mice after Bleomycin treatment, judging from the essentially normal surfactant protein-C (SFPC) expression by quantitative IMH (P<0.001 (FIG. 25a). In agreement with the quantitative IMH, both collagen α1 (a major ECM gene) and TGFβ1 (a fibrogenic cytokine) were decreased by the three peptide formulations as determined by RT-PCR.
Figure 25B:
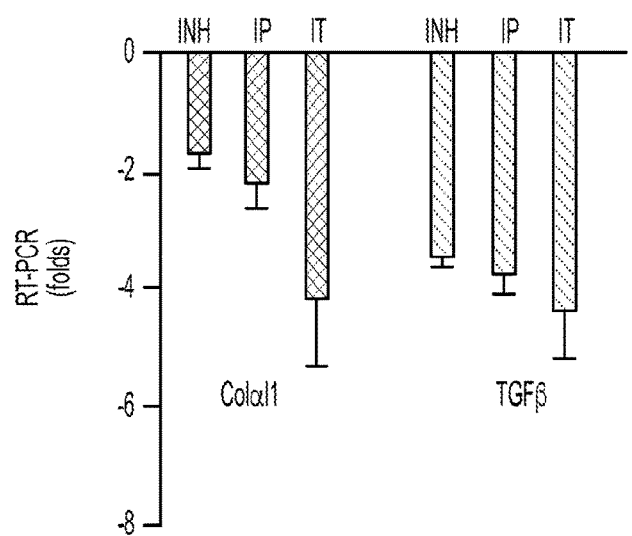

In addition, all treatments decreased lung inflammation as determined by the expression of IL-23R (a marker of Th-17 cells). Bleomycin increased lung fibrosis by >5-fold compared to control animals. In contrast, animals receiving PEG-30 kDa-peptide or the peptide by inhalation had a decrease in lung fibrosis of ~60% in just 14-day treatment with 3 doses on days 10, 17 and 24) (P<0.001) (FIG. 25*a*). Intratracheal instillation (therapeutic positive control) had an outstanding efficacy, with only small differences with control animals (P<0.001) (FIGS. 25A-25*b*). The peptide also decreased Th-17 inflammation (probably, an important component of IPF inflammation (69)), judging by the decreased expression of IL-23R (68) (FIG. 25*a*). In agreement with the quantitative IHC, both collagen α 1 (a major ECM gene (5)) and TGFβ1 (a fibrogenic cytokine (5)) were decreased by the three peptide formulations as determined by RT-PCR (FIG. 25*b*).

Figure 26:
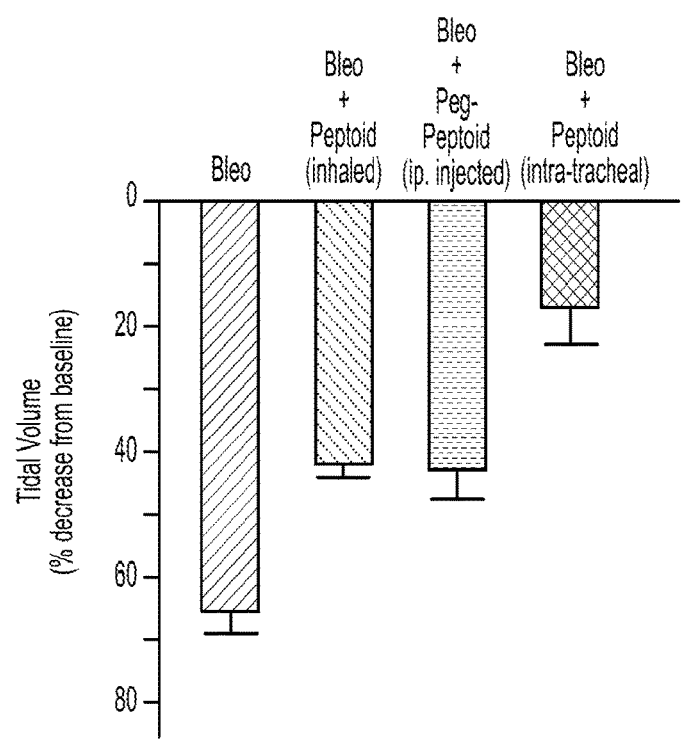
FIG. 26. Treatment with the PEG-30 kDa-peptide IP, Intratracheal Instillation of the peptide (positive control), or the peptide by inhalation as described in FIGS. 25a-25b. In spite of the short 14-day treatment, all treatments improved the Tidal Volume by >35% (P<0.01).
Figure 27:
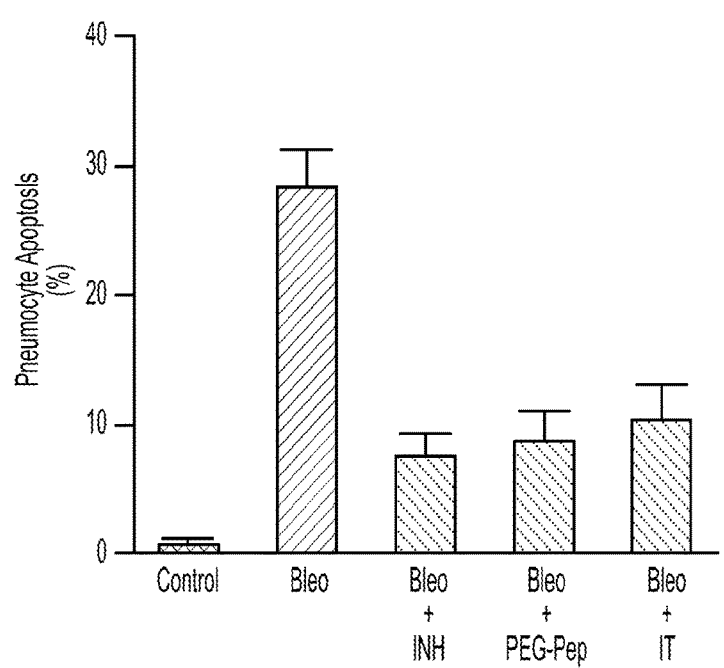
FIG. 27 illustrates that C/EBPβ-wt mice that received the PEG-30 kDa-peptide or the peptide by inhalation had less lung injury than control C/EBPβ-wt mice after Bleomycin treatment, judging by the remarkable inhibition in lung alveolar epithelial cell apoptosis (~60%), (P<0.005).

Thus, higher and prolonged doses in patients (corrected by FDA Tables and the Physiologically Based-PK analysis for patients with IPF) may be even more efficacious. In spite of the short 14-day treatment, all treatments improved the Tidal Volume by >35% (P<0.01) (FIG. 26). C/EBPβ-wt mice that received the PEG-30 kDa-peptide or the peptide by inhalation had less lung injury than control C/EBPβ-wt mice after Bleomycin treatment, judging from the essentially normal surfactant protein C (SFPC) expression by quantitative IHC (P<0.001) (FIG. 25*a*) and by the remarkable inhibition in lung alveolar epithelial cell apoptosis (~60%), (P<0.005) (FIG. 27).

EXAMPLE 12

Figure 28:
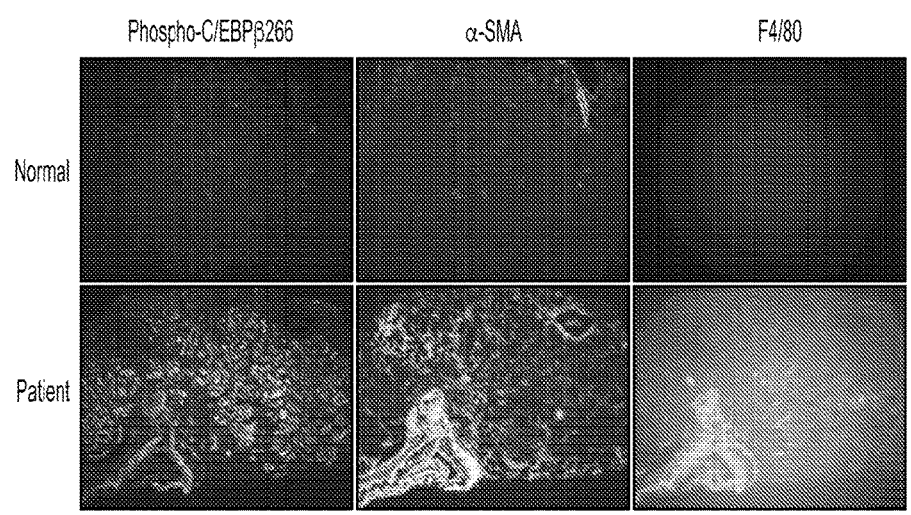
FIG. 28. Representative Immunohistochemistry of a kidney biopsy from a patient with crescent glomerulonephritis. As documented for liver and lung inflammation and fibrosis, kidney glomerulonephritis has a marked increase in activated myofibroblasts (α-SMA) and an enhanced macrophage inflammatory reaction (F4/80). These cells were positive for C/EBPβ-266 indicating the high feasibility of targeting kidney inflammation and fibrosis with the PEG-30 kDa-peptide.

Marked Increase in the Number of Activated Myofibroblasts and Expression of Phospho-C/EBPβThr266 (Human Homologue of Mouse Phospho-C/EBPβThr217) and Inflammation with Activated Macrophages in Kidney Fibrosis Kidney biopsies from three patients with kidney fibrosis secondary to glomerulonephritis were analyzed. These biopsies showed extensive glomerular fibrosis with a marked increase in the number of activated myofibroblasts (indicated by the expression of α-SMA) as well as the marked expression of Phospho-C/EBPβThr266 (human homologue of mouse Phospho-C/EBPβThr217) and inflammation with activated macrophages (indicated by F4/80) (FIG. 28).

These findings indicate that the mechanisms leading to tissue fibrosis are the same in liver, lung and kidney, and point to a common mechanism involving activated myofibroblasts inflammatory macrophages and Phospho-C/EBPβThr266 probably in all tissue fibrotic diseases. Therefore, the treatment of kidney fibrosis can also be feasible by targeting Phospho-C/EBPβ-Thr266 with the PEG-30 kDa-peptide of the invention.

EXAMPLE 13

The Intermediate Molecule Released from the PEG30 kDa-Mpr-peptide In Vivo is Pharmacologically Active The following shows the structure of the testing peptide, of which one of the lead molecules is the Mpr-linked PEG peptide (aka PEG-30 kDa-Mpr-peptide).

| Test Article | Physical Form | MW |
|---|---|---|
| Ac-Lys-DAla-DVal-Asp-NH2 | solid | 473.52 |
| Mpr-Lys-DAla-DVal-Asp-NH2 (aka PEG-30 kDa-Mpr peptide) | solid | 518 |
| PEGylated-peptide 361332 | solid | ~30 KDa |

The chemical structure of PEGylated-peptide 361332 is presented below:

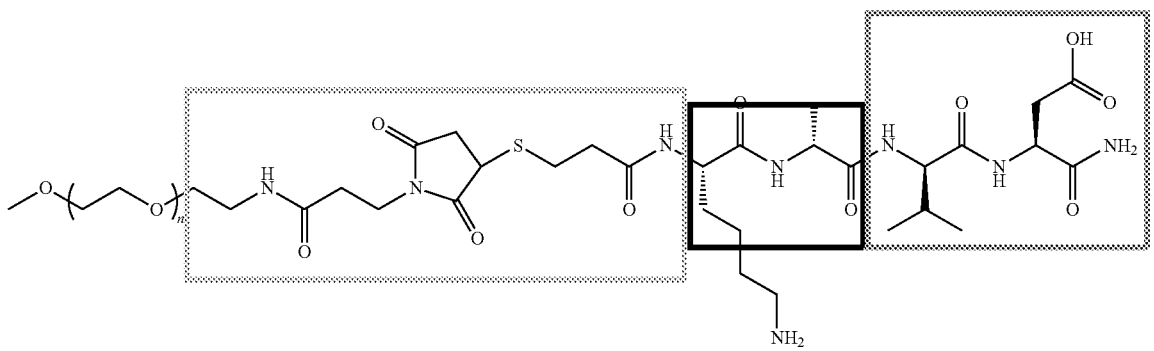

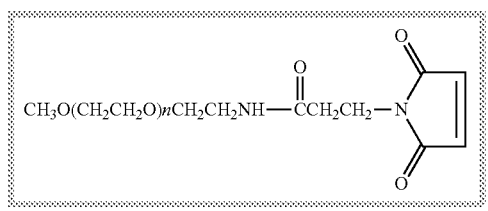
MPEG-Maleimide

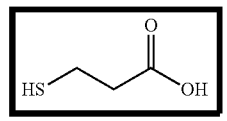
Mercaptopropionic acid linker (Mpr)

peptide w/linker

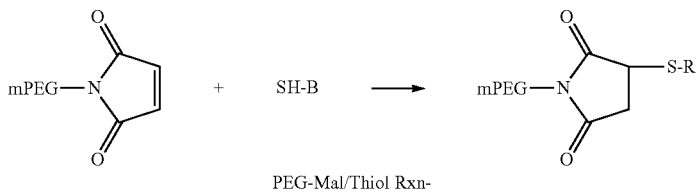
PEG-Mal/Thiol Rxn-

Studies using the PEGylated-peptide 361332 are provided

| Test Article | Admin. Route | Mouse Strain | Number of Animals | Dose (mg/kg)[a] | Samples Collected | Collection Time Points |
|---|---|---|---|---|---|---|
| PEGylated-peptide 361332 | IV | CD-1 | 4 | 7.5 | Plasma, Liver | 4, 8, 24 and 48 hours |

[a] Dose reflects peptide equivalent of 7.5 mg/kg; n = 1 mouse per time point for this pilot study.

Levels of Peptide and MPR-Intermediate in Plasma Samples

| Time | Ac-Lys-Dala-Dval-Asp-NH2 Conc. (ng/mL) | Mpr-Lys-DAla-DVal-Asp-NH2 Conc. (ng/mL) |
|---|---|---|
| 4 | 65.8 | 1291 |
| 8 | 79.2 | 900 |
| 24 | 70.2 | 921 |
| 48 | 67.6 | 1523 |

The Mpr-peptide can also be a therapeutic as an additional formulation since it releases the active peptide. Therefore, it could be administered as an alternative formulation for the treatment of various tissue fibrotic diseases.

REFERENCES FOR LIVER INFLAMMATION AND FIBROSIS

1. Bravo R, Frank R, Blundell P A and MacDonald-Bravo H. Cyclin/PCNA is the auxiliary protein of DNA polymerase-delta. Nature 326: 515-7, 1987.
2. Buck M, Turler H and Chojkier M. LAP (NF-IL6), a tissue-specific transcriptional activator, is an inhibitor of hepatoma cell proliferation. EMBO J 13: 851-860, 1994.
3. Buck M, Poli V, Chojkier M and Hunter T. Phosphorylation of rat serine 105 or mouse threonine 217 in C/EBPβ is required for hepatocyte proliferation induced by TGFα. Mol Cell 4:1087,1999.
4. Buck M, Poli V, Hunter T and Chojkier M. C/EBPβ phosphorylation by RSK creates a functional XEXD caspase inhibitory box critical for cell survival. Mol Cell 8: 807-16, 2001.
5. Buck M, Zhang L, Hunter T and Chojkier M. Nuclear export of phosphorylated C/EBPβ mediates the inhibition of albumin expression by TNF. EMBO J 20: 6712-23, 2001.
6. Buck M, Chojkier M. Signal Transduction in the Liver. Hepatology 37: 731-8, 2003.
7. Buck M, Chojkier M. A ribosomal S6K-mediated signal to C/EBPβ is critical for the development of liver fibrosis. PLOS One 2: e1372, 2007.
8. Buck M, Chojkier M. C/EBPβ phosphorylation rescues macrophage dysfunction and apoptosis induced by anthrax lethal toxin. Am J Physiol Cell Physiol 293: C1788-96, 2007.
9. Buck M and Chojkier M. C/EBPβ Associates With Caspase 8 Complex Proteins and Modulates Apoptosis in Hepatic Stellate Cells. J Clin Gastroenterol 41: S295-99, 2007.
10. Buck M. Direct infection and replication of naturally occurring hepatitis C virus genotypes 1, 2, 3, and 4 in normal human hepatocyte cultures. PLOS One 3: 2660, 2008.
11. Buck M and Chojkier M. C/EBPβ-Thr217 phosphorylation Signaling Contributes to the Development of Lung Injury and Fibrosis in Mice. PLOS One 2011.
12. Castilla R, R Gonzalez, D Fouad, E. Fraga and J Muntane. Dual Effect of Ethanol on Cell Death in Primary Culture of Human and Rat Hepatocytes. Alcohol & Alcoholism 39, 290-6, 2004.
13. Chung R and Podolsky D. Cirrhosis and its Complications. In: Harrison's Principles of Internal Medicine, New York: McGraw-Hill, 2005, p. 1754-1767
14. Chojkier M. Regulation of liver-specific gene expression. In: Progress in Liver Diseases, edited by Boyer J and Ockner R. Orlando: W.B. Saunders, 1995, p. 37-61.
15. Chojkier, M. Regulation of collagen gene expression. In Liver growth and repair. 430-50; 1998.
16. Chojkier M. Troglitazone and liver injury: in search of answers. *Hepatology* 41: 237-246, 2005. PMID: 15657914
17. Descombes P, Chojkier M, Lichtsteiner S, Falvey E and Schibler U. LAP, a novel member of the C/EBP gene family, encodes a liver-enriched transcriptional activator protein. Genes Dev 4: 1541-51, 1990.
18. Friedman J R, Larris B, Le P P, Peiris T H, Arsenlis A, Schug J, Tobias J W, Kaestner K H, Greenbaum L E. Orthogonal analysis of C/EBPβ targets in vivo during liver proliferation. Proc Natl Acad Sci USA. 2004; 101 (35):12986-91.
19. Friedman S L. Molecular regulation of hepatic fibrosis, an integrated cellular response to tissue injury. *J Biol Chem* 275: 2247-2250, 2000. PMID: 10644669
20. Friedman S L and Bansal M B. Reversal of hepatic fibrosis—fact or fantasy? *Hepatology* 43: S82-S88, 2006. PMID: 16447275.
21. Gewolb J. Protecting the Liver From Itself. Science Now 4, 2001.
22. Gyrd-Hansen M & Pascal Meier. IAPs: from caspase inhibitors to modulators of NF-κB, inflammation and cancer Nature Reviews Cancer 10, 561-574 (August 2010) doi: 10.1038/nrc2889
23. Houglum K, Lee K S and Chojkier M. Proliferation of hepatic stellate cells is inhibited by phosphorylation of CREB on Serine 133. J Clin Invest 99: 1322, 1997.
24. Iredale J. Stellate cell behavior during resolution of liver injury. *Semin Liv Dis* 21: 427-436, 2001.
25. Jimenez W, Pares A, Caballeria J, Heredia D, Bruguera M, Torres M, Rojkind M and Rodes J. Measurement of fibrosis in needle liver biopsies: evaluation of a colorimetric method. *Hepatology* 5: 815-818, 1985. PMID: 4029893
26. Kim K, Keiichirou Morimura, Yatrik Shah, Qian Yang, Jerrold M. Ward and Frank J. Gonzalez Spontaneous development of liver tumors in the absence of the bile acid receptor farnesoid X receptor. Carcinogenesis (2007) 28 (5): 940-946. doi: 10.1093/carcin/bgl249.
27. Lee K S, Buck M, Houglum K and Chojkier M. Activation of hepatic stellate cells by TGFα and collagen type I is mediated by oxidative stress through c-myb expression. *J Clin Invest* 96: 2461-2468, 1995. PMID #7593635.
28. McKnight S L. McBindall—a better name for CCAAT/enhancer binding proteins? *Cell* 107: 259-261, 2001.
29. Magzoub, M.; Gräslund, A. Cell-penetrating peptides. Q Rev Biophys 37; 147-195; 2004.
30. Nakajima T, Kishimoto T, Akira S. Phosphorylation at threonine-235 by a ras-dependent mitogen-activated protein kinase cascade is essential for transcription factor NF-IL6. PNAS. 90:2207-11. 1993

31. Patsch W, T Tamai, and G Schonfeld. Effect of fatty acids on lipid and apoprotein secretion and association in hepatocyte cultures. J Clin Invest. 1983; 72: 371-8.
32. Reducing Risks, Promoting Healthy Life. In: The World Health Report 2002, Geneva: World Health Organization, 2002, p. 1-230.
33. Report 04-5491. Executive Summary. In: Action Plan for Liver Disease Research, NIH, 2004, p. 1-6.
34. Report 04-5491. Liver Cancer. Action Plan for Liver Disease Research. 137-143. 2004. U.S. Department of Health and Human Services, NIH.
35. Report 04-5491. Chapter 2. In: Action Plan for Liver Disease Research, NIH, 2004, p. 39-43.
36. Rojas M, Lin Y Z. Controlling EGF-stimulated Ras activation in intact cells by a cell-permeable peptide mimicking phosphorylated EGF receptor. J Biol Chem. 271:27456-61.1996.
37. Roy S K, Hu J, Meng Q, Shapiro P S, Reddy S P, Platanias L C, Lindner D J, Johnson P F, Pritchard C, Pages G, Pouyssegur J and Kalvakolanu D V. MEKK1 plays a critical role in activating the transcription factor C/EBP-beta-dependent gene expression in response to IFN-gamma. *Proc Natl Acad Sci USA* 99: 7945-7950, 2002. PMID: 12048245
38. Rudolph K, Chang S, Millard M, Schreiber-Agus N and DePinho R. Inhibition of experimental liver cirrhosis in mice by telomerase gene delivery. *Science* 287: 1253-1258, 2000. PMID: 10678830
39. Sato, A. K.; Viswanathan, M.; Kent, R. B.; Wood, C. R. Therapeutic peptides: technological advances driving peptides into development. Curr. Opin. Biotech. 17; 638-42; 2006.
40. Trautwein C, Caelles C, van der Geer P, Hunter T, Karin M and Chojkier M. Transactivation by NF-IL6/LAP is enhanced by phosphorylation of its activation domain. Nature 364: 544-547, 1993.
41. Trautwein C, Karin M, Hunter T and Chojkier M. PKA and C site-specific phosphorylations of LAP modulate its binding affinity to DNA-recognition elements. J Clin Inv 93: 2554-61, 1994.
42. Veronese, F. M. PEGylation, successful approach to drug delivery. Drug Disc Today 10; 1451-8; 2005.
43. Wegner M, Cao Z and Rosenfeld M G. Calcium-regulated phosphorylation within the leucine zipper of C/EBP. *Science* 256: 370-373, 1992. PMID: 1314426
44. Yamamoto K K, Gonzalez G A, Biggs W H, III and Montminy M R. Phosphorylation-induced binding and transcriptional efficacy of nuclear factor CREB. *Nature* 334: 494-498, 1988. PMID: 290047.
45. Chen R H, Abate C, Blenis J. Phosphorylation of the c-Fos transrepression domain by mitogen-activated protein kinase and 90-kDa ribosomal S6 kinase. Proc Natl Acad Sci USA. 1993 Dec. 1; 90 (23):10952-6.
46. Manning G, Whyte D B, Martinez R, Hunter T, Sudarsanam S. The protein kinase complement of the human genome. Science. 2002; 298:1912-34.
47. Jhappan C, C. Stahle, R. N. Harkins, N. Fausto, G. H. Smith and G. T. Merlino. 1990. TGF overexpression in transgenic mice induces liver neoplasia and abnormal development of the mammary gland and pancreas. Cell 61: 1137-1146.
48. Henzel W J, Watanabe C, Stults J T. Protein identification: the origins of peptide mass fingerprinting. J Am Soc Mass Spectrom. 2003; 14(9):931-42.
49. Olsen J V, Ong S E, Mann M. Trypsin cleaves exclusively C-terminal to arginine and lysine residues. Mol Cell Proteomics. 2004; 3(6):608-14.
50. Sherman, Nicholas E.; Kinter, Michael (2000). Protein sequencing and identification using tandem mass spectrometry. New York: John Wiley.
51. Wible B. A., Peter Hawryluk, Eckhard Ficker, Yuri A. Kuryshev, Glenn Kirsch, Arthur M. Brown. HERG-Lite: A novel comprehensive high-throughput screen for drug-induced hERG risk. Journal of Pharmacological and Toxicological Methods 52 (2005) 136-145.
52. Johnson S. A., Tony Hunter. Kinomics: methods for deciphering the kinome. Nature Methods 2, 17-25 (2005).
53. Sinz M, Gillian Wallace, and Jasminder Sahi. Current Industrial Practices in Assessing CYP450 Enzyme Induction: Preclinical and Clinical. AAPS J. 2008; 10(2): 391-400.
54. Bernardi M, Calandra S, Colantoni A, Trevisani F, Raimondo M L, Sica G, Schepis F, Mandini M, Simoni P, Contin M, Raimondo G. Q-T interval prolongation in cirrhosis: prevalence, relationship with severity, and etiology of the disease and possible pathogenetic factors. Hepatology. 1998; 27(1):28-34.
55. Baker M P, and Jones T D. Identification and removal of immunogenicity from therapeutic proteins. Curr Opin Drug Discov Devel. (2007) 10:219.
56. Perry L C A, Jones T D, and Baker M P. New approaches to prediction of immune responses to therapeutic proteins during pre-clinical development. Drugs R D (2008) 9 (6): 385.

REFERENCES CITED FOR LUNG INFLAMMATION AND FIBROSIS

1. Akira S, Isshiki H, Sugita T, Tanabe O, Kinoshita S, Nishio Y, Nakajima T, Hirano T and Kishimoto T. A nuclear factor for IL-6 expression (NF-IL6) is a member of a C/EBP family. *EMBO J* 9: 1897-1906, 1990.
2. Barron L and Wynn T A. Fibrosis is regulated by Th2 and Th17 responses and by dynamic interactions between fibroblasts and macrophages. *Am J of Phys-Gastroint. and Liver Physiology* 300: 723-728, 2011.
3. Bedossa P, Houglum K, Trautwein C, Holstege A and Chojkier M. Stimulation of collagen 1(I) gene expression is associated with lipid peroxidation in hepatocellular injury. A link to tissue fibrosis? *Hepatology* 19: 1262-1271, 1994.
4. Berberich-Siebelt F, Berberich I, Andrulis M, Santner-Nanan B, Jha M K, Klein-Hessling S, Schimpl A and Serfling E. SUMOylation interferes with CCAAT/Enhancer-binding protein-mediated c-myc repression, but not IL-4 activation in T-cells. *J Immunol* 176: 4851, 2006.
5. Bravo R, Frank R, Blundell P A and MacDonald-Bravo H. Cyclin/PCNA is the auxiliary protein of DNA polymerase-delta. *Nature* 326: 515-517, 1987.
6. Buck M. Targeting ribosomal S-6 kinase for the prevention and treatment of liver injury and liver fibrosis. *Drug News Perspect* 21: 301-306, 2008.
7. Buck M and Chojkier M. A ribosomal S-6 kinase-mediated signal to C/EBP is critical for the development of liver fibrosis. *PLOS One* 2: e1372, 2007.
8. Buck M and Chojkier M. C/EBP(beta) phosphorylation rescues macrophage dysfunction and apoptosis induced by anthrax lethal toxin. *Am J Physiol Cell Physiol* 293: C1788-C1796, 2007.
9. Buck M and Chojkier M. Signal Transduction in the Liver: C/EBP Modulates Cell Proliferation and Survival. *Hepatology* 37: 731-738, 2003.
10. Buck M and Chojkier M. Muscle wasting and dedifferentiation induced by oxidative stress in a murine model of cachexia is prevented by inhibitors of nitric oxide synthesis and antioxidants. *EMBO J* 15:1753-65, 1996.

11. Buck M and Chojkier M. C/EBP-Thr217 phosphorylation Signaling Contributes to the Development of Lung Injury and Fibrosis in Mice. *PLOS One* 2011.

12. Buck M, Poli V, Hunter T and Chojkier M. C/EBP phosphorylation by RSK creates a functional XEXD caspase inhibitory box critical for cell survival. *Mol Cell* 8: 807-816, 2001.

13. Buck M, Poli V, van der Geer P, Chojkier M and Hunter T. Phosphorylation of rat serine 105 or mouse threonine 217 in C/EBP is required for hepatocyte proliferation induced by TGF. *Mol Cell* 4: 1087-92, 1999.

14. Buck M, Turler H and Chojkier M. LAP (NF-IL6), a tissue-specific transcriptional activator, is an inhibitor of hepatoma cell proliferation. *EMBO J* 13: 851-860, 1994.

15. Buck M, Zhang L, Hunter T and Chojkier M. Nuclear export of phosphorylated C/EBP mediates the inhibition of albumin expression by TNF. *EMBO J* 20: 6712-6723, 2001.

16. Chojkier M and Fierer J. D-galactosamine hepatotoxicity is associated with endotoxin sensitivity and mediated by lymphoreticular cells in mice. *Gastroenterology* 88: 115-121, 1985.

17. Chojkier M. Regulation of collagen gene expression. In: Liver growth and repair, edited by Strain A and Diehl A. London: Chapman & Hall, 1998, p. 430-450.

18. Crystal R G, Bitterman P B, Mossman B, Schwarz M I, Sheppard D, Almasy L, Chapman H A, Friedman S L, King T E, Jr., Leinwand L A, Liotta L, Martin G R, Schwartz D A, Schultz G S, Wagner C R and Musson R A. Future Research Directions in IPF: *Am J Respir Crit Care Med* 166: 236-46, 2002.

19. Cutroneo K R, White S L, Phan S H and Ehrlich H P. Therapies for bleomycin induced lung fibrosis through regulation of TGF-beta1 induced collagen gene expression. *Journal of Cellular Physiology* 211: 585-589, 2007.

20. Degryse A L, Xu X C, Tanjore H, Polosukhin V V, Jones B, Mc Mahon F B, Ortiz C, Blackwell T S and Lawson W E. TGF Signaling In Epithelium Regulates Bleomycin Induced Alveolar Injury And Fibroblast Recruitment. *Am J Respir Crit Care Med* 183: A6144, 2011.

21. Descombes P, Chojkier M, Lichtsteiner S, Falvey E and Schibler U. LAP, a novel member of the C/EBP gene family, encodes a liver-enriched transcriptional activator protein. *Genes Dev* 4: 1541-1551, 1990.

22. Fichtner-Fiegl S, Strober W, Kawakami K, Puri R K and Kitani A. IL-13 signaling through the IL-1β receptor is involved in induction of TGF-1 production and fibrosis. *Nature Medicine* 12: 99-106, 2006.

23. Franchi L, Eigenbros T, Munoz-Planillo R and Nunez G. The Inflammasome: A caspase-1 activation platform regulating immune responses and disease pathogenesis. *Nat Immunol* 10: 241, 2009.

24. Garantziotis S, Steele M P and Schwartz D A. Pulmonary fibrosis: thinking outside of the lung. *J Clin Invest* 114: 319-321, 2004.

25. Green D and Reed J. Mitochondria and apoptosis. *Science* 281: 1309-1312, 1998.

26. Hardie W D, Glasser S W and Hagood J S. Emerging concepts in the pathogenesis of lung fibrosis. *Am J Pathol* 175: 3-16, 2009.

27. He W, Zhang L, Ni A, Zhang Z, Mirotsou M, Mao L, Pratt R E and Dzau V J. Exogenously administered secreted frizzled related protein 2 (Sfrp2) reduces fibrosis and improves cardiac function in a rat model of myocardial infarction. *PNAS* 2010.

28. Hilgendorff A, Doerner M, Rawer D, Leick J, Trotter A, Ebsen M, Ruppert C, Günther A, Gortner L and Reiss I. Effects of a recombinant surfactant protein-C-based surfactant on lung function and pulmonary surfactant system in a model of meconium aspiration syndrome. *Crit Care Med* 134: 203-210, 2006.

29. Homer R J, Elias J A, Lee C G and Herzog E. Modern concepts on the role of inflammation in pulmonary fibrosis. *Archives of Pathology & Laboratory Medicine* 135: 780-788, 2011.

30. Houglum K, Lee K S and Chojkier M. Proliferation of hepatic stellate cells is inhibited by phosphorylation of CREB on Serine 133. *J Clin Invest* 99: 1322-1389, 1997.

31. Hu B, Ullenbruch M R, Jin H, Gharaee-Kermani M and Phan S H. An essential role of CCAAT/enhancer binding protein beta in bleomycin-induced pulmonary fibrosis. *J Pathol* 211: 455-462, 2007.

32. Huh J R, Leung M W L, Huang P, Ryan D A, Krout M R, Malapaka R, Chow J, Manel N, Ciofani M, Kim S V, Cuesta A, Santori F R, Lafaille J J, Xu H E, Gin D Y, Rastinejad F and Littman D R. Digoxin and its derivatives suppress Th17 cell differentiation by antagonizing RORγt activity. *Nature* 472: 486-490, 2011.

33. Jakubzick C, Choi E S, Joshi B H, Keane M P, Kunkel S L, Puri R K and Hogaboam C M. Therapeutic Attenuation of Pulmonary Fibrosis Via Targeting of IL-4- and IL-13-Responsive Cells. *J Immunol* 171: 2684-2693, 2003.

34. Jenner R G, Townsend M J, Jackson I, Sun K, Bouwman R D, Young R A, Glimcher L H and Lord G M. The transcription factors T-bet and GATA-3 control alternative pathways of T-cell differentiation through a shared set of target genes. *Proc Natl Acad Sci USA* 106: 17876-17881, 2009.

35. Kabelitz D. Expression and function of Toll-like receptors in T lymphocytes. *Curr Opin Imm* 19:39-45, 2007.

36. Kamei Y, Xu L, Heinzel T, Torchia J, Kurokawa R, Gloss B, Lin S C, Heyman R A, Rose D W, Glass C K and Rosenfeld M G. A CBP integrator complex mediates transcriptional activation and AP-1 inhibition by nuclear receptors. *Cell* 85: 403-414, 1996.

37. Karpel J P, Aldrich T K, Mitsudo S and Norin A J. Lung Lymphocytes in Bleomycin-Induced Pulmonary Disease. *Lung* 167: 163-172, 1989.

38. Kelley J. Cytokines of the lung. *American Review of respiratory disease* 141: 765-788, 1990.

39. Kinoshita S M and Taguchi S. NF-IL6 (C/EBPbeta) induces HIV-1 replication by inhibiting cytidine deaminase APOBEC3G. *Proc Natl Acad Sci USA* 105: 15022-15027, 2008.

40. Königshoff M, Kramer M, Balsara N, Wilhelm J, Amarie O V, Jahn A, Rose F, Fink L, Seeger W, Schaefer L, Günther A and Eickelberg O. WNT 1-inducible signaling protein-1 mediates pulmonary fibrosis in mice and is upregulated in humans with idiopathic pulmonary fibrosis. *J Clin Invest* 119: 772-787, 2009.

41. Kowenz-Leutz E, Twamley G, Ansieau S and Leutz A. Novel mechanism of C/EBP beta (NF-M) transcriptional control: activation through derepression. *Genes Dev* 8: 2781-2791, 1994.

42. Lee F, Hagler J, Chen Z and Maniatis T. Activation of the I kappa B alpha kinase complex by MEKK1, a kinase of the JNK pathway. *Cell* 88: 213-222, 1997.

43. Li B, Tournier C, Davis R J and Flavell R A. Regulation of IL-4 expression by the transcription factor JunB during T helper cell differentiation. *EMBO J* 18: 420-432, 1999.

44. Li M, Krishnaveni M S, Li C, Zhou B, Xing Y, Banfalvi A, Li A, Lombardi V, Akbari O, Borok Z and Minoo P. Epithelium-specific deletion of TGF-β receptor type II protects mice from bleomycin-induced pulmonary fibrosis. *Journal of Clinical Investigation* 121: 277-287, 2011.
45. Magzoub M and Graslund A. Cell-penetrating peptides: [corrected] from inception to application. *Q Rev Biophys* 37: 147-195, 2004.
46. Maitra A, Shen F, Hanel W, Mossman K, Tocker J, Swart D and Gaffen S L. Distinct functional motifs within the IL-17 receptor regulate signal transduction and target gene expression. *Proc Natl Acad Sci USA* 104: 7506-7511, 2007.
47. Martinon F, Burns K and Tschopp J. The inflammasome: a molecular platform triggering activation of inflammatory caspases and processing of proIL-beta. *Molecular Cell* 10: 417-426, 2002.
48. Matsusaka T, Fujikawa K, Nishio Y, Mukaido N, Matsushima K, Kishimoto T and Akira S. Transcription Factors NF-IL6 and NF-kappa B Synergistically activate transcription of the inflammatory cytokines, interleukin 6 and interleukin 8. *PNAS* 90: 10193-10197, 1999.
49. McGeachy M J and Cua D J. Th17 Cell Differentiation: The Long and Winding Road. *Immunity* 28: 445-453, 2008.
50. McGuirk P and Mills K H G. Pathogen-specific regulatory T cells provoke a shift in the Th1/Th2 paradigm in immunity to infectious diseases. *Trends Immunol* 23: 450-455, 2002.
51. McKnight S L. McBindall—a better name for CCAAT/enhancer binding proteins? *Cell* 107: 259-261, 2001.
52. Meneghin A and Hogaboam C M. Infectious disease, the innate immune response, and fibrosis. *J Clin Invest* 117: 530-538, 2007.
53. Mombaerts, Peter, Iacomini, John, Johnson, Randall S., Herrup, Karl, Tonegawa, Susumu, and Papaioannou, Va. E. RAG-1-deficient mice have no mature B and T lymphocytes. Cell 68, 869-77. 1992.
54. Moore B B and Hogaboam C M. Murine models of pulmonary fibrosis. *Am J Physiol Lung Cell Mol Physiol* 294: L152-L160, 2008.
55. Mullen A C, High F A, Hutchins A S, Lee H W, Villarino A V, Livingston D M, Kung A L, Cereb N, Yao T P, Yang S Y and Reiner S L. Role of T-bet in Commitment of TH1 Cells Before IL-12-Dependent Selection. *Science* 292: 1907-1910, 2001.
56. Murray P J and Wynn T A. Protective and pathogenic functions of macrophage subsets. *Nat Rev Immunol* 11: 723-737, 2011.
57. Nakajima T, Kinoshita S, Sasagawa T, Sasaki K, Naruto M, Kishimoto T and Akira S. Phosphorylation at threonine-235 by a ras-dependent mitogen-activated protein kinase cascade is essential for transcription factor NF-IL6. *Proc Natl Acad Sci USA* 90: 2207-2211, 1993.
58. Nguyen T L. Targeting RSK: an overview of small molecule inhibitors. *Anti-Cancer Agents Med Chem* 8: 710-716, 2008.
59. Olson A L, Swigris J J, Lezotte D C, Norris J M, Wilson C G and Brown K K. Mortality from pulmonary fibrosis increased in the United States from 1992 to 2003. *Am J Respir Crit Care Med* 176: 277-284, 2007.
60. Orens J B, Estenne M, Arcasoy S, Conte J V, Corris P, Egan J J, Egan T, Keshavjee S, Knoop C, Kotloff R, Martinez F J, Nathan S, Palmer S, Patterson A, Singer L, Snell G, Studer S, Vachiary J L, Gianville A R. *J Heart Lung Transplant* 25: 745-755, 2006.
61. Palombella V J, Rando O J, Goldberg A L and Maniatis T. The ubiquitin-proteasome pathway is required for processing the NF-kB 1 precursor protein and the activation of NF-kB. *Cell* 78: 773-785, 1994.
62. Pantelidis P, Fanning G C, Wells A U, Welsh K I and du Bois R M. Analysis of tumor necrosis factor-alpha, lymphotoxin-alpha, tumor necrosis factor receptor II, and interleukin-6 polymorphisms in patients with idiopathic pulmonary fibrosis. *Am J Respir Crit Care Med* 163: 1432-1436, 2001.
63. Pardo A, Gibson K, Cisneros J, Richards T J, Yang Y, Becerril C, Yousem S, Herrera I, Ruiz V, Selman Ms and Kaminski N. Up-Regulation and Profibrotic Role of Osteopontin in Human Idiopathic Pulmonary Fibrosis. *PLoS Med* 2: e251, 2005.
64. Pedroza M, Schneider D J, Karmouty-Quintana H, Coote J, Shaw S, Corrigan R, Molina J G, Alcorn J L, Galas D, Gelinas R and Blackburn M R. Interleukin-6 contributes to inflammation and remodeling in a model of adenisone mediated lung injury. *PLOS One* 6: e22667, 2011.
65. Phillipps R J, Burdick M J, Hong K, Lutz M A, Murray L A, Xue Y Y, Belperio J A, Keane M P and Strieter R M. Circulating fibrocytes traffic to the lungs in response to CXCL 12 and mediate fibrosis. *J Clin Invest* 114: 438-446, 2004.
66. Pulendran B, Tang H and Manicassamy S. Programming dendritic cells to induce TH2 and tolerogenic responses. *Nature Immunology* 11: 647-655, 2010.
67. Raghu G, Weycker D, Edelsberg J, Bradford W Z and Oster G. Incidence and prevalence of idiopathic pulmonary fibrosis. *Am J Res Critical Care Med* 174: 810-816, 2006.
68. Ramamoorthy S, Donohue M and Buck M. Decreased Jun-D and myogenin expression in muscle wasting of human cachexia. *American J of Physiology, Endocrinology and Metabolism* 297: e392-401, 2009.
69. Rosati M, Valentin A, Patenaude D J and Pavlakis G N. CCAT-Enhancer-binding protein beta (C/EBP beta) activates CCR5 promotor: increased C/EBP beta and CCR5 in T lymphocytes from HIV-1-infected individuals. *J Immunol* 167: 1654-1662, 2001.
70. Ruddy M J, Wong G C, Liu X K, Yamamoto H, Kasayama S, Kirkwood K L and Gaffen S L. Functional Cooperation between Interleukin-17 and Tumor Necrosis Factor-is Mediated by CCAAT/Enhancer-binding Protein Family Members. *The Journal of Biological Chemistry* 279: 2559-2567, 2004.
71. Ruffell D, Mourkioti F, Gambardella A, Kirstetter. P, Lopez R G, Rosenthal N and Nerlov C. A CREB-C/EBPbeta cascade induces M2 macrophage-specific gene expression and promotes muscle injury repair. *PNAS* 106: 17475-17480, 2009.
72. Sato A K, Viswanathan M, Kent R B and Wood C R. Therapeutic peptides: technological advances driving peptides into development. *Curr Opin Biotech* 17: 638-642, 2006.
73. Schreck R, Rieber P and Baeuerle P A. Reactive oxygen intermediates as apparently widely used messengers in the activation of the NF-kB transcription factor and HIV-1. *EMBO J* 10: 2247-2258, 1991.
74. Schrier D J, Phan S H and McGarry B M. The effects of the nude (nu/nu) mutation on bleomycin-induced pulmonary fibrosis. A biochemical evaluation. *The American Rev of Respiratory Disease* 127: 614-617, 1983.
75. Schwabe R F and Sakurai H. IKK phosphorylates p65 at S468 in transactivation domain 2. *FASEB J* 19: 1758-1760, 2005.

76. Screpanti I, Musiani P, Bellavia D, Cappelletti M, Aiello F B, Maroder M, Frati L, Modesti A, Gulino A and Poli V. Inactivation of the IL-6 Gene Prevents Development of Multicentric Castleman's Disease in C/EBPβ-deficient Mice. *Journal of Experimental Medicine* 184: 1561-1566, 1996.

77. Selman M, King T E and Pardo A. Idiopathic pulmonary fibrosis: prevailing and evolving hypotheses about its pathogenesis and implications for therapy. *Ann Intern Med* 134: 136-151, 2001.

78. Shen F, Li N, Gade P, Kalvakolanu D V, Weibley T, Doble B, Woodgett J R, Wood T D and Gaffen S L. IL-17 Receptor signaling inhibits C/EBPbeta by sequential phosphorylation of the regulatory 2 domain. *Sci Signal* 2: ra8, 2009.

79. Smith J A, Poteet-Smith C, Xu Y, Errington T M, Hecht S M and Lannigan D A. Identification of the first specific inhibitor of p90 ribosomal S6 kinase (RSK) reveals an unexpected role for RSK in cancer cell proliferation. *Cancer Res* 65: 1027-1034, 2005.

80. Solt L A, Kumar N, Nuhant P, Wang Y, Lauer J L, Liu J, Istrate M A, Kamenecka T M, Roush W R, Vidovic D, Schurer S C, Xu J, Wagoner G, Drew P D, Griffin P R and Burris T P. Suppression of TH17 differentiation and autoimmunity by a synthetic ROR ligand. *Nature* 472: 491-494, 2011.

81. Spierings D, McStay G, Saleh M, Bender C, Chipuk J, Maurer U and Green D. Connected to death: the (unexpurgated) mitochondrial pathway of apoptosis. *Science* 310: 66-67, 2005.

82. Stein B and Baldwin A. Distinct mechanisms for regulation of the interleukin-8 gene involve synergism and cooperativity between C/EBP and NF-kB. *Mol Cell Biol* 13: 7191-7198, 1993.

83. Stein B, Cogswell P and Baldwin A, Jr. Functional and physical associations between NF-kB and C/EBP family members: Rel domain-bZIP interaction. *Mol Cell Biol* 13: 3964-3974, 1993.

84. Szabo S J, Kim S T, Costa G L, Zhang X, Fathman C G and Glimcher L H. A Novel Transcription Factor, T-bet, Directs Th1 Lineage Commitment. *Cell* 100: 655-669, 2000.

85. Takeshita F, Suzuki K, Sasaki S, Ishii N, Klinman D M and Ishii K J. Transcriptional Regulation of the Human TLR9 Gene. *J Immunol* 173: 2552-2561, 2004.

86. Trautwein C, Caelles C, van der Geer P, Hunter T, Karin M and Chojkier M. Transactivation by NF-IL6/LAP is enhanced by phosphorylation of its activation domain. *Nature* 364: 544-547, 1993.

87. Trautwein C, van der Geer P, Karin M, Hunter T and Chojkier M. Protein kinase A and C site-specific phosphorylations of LAP (NF-IL6) modulate its binding affinity to DNA-recognition elements. *J Clin Invest* 93: 2554-2561, 1994.

88. Trujillo G, Meneghin A, Flaherty K R, Sholl L M, Myers J L, Kazerooni E A, Gross B H, Oak S R, Coelho A L, Evanoff H, Day E, Toews G B, Joshi A D, Schaller M A, Waters B, Jarai G, Westwick J, Kunkel S L, Martinez F J and Hogaboam C M. TLR9 Differentiates Rapidly from Slowly Progressing Forms of Idiopathic Pulmonary Fibrosis. *Science Translational Medicine* 2: 57ra82, 2010.

89. Veronese F M and Pasut G. PEGylation, successful approach to drug delivery. *Drug Discov Today* 10: 1451-1458, 2005.

90. Wegner M, Cao Z and Rosenfeld M G. Calcium-regulated phosphorylation within the leucine zipper of C/EBP. *Science* 256: 370-373, 1992.

91. Wilson M S, Elnekave E, Mentink-Kane M M, Hodges M G, Pesce J T, Ramalingam T R, Thompson R W, Kamanaka M, Flavell R A, Keane-Myers A, Cheever A W and Wynn T A. IL-13Ra2 and IL-10 coordinately suppress airway inflammation, airway-hyperreactivity, and fibrosis in mice. *Journal of Clinical Investigation* 117: 2941-2951, 2007.

92. Wilson M S, Madala S K, Ramalingam T R, Gochuico B R, Rosas I O, Cheever A W and Wynn T A. Bleomycin and IL-1-mediated pulmonary fibrosis is IL-17A dependent. *Journal of Experimental Medicine* 207: 535-552, 2010.

93. Yang D D, Conze D, Whitmarsh A J, Barrett T, Davis R J, Rinctn M and Flavell R A. Differentiation of CD4+ T Cells to Th1 Cells Requires MAP Kinase JNK2. *Immunity* 9: 575-585, 1998.

94. Zhang K, Gharaee-Kermani M, McGarry B, Remick D and Phan S H. TNF-alpha-mediated lung cytokine networking and eosinophil recruitment in pulmonary fibrosis. *Journal of Immunology* 158: 954-959, 1997.

95. Zheng W-P and Flavell R A. The Transcription Factor GATA-3 Is Necessary and Sufficient for Th2 Cytokine Gene Expression in CD4 T Cells. *Cell.*

REFERENCES FOR MACROPHAGE INFLAMMASOME ACTIVATION AND LIVER INJURY

1. Szabo, G. & Petrasek, J. Inflammasome activation and function in liver disease. *Nature Reviews Gastroenterology & Hepatology* 12, 387-400 (2015).

2. Chung, R. & Podolsky, D. Cirrhosis and its Complications. *Harrison's Principles of Internal Medicine*. McGraw-Hill: New York, 1754-1767 (2005).

3. Chojkier, M. Regulation of collagen gene expression. *Liver Growth and Repair*. Chapman & Hall: London, 430-450 (1998).

4. Chojkier, M. & Fierer, J. D-Galactosamine hepatotoxicity is associated with endotoxin sensitivity and mediated by lymphoreticular cells in mice. *Gastroenterology* 88, 115-121 (1985).

5. Duffield, J. S. et al. Selective depletion of macrophages reveals distinct, opposing roles during liver injury and repair. *J Clin. Invest.* 115, 56-65 (2005).

6. Petrasek, J. et al. IL-1 receptor antagonist ameliorates inflammasome-dependent alcoholic steatohepatitis in mice. *The Journal of Clinical Investigation* 122, 3476-3489 (2012).

7. Ouyang, X. et al. Adenosine is required for sustained inflammasome activation via the A2A receptor and the HIF-la pathway. *Nat Commun.* 4, 1-18 (2013).

8. Tsutsui, H. et al. Caspase-1-Independent, Fas/Fas Ligand-Mediated IL-18 Secretion from Macrophages Causes Acute Liver Injury in Mice. *Immunity* 11, 359-367 (1999).

9. Diehl, A. M. Neighborhood watch orchestrates liver regeneration. *Nature Medicine* 18., 497-499 (2012).

10. Martinon, F., Burns, K. & Tschopp, J. The inflammasome: a molecular platform triggering activation of inflammatory caspases and processing of proIL-beta. *Molecular Cell* 10, 417-426 (2002).

11. Franchi, L., Eigenbrod, T., Munoz-Planillo, R. & Nunez, G. The inflammasome: a caspase-1-activation platform that regulates immune responses and disease pathogenesis. *Nat. Immunol.* 10, 241-247 (2009).

12. Descombes, P., Chojkier, M., Lichtsteiner, S., Falvey, E. & Schibler, U. LAP, a novel member of the C/EBP gene family, encodes a liver-enriched transcriptional activator protein. *Genes Dev* 4, 1541-1551 (1990).

13. Akira, S. et al. A nuclear factor for IL-6 expression (NF-IL6) is a member of a C/EBP family. *The EMBO Journal* 9, 1897-1906 (1990).
14. Poli, V., Mancini, F. P. & Cortese, R. IL6-DBP, a nuclear protein involved in interleukin-6 signal transduction, defines a new family of leucine zipper proteins related to C/EBP. *Cell* 63, 643-653 (1990).
15. Iwama, A. et al. Reciprocal roles for CCAAT/enhancer binding protein (C/EBP) and PU.1 transcription factors in Langerhans cell commitment. *J. Exp. Med.* 195, 547-558 (2002).
16. Sebastian, T. & Johnson, P. F. Stop and go: antiproliferative and mitogenic functions of the transcription factor C/EBPb. *Cell Cycle* 5, 953-957 (2006).
17. Friedman, A. D. Transcriptional control of granulocyte and monocyte development. *Oncogene* 26, 6816-6828 (2007).
18. Buck, M., Poli, V., van der Geer, P., Chojkier, M. & Hunter, T. Phosphorylation of rat serine 105 or mouse threonine 217 in C/EBP beta is required for hepatocyte proliferation induced by TGF alpha. Mol Cell 4, 1087-1092 (1999).
19. Buck M, C. M. C/EBPβ Associates With Caspase 8 Complex Proteins and Modulates Apoptosis in Hepatic Stellate Cells. *J Clin Gastroenterol* 41, S295-S299 (2001).
20. Buck, M. & Chojkier, M. Signal Transduction in the Liver: C/EBPb Modulates Cell Proliferation and Survival. *Hepatology* 37, 731-738 (2003).
21. Buck, M. & Chojkier, M. A ribosomal S-6 kinase-mediated signal to C/EBP-beta is critical for the development of liver fibrosis. *PLoS One* 2, e1372 (2007).
22. Trautwein, C. et al. Transactivation by NF-IL6/LAP is enhanced by phosphorylation of its activation domain. *Nature* 364, 544-547 (1993).
23. Buck, M. & Chojkier, M. C/EBP(beta) phosphorylation rescues macrophage disfunction and apoptosis induced by anthrax lethal toxin. *Am J Physiol Cell Physiol* 293, C1788-C1796 (2007).
24. Ramamoorthy, S., Donohue, M. & Buck, M. Decreased Jun-D and myogenin expression in muscle wasting of human cachexia. *Am J Physiol Endocrinol Metab* 297, E392-401 (2009).
25. Chojkier, M. Troglitazone and liver injury: in search of answers. *Hepatology* 41, 237-246 (2005).
26. Ogasawara, J. et al. Lethal effect of the anti-Fas antibody in mice. *Nature* 364, 806-809 (1993).
27. Buck, M., Poli, V., Hunter, T. & Chojkier, M. C/EBPbeta phosphorylation by RSK creates a functional XEXD caspase inhibitory box critical for cell survival. *Mol Cell* 8, 807-816 (2001).
28. Malhi, H. & Gores, G. J. Cellular and Molecular Mechanisms of Liver Injury. *Gastroenterology* 134, 1641-1654 (2008).
29. Cieslik, K., Zhu, Y. & Wu, K. K. Salicylate Suppresses Macrophage Nitric-oxide Synthase-2 and Cyclo-oxygenase-2 Expression by Inhibiting CCAAT/Enhancer-binding Protein-beta Binding via a Common Signaling Pathway. *Journal of Biological Chemistry* 277, 49304-49310 (2002).
30. Rudolph, K. L., Chang, S., Millard, M., Schreiber-Agus, N. & Depinho, R. A. Inhibition of experimental liver cirrhosis in mice by telomerase gene delivery. *Science* 287, 1253-1258 (2000).
31. Julien, B. et al. Antifibrogenic role of the cannabinoid receptor CB2 in the liver. *Gastroenterology* 128, 742-755 (2005).
32. Walsh, J. G., Muruve, D. A. & Power, C. Inflammasomes in the CNS. *Nature Reviews Neuroscience* 15, 84-97 (2014).
33. Martinon, F., Mayor, A. & Tschopp, J. The Inflammasomes: Guardians of the Body. *Annual Review of Immunology* 27, 229-265 (2009).
34. Tabuenca, J. M. Toxic-allergic syndrome caused by ingestion of rapeseed oil denatured with aniline. *The Lancet* 318, 567-568 (1981).
35. Solis-Herruzo, J. A. et al. Hepatic injury in the toxic epidemic syndrome caused by ingestion of adulterated cooking oil. *Hepatology* 4, 131-139 (1984).
36. Dadley-Moore, D. Switching on the inflammasome. *Nature Reviews Immunology* 6, 88-89 (2006).
37. Lamkanfi, M. Emerging inflammasome effector mechanisms. *Nat Rev Immunol* 11, 213-220 (2011).
38. Ryo, K. et al. Significance of Fas antigen-mediated apoptosis in human fulminant hepatic failure. *Am J Gastroenterol* 95, 2047-2055 (2000).
39. Taieb, J., Mathurin, P., Poynard, T., Gougerot-Pocidalo, M. A. & Chollet-Martin, S. Raised plasma soluble Fas and Fas-ligand in alcoholic liver disease. *Lancet* 351, 1930-1931 (1998).
40. Csóka, B. et al. A2A adenosine receptors and C/EBPbeta are crucially required for IL-10 production by macrophages exposed to *Escherichia coli*. *Blood* 110, 2685-2695 (2007).
41. Mehal, W. Z. The Inflammasome in Liver Injury and Non-Alcoholic Fatty Liver Disease. *Digestive Diseases* 32, 507-515 (2014).
42. Murray, Peter J. et al. Macrophage Activation and Polarization: Nomenclature and Experimental Guidelines. *Immunology* 41, 14-20 (2014).
43. Brenner D A, Alcorn J M, Feitelberg S P, Leffert H L, Chojkier M. Expression of collagen genes in the liver. *Mol Biol Med.* 7, 105-15 (1990).

\* \* \*

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

What is claimed is:

1. An isolated peptide selected from the group consisting of Lys-Ser-Lys-Ala-Lys-Lys-Ala-Val-Asp-Lys-His-Ser-Asp (SEQ ID NO: 3), Lys-Ala-Lys-Lys-Ala-Val-Asp-Lys-His-Ser (SEQ ID NO: 4), and Ala-Lys-Lys-Ala-Val-Asp-Lys-His (SEQ ID NO: 5).

2. The peptide of claim 1, wherein said peptide is capable of selectively inhibiting phosphorylation of human CCAAT/Enhancer Binding Protein-β (C/EBPβ) at Threonine 266 (Thr 266).

3. The peptide of claim 1, wherein said peptide is capable of inhibiting activation of myofibroblasts and/or macrophage inflammasome.

4. The peptide of claim 1, wherein said peptide further comprises polyethylene glycol (PEG).

5. The peptide of claim 1, wherein said peptide further comprises a linker of acid (Ac) or mercaptopropionic acid (Mpr).

6. The peptide of claim 1, wherein said peptide is a cyclic peptide.

7. An isolated peptide selected from the group consisting of:
Lys-DAla-DVal-Asp,
Ac-Lys-DAla-DVal-Asp,
Mpr-Lys-DAla-DVal-Asp,
PEG-Lys-DAla-DVal-Asp,
PEG-Ac-Lys-DAla-DVal-Asp,
PEG-Mpr-Lys-DAla-DVal-Asp,
Lys-DAla-Val-Asp,
Ac-Lys-DAla-Val-Asp,
Mpr-Lys-DAla-Val-Asp,
PEG-Lys-DAla-Val-Asp,
PEG-Ac-Lys-DAla-Val-Asp,
PEG-Mpr-Lys-DAla-Val-Asp,
Lys-Ala-DVal-Asp,
Ac-Lys-Ala-DVal-Asp,
Mpr-Lys-Ala-DVal-Asp,
PEG-Lys-Ala-DVal-Asp,
PEG-Mpr-Lys-Ala-DVal-Asp, and
PEG-Mpr-Lys-Ala-DVal-Asp,
wherein the carboxy terminal group of the peptide is OH, OCH3, or NH2 group.

8. A pharmaceutical composition comprising one or more peptide(s) of claim 1 or claim 7 and a pharmaceutically acceptable carrier.

9. An isolated peptide, wherein said peptide has the structure as shown in formula (I):

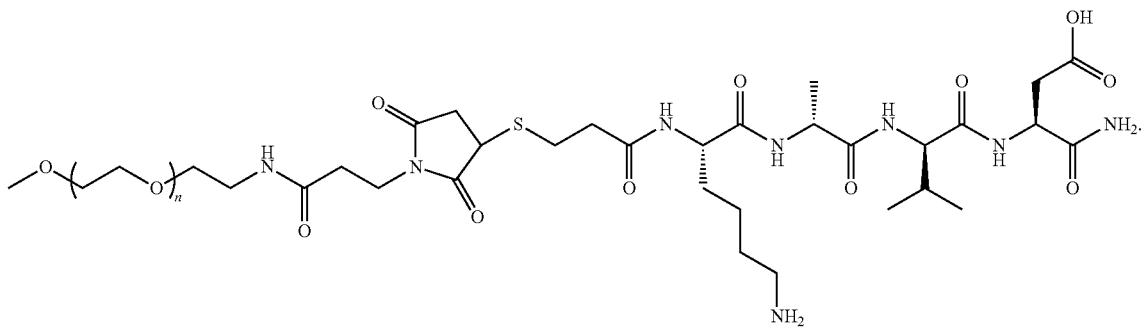

10. A method for treating a tissue fibrotic disease in a subject in need thereof comprising administering to the subject an effective amount of one or more peptides of claim 1 or claim 7.

11. The method of claim 10, wherein said disease is associated with liver injury, liver inflammation and/or liver fibrosis.

12. The method of claim 10, wherein said disease is liver cirrhosis or liver fibrosis of any etiology.

13. The method of claim 11, wherein the disease is selected from the group consisting of non-alcoholic fatty liver disease (NAFLD), non-alcoholic steatohepatitis (NASH), alcoholic fatty liver disease, alcoholic steatohepatitis, hepatic steatosis, autoimmune hepatitis, chronic hepatitis C, chronic hepatitis B, primary biliary cirrhosis, secondary biliary cirrhosis, sclerosing cholangitis, alpha-1-antitrypsin deficiency, Wilson's disease, and biliary atresia.

14. The method of claim 10, wherein said disease is associated with lung injury, lung inflammation and/or lung fibrosis.

15. The method of claim 10, wherein said disease is associated with kidney injury, kidney inflammation and/or kidney fibrosis.

16. The method of claim 10, wherein the disease is selected from the group consisting of skin fibrosis secondary to burns, keloids, hypertrophic post-surgical wounds, scleroderma, esophageal or gastro-intestinal fibrosis secondary to corrosive materials, esophageal or gastro-intestinal fibrosis secondary to inflammatory diseases, fibrosis secondary to ischemic diseases, peritoneal fibrosis, pancreatic fibrosis, post-radiation fibrosis, cardiac fibrosis secondary to infarcts, brain fibrosis secondary to ischemia or infarcts, post-traumatic brain fibrosis, post-traumatic muscle fibrosis, and synovial/joint fibrosis.

17. A method for treating an inflammatory disease in a subject in need thereof comprising administering to the subject an effective amount of one or more peptides of claim 1 or claim 7.

18. The method of claim 17, wherein said disease is selected from the group consisting of alcoholic liver disease, non-alcoholic steato-hepatitis (NASH), autoimmune hepatitis, chronic hepatitis C, chronic hepatitis B, primary biliary cirrhosis, secondary biliary cirrhosis, sclerosing cholangitis, alpha-1-antitrypsin deficiency, Wilson's disease, biliary atresia, idiopathic pulmonary fibrosis, radiation-induced pneumonitis, chronic obstructive pulmonary disease, lung emphysema, lung chronic infections and/or inflammation, glomerulonephritis, interstitial-tubular fibrosis, skin inflammation secondary to burns, scleroderma, psoriasis, inflammatory bowel diseases, esophageal injury and/or inflammation, esophageal or gastro-intestinal inflammation post-radiation, inflammatory cardiomyopathy, brain inflammation post-trauma, Alzheimer's disease, encephalitis, meningitis, myositis, and arthritis.

* * * * *